(12) United States Patent
Gangjee

(10) Patent No.: US 9,994,586 B2
(45) Date of Patent: Jun. 12, 2018

(54) MONOCYCLIC, THIENO, PYRIDO, AND PYRROLO PYRIMIDINE COMPOUNDS AND METHODS OF USE AND MANUFACTURE OF THE SAME

(71) Applicant: Duquesne University of the Holy Spirit, Pittsburgh, PA (US)

(72) Inventor: Aleem Gangjee, Allison Park, PA (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 0 days. days.

(21) Appl. No.: 15/239,080

(22) Filed: Aug. 17, 2016

(65) Prior Publication Data

US 2017/0050978 A1 Feb. 23, 2017

Related U.S. Application Data

(60) Provisional application No. 62/205,907, filed on Aug. 17, 2015.

(51) Int. Cl.
| | | |
|---|---|---|
| *C07D 495/04* | (2006.01) | |
| *C07D 487/04* | (2006.01) | |
| *C07D 471/04* | (2006.01) | |

(52) U.S. Cl.
CPC ......... *C07D 495/04* (2013.01); *C07D 471/04* (2013.01); *C07D 487/04* (2013.01)

(58) Field of Classification Search
CPC ............................. C07D 495/04; A61K 31/519
See application file for complete search history.

(56) References Cited

U.S. PATENT DOCUMENTS

2007/0213305 A1* 9/2007 Cai ...................... A61K 31/519
514/151

\* cited by examiner

*Primary Examiner* — Susanna Moore
(74) *Attorney, Agent, or Firm* — Eckert Seamans Cherin & Mellott, LLC; Carol A. Marmo

(57) ABSTRACT

The present invention provides a compound of Formula XXVIII:

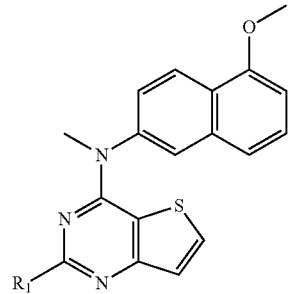

werein $R_1$ is H or $CH_3$, and optionally including a salt or a hydrate of said compound.

1 Claim, 17 Drawing Sheets

Triemthoprim (TMP)

Pyrimethamine

Trimetrexate (TMQ)

Piritrexim (PTX)

(Section I- Figure 1)

(Section I- Figure 2)

(Section II- Figure 1)

(Section II- Figure 2)

(Section III- Figure 1)

(Section III- Figure 2)

AGF17

AGF233 X = CH₂
AGF220 X = O
AGF256 X = NH (Section IV- Figure 1)

1

2

3

4

5

6

7

8

9

10

(Section V- Figure 1)

(Section V- Figure 2)

(Section V- Figure 3)

(Section VI- Figure 1)

(Section VI- Figure 2)

(Section VI- Figure 3)

paclitaxel R=PhCO
docetaxel R=$^t$BuOCO

|  | $R_1$ | $R_2$ | $R_3$ |
|---|---|---|---|
| vinblastine | $CH_3$ | $OCH_3$ | $COCH_3$ |
| vincristine | CHO | $OCH_3$ | $COCH_3$ |
| vindesine | $CH_3$ | $NH_2$ | H | laulimalide colchicine combretastatin A4

(Section VII-Figure 1)

(Section VII- Figure 2)

(Section VIII- Figure 1)

(Section VIII- Figure 2)

MONOCYCLIC, THIENO, PYRIDO, AND PYRROLO PYRIMIDINE COMPOUNDS AND METHODS OF USE AND MANUFACTURE OF THE SAME

CROSS-REFERENCE TO RELATED APPLICATION

This utility patent application claims the benefit of co-pending U.S. Provisional Patent Application Ser. No. 62/205,907, filed Aug. 17, 2015. The entire contents of U.S. Provisional Patent Application Ser. No. 62/205,907 is incorporated by reference into this utility patent application as if fully written herein.

STATEMENT REGARDING FEDERALLY SPONSORED RESEARCH

This invention was made with government support under grant numbers R01CA142868, R01CA166711, R01 CA152316, and R01CA53535 awarded by the National Institutes of Health, National Cancer Institute, and under grant number RO1AI098458 awarded by the National Institutes of Health, National Institute of Allergy and Infectious Diseases, and Support Grant P30 CA054174 awarded by the CTRC Cancer Center, and NSF equipment grant NMR: CHE 0614785, National Science Foundation. The government has certain rights in the invention.

BACKGROUND OF THE INVENTION

1. Field of the Invention

This invention provides monocyclic, thieno, pyrido, and pyrrolo pyrimidine compounds and methods of use and manufacture of the same.

2. Description of the Background Art

Pneumocystis jirovecii pneumonia formerly identified as Pneumocystis carinii pneumonia (PCP) is the most common life-threatening opportunistic infection in immuno-deficient patients with AIDS, some types of cancers or undergoing organ transplant procedures. With the advent of highly active antiretroviral therapy (HAART), PCP rates have been reduced significantly. Unfortunately, it still remains a serious infection in 30-40% of immunocompromised patients if their CD4 cell count drops below 50. While classified as a fungus, *Pneumocystis jirovecii* (pj), does not respond to antifungal treatments. The recommended therapeutic approach for the treatment PCP is trimethoprim (TMP)-sulfamethoxazole (SMX), but due to sulfonamide allergies and increasing drug-resistant strains, in many cases use of TMP-SMX is not recommended. The second line treatment involves potent, but non-selective DHFR inhibitors such as trimetrexate (TMQ) and piritrexim (PTX) which cause myelosuppression and require co-administration of leucovorin increasing the cost of therapy. There is a significant unmet clinical need for new anti-infective agents as reported by the Centers of Disease Control and Prevention and World Health Organization to overcome the threat of drug-resistant strains. The present invention discloses a series of 6-substituted pyrido[3,2-d]pyrimidines that are selective and potent inhibitors of pjDHFR. The synthesis and biological evaluation of analogs designed to optimize selectivity and potency for pjDHFR over hDHFR is disclosed.

SUMMARY OF THE INVENTION

The present invention provides a compound of Formula I:

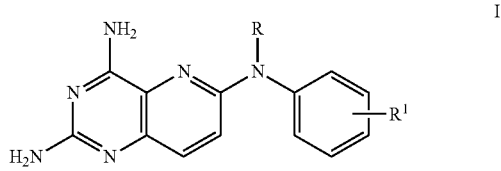

I wherein R is H, a methyl group, an ethyl group, a n-propyl group, an iso-propyl group, or a n-butyl group; and $R^1$ is H, a 4'-methyl group, a 4'-OH, a 4'-OMe group, a 2',3'-$C_2H_4$ group, a; 3',4'-$C_2H_4$ group, a 3',4'-diF, a 3',4',5'-triF, or a 4'-$OCF_3$; and optionally including a salt or a hydrate of said compound.

Another embodiment of this invention provides a pharmaceutical composition comprising a therapeutically effective amount of a compound of Formula I and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula I, or a pharmaceutical composition comprising a therapeutically effective amount of a compound of Formula I and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula V:

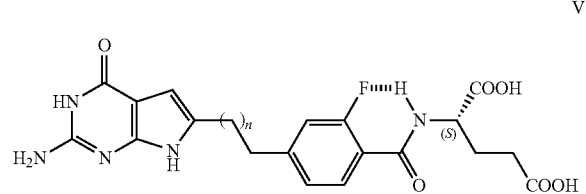

V wherein n is 3; and optionally including a salt or a hydrate of said compound.

Another embodiment of this invention provides a pharmaceutical composition comprising a therapeutically effective amount of a compound of Formula V and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula V, or a pharmaceutical composition comprising a therapeutically effective amount of a compound of Formula V and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula VI:

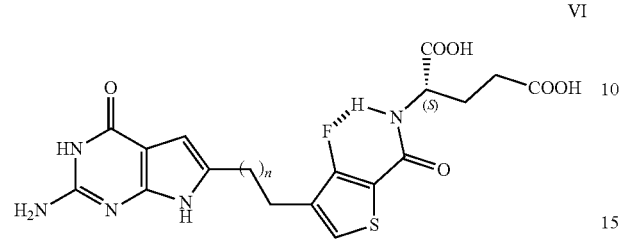

VI wherein n is 3; and optionally including a salt or a hydrate of said compound.

Another embodiment of this invention provides a pharmaceutical composition comprising a therapeutically effective amount of a compound of Formula VI and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula VI, or a pharmaceutical composition comprising a therapeutically effective amount of a compound of Formula VI and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXVI:

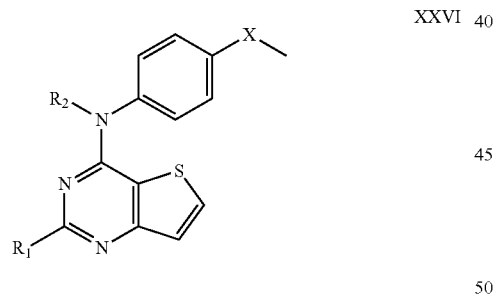

XXVI wherein X is O or S; $R_1$ is H or $CH_3$; and $R_2$ is H or $CH_3$, and optionally including a salt or a hydrate of said compound.

Another embodiment of this invention provides a pharmaceutical composition comprising a therapeutically effective amount of a compound of Formula XXVI and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXVI, or a pharmaceutical composition comprising a therapeutically effective amount of a compound of Formula XXVI and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXVII:

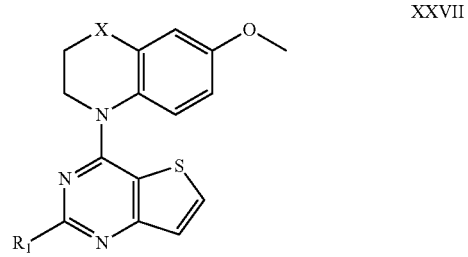

XXVII wherein X is $CH_2$ or O, and $R_1$ is H or $CH_3$, and optionally including a salt or a hydrate of said compound.

Another embodiment of this invention provides a pharmaceutical composition comprising a therapeutically effective amount of a compound of Formula XXVII and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXVII, or a pharmaceutical composition comprising a therapeutically effective amount of a compound of Formula XXVII and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXVIII:

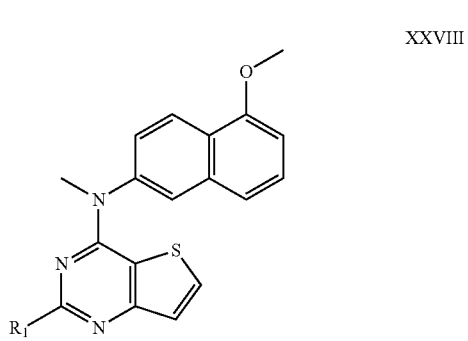

XXVIII wherein $R_1$ is H or $CH_3$; and optionally including a salt or a hydrate of said compound.

Another embodiment of this invention provides a pharmaceutical composition comprising a therapeutically effective amount of a compound of Formula XXVIII and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXVII, or a pharmaceutical composition comprising a therapeutically effective amount of a compound of Formula XXVIII and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXIX:

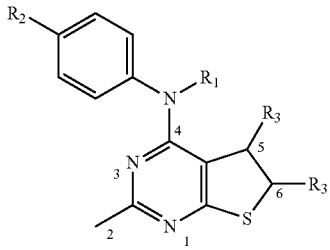

XXIX wherein $R_1$ is H or $CH_3$; $R_2$ is $SCH_3$ or $OCH_3$; and $R_3$ is H or $CH_3$; and optionally including a salt or a hydrate of said compound.

Another embodiment of this invention provides a pharmaceutical composition comprising a therapeutically effective amount of a compound of Formula XXIX and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXIX, or a pharmaceutical composition comprising a therapeutically effective amount of a compound of Formula XXIX and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXX:

XXX wherein X is $CH_2$ or O; and $R_1$ is H or $CH_3$; and optionally including a salt or a hydrate of said compound.

Another embodiment of this invention provides a pharmaceutical composition comprising a therapeutically effective amount of a compound of Formula XXX and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXX, or a pharmaceutical composition comprising a therapeutically effective amount of a compound of Formula XXX and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXXI:

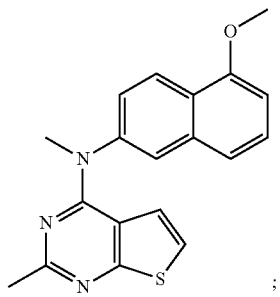

XXXI

;

and optionally including a salt or a hydrate of said compound.

Another embodiment of this invention provides a pharmaceutical composition comprising a therapeutically effective amount of a compound of Formula XXXI and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXXI, or a pharmaceutical composition comprising a therapeutically effective amount of a compound of Formula XXXI and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXXII:

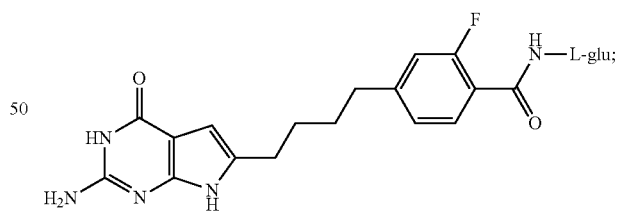

XXXII and optionally including a salt or a hydrate of said compound.

Another embodiment of this invention provides a pharmaceutical composition comprising a therapeutically effective amount of a compound of Formula XXXII and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXXII, or a pharmaceutical composition comprising a therapeutically effective amount of a compound of Formula XXXIIV and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXXIII:

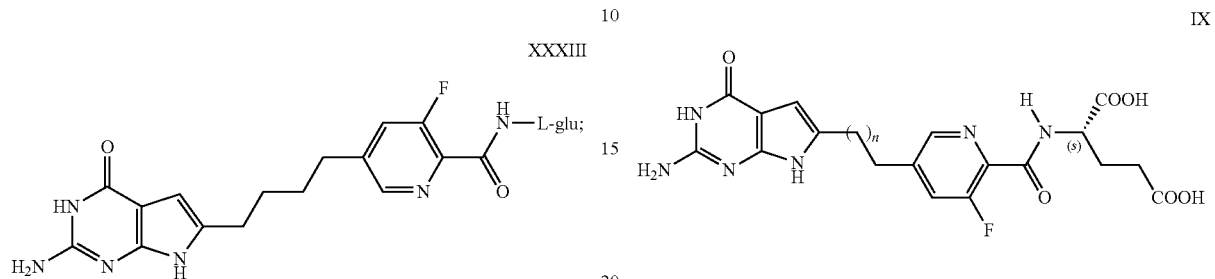

XXXIII and optionally including a salt or a hydrate of said compound.

Another embodiment of this invention provides a pharmaceutical composition comprising a therapeutically effective amount of a compound of Formula XXXIII and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXXIII, or a pharmaceutical composition comprising a therapeutically effective amount of a compound of Formula XXXIII and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula XXXIV:

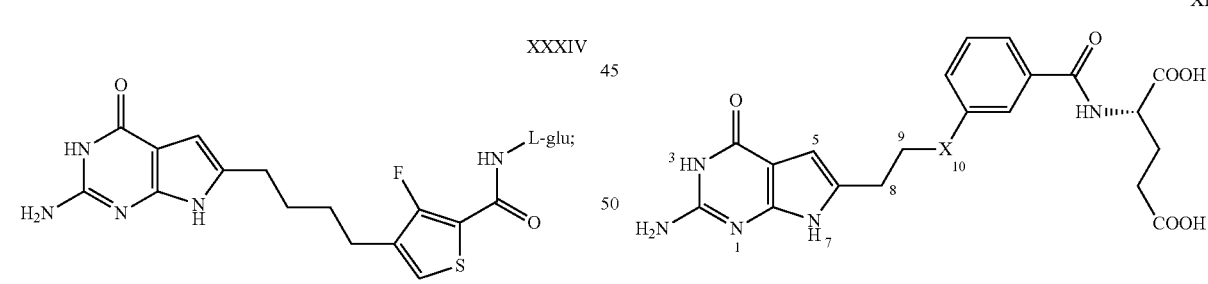

XXXIV and optionally including a salt or a hydrate of said compound.

Another embodiment of this invention provides a pharmaceutical composition comprising a therapeutically effective amount of a compound of Formula XXXIV and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XXXIV, or a pharmaceutical composition comprising a therapeutically effective amount of a compound of Formula XXXIV and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of Formula IX:

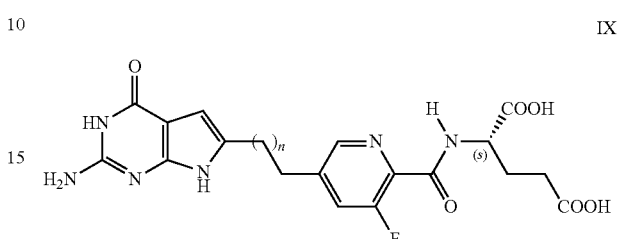

IX wherein n is 3; and optionally including a salt or a hydrate of said compound.

Another embodiment of this invention provides a pharmaceutical composition comprising a therapeutically effective amount of a compound of Formula IX and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula IX, or a pharmaceutical composition comprising a therapeutically effective amount of a compound of Formula IX and optionally comprising a pharmaceutically acceptable salt or hydrate of said compound, to the patient. Preferably, this pharmaceutical composition further comprises at least one pharmaceutically acceptable carrier.

Another embodiment of this invention provides a compound of the Formula XI:

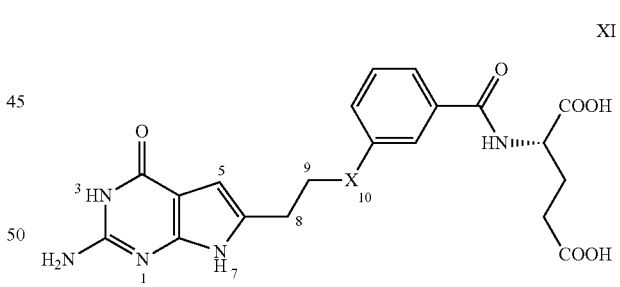

XI wherein X is $CH_2$, O, or NH; and optionally including a salt or a hydrate of said compound.

Another embodiment of this invention provides a pharmaceutical composition comprising a therapeutically effective amount of a compound of Formula XI and optionally comprising a pharmaceutically acceptable salt or hydrate of said compound. Preferably, this pharmaceutical composition further comprises at least one pharmaceutically acceptable carrier.

Another embodiment of this invention provides a method of treating a patient having cancer comprising administering a therapeutically effective amount of a compound of Formula XI, or a pharmaceutical composition comprising a therapeutically effective amount of a compound of Formula XI and optionally comprising a pharmaceutically acceptable salt or hydrate of said compound, to the patient. Preferably, this pharmaceutical composition further comprises at least one pharmaceutically acceptable carrier.

Other embodiments of this invention include any one of the compounds of this invention as disclosed by the chemical formula set forth in the detailed description of this invention. Pharmaceutical compositions comprising the compounds represented by the chemical formula of this invention and optionally comprising a pharmaceutically acceptable salt or hydrate of any one of said compounds of this invention are within the scope of this invention. Preferably, these pharmaceutical compositions further comprises at least one pharmaceutically acceptable carrier. may be Other embodiments of this invention include methods of treating a patient having cancer comprising administering a therapeutically effective amount of any one or more of the compounds, or salts or hydrates of these compounds, of this invention as disclosed by the chemical formula set forth in the detailed description of this invention, or a pharmaceutical composition comprising a therapeutically effective amount of any one or more of the compounds, or salts or hydrates of these compounds, of this invention as described in the detailed description of this invention and optionally including one or more acceptable pharmaceutical carriers, to the patient.

DETAILED DESCRIPTION OF THE INVENTION

Figure 1:
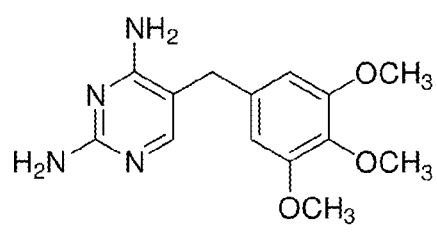
FIG. 1 (Section I—FIG. 1) shows the chemical structures of known dihydrofolate reductase inhibitor compounds.
Figure 1:
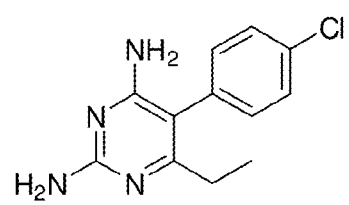
Figure 1:
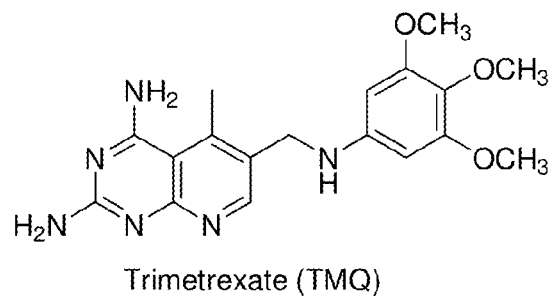
Figure 1:
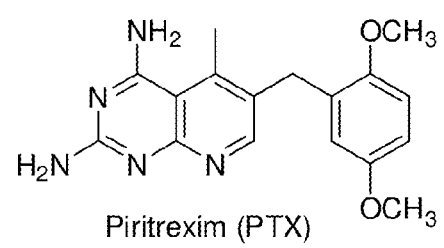

As used herein, the term "effective amount" or "therapeutically effective amount" is defined as the amount of a compound or composition required to effect a particular result, such as for example, but not limited to, treating a patient for a disease, including for example, cancer.

As used herein, the term "patient" includes all members of the animal kingdom, including but not limited to, Homo sapiens, warm and cold blooded animals, and reptiles.

The compounds of this application may be administered to a patient in any suitable pharmaceutical form, with or in any suitable pharmaceutical carrier, and via a suitable route of administration, including for example, but not limited to, the oral route, buccal route, rectal route, parenteral route, intraperitoneal route, intramuscular route, ophthalmic route, dermal route, and inhalation route, to name a few. A pharmaceutical carrier is any acceptable known pharmaceutical vehicle, for example, but not limited to, water, saline, dextrose, or sucrose, to name a few.

The present invention provides a compound of Formula I:

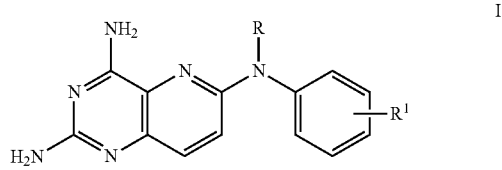

wherein R is H, a methyl group, an ethyl group, a n-propyl group, an iso-propyl group, or a n-butyl group; and $R^1$ is H, a 4'-methyl group, a 4'-OH, a 4'-OMe group, a 2',3'-$C_2H_4$ group, a; 3',4'-$C_2H_4$ group, a 3',4'-diF, a 3',4',5'-triF, or a 4'-$OCF_3$; and optionally including a salt or a hydrate of said compound.

Another embodiment of this invention provides a pharmaceutical composition comprising a compound of Formula I and one or more acceptable pharmaceutical carriers.

Another embodiment of this invention provides a method of treating a patient having cancer comprising administering a therapeutically effective amount of a compound of Formula I, or a pharmaceutical composition comprising a compound of Formula I and one or more acceptable pharmaceutical carriers to the patient.

Another embodiment of this invention provides a compound of Formula V:

V

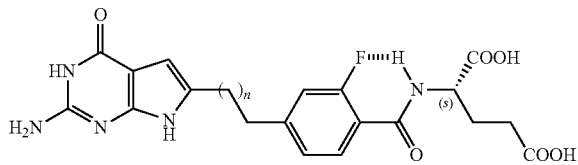

wherein n is 3; and optionally including a salt or a hydrate of said compound.

Another embodiment of this invention provides a pharmaceutical composition comprising a compound of Formula V and one or more acceptable pharmaceutical carriers.

Another embodiment of this invention provides a method of treating a patient having cancer comprising administering a therapeutically effective amount of a compound of Formula V, or a pharmaceutical composition comprising a compound of Formula V and one or more acceptable pharmaceutical carriers to the patient.

Another embodiment of this invention provides a compound of Formula VI:

VI

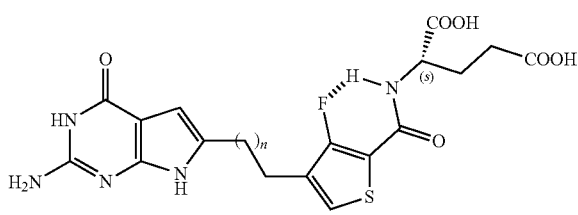

wherein n is 3; and optionally including a salt or a hydrate of said compound.

Another embodiment of this invention provides a pharmaceutical composition comprising a compound of Formula VI and one or more acceptable pharmaceutical carriers.

Another embodiment of this invention provides a method of treating a patient having cancer comprising administering a therapeutically effective amount of a compound of Formula VI, or a pharmaceutical composition comprising a compound of Formula VI and one or more acceptable pharmaceutical carriers to the patient.

Another embodiment of this invention provides a compound of Formula XXVI:

XXVI

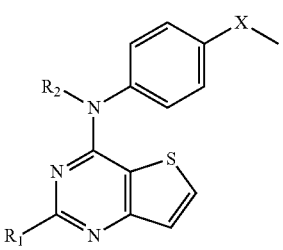

wherein X is O or S; $R_1$ is H or $CH_3$; and $R_2$ is H or $CH_3$, and optionally including a salt or a hydrate of said compound.

Another embodiment of this invention provides a pharmaceutical composition comprising a compound of Formula XXVI and one or more acceptable pharmaceutical carriers.

Another embodiment of this invention provides a method of treating a patient having cancer comprising administering a therapeutically effective amount of a compound of Formula XXVI, or a pharmaceutical composition comprising a compound of Formula XXVI and one or more acceptable pharmaceutical carriers to the patient.

Another embodiment of this invention provides a compound of Formula XXVII:

XXVII

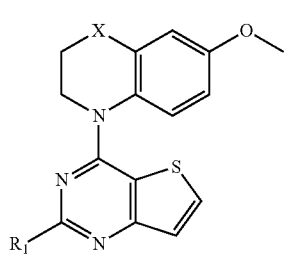

wherein X is $CH_2$ or O, and $R_1$ is H or $CH_3$, and optionally including a salt or a hydrate of said compound.

Another embodiment of this invention provides a pharmaceutical composition comprising a compound of Formula XXVII and one or more acceptable pharmaceutical carriers.

Another embodiment of this invention provides a method of treating a patient having cancer comprising administering a therapeutically effective amount of a compound of Formula XXVII, or a pharmaceutical composition comprising a compound of Formula XXVII and one or more acceptable pharmaceutical carriers to the patient.

Another embodiment of this invention provides a compound of Formula XXVIII:

XXVIII

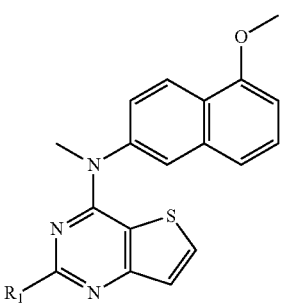

wherein $R_1$ is H or $CH_3$; and optionally including a salt or a hydrate of said compound.

Another embodiment of this invention provides a pharmaceutical composition comprising a compound of Formula XXVIII and one or more acceptable pharmaceutical carriers.

Another embodiment of this invention provides a method of treating a patient having cancer comprising administering a therapeutically effective amount of a compound of Formula XXVII, or a pharmaceutical composition comprising a compound of Formula XXVIII and one or more acceptable pharmaceutical carriers to the patient.

Another embodiment of this invention provides a compound of Formula XXIX:

XXIX

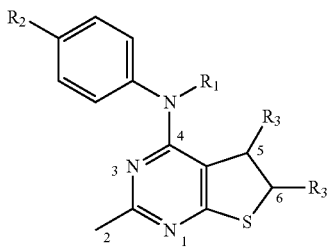

wherein R₁ is H or CH₃; R₂ is SCH₃ or OCH₃; and R₃ is H or CH₃; and optionally including a salt or a hydrate of said compound.

Another embodiment of this invention provides a pharmaceutical composition comprising a compound of Formula XXIX and one or more acceptable pharmaceutical carriers.

Another embodiment of this invention provides a method of treating a patient having cancer comprising administering a therapeutically effective amount of a compound of Formula XXIX, or a pharmaceutical composition comprising a compound of Formula XXIX and one or more acceptable pharmaceutical carriers to the patient.

Another embodiment of this invention provides a compound of Formula XXX:

XXX

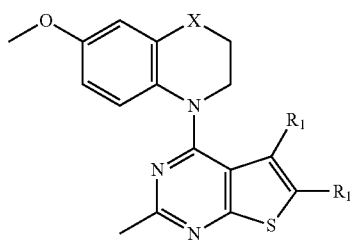

wherein X is CH₂ or O; and R₁ is H or CH₃; and optionally including a salt or a hydrate of said compound.

Another embodiment of this invention provides a pharmaceutical composition comprising a compound of Formula XXX and one or more acceptable pharmaceutical carriers.

Another embodiment of this invention provides a method of treating a patient having cancer comprising administering a therapeutically effective amount of a compound of Formula XXX, or a pharmaceutical composition comprising a compound of Formula XXX and one or more acceptable pharmaceutical carriers to the patient.

Another embodiment of this invention provides a compound of Formula XXXI:

XXXI

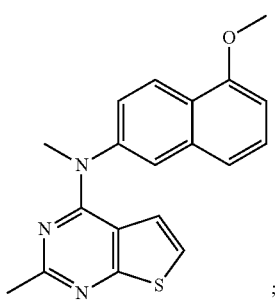

and optionally including a salt or a hydrate of said compound.

Another embodiment of this invention provides a pharmaceutical composition comprising a compound of Formula XXXI and one or more acceptable pharmaceutical carriers.

Another embodiment of this invention provides a method of treating a patient having cancer comprising administering a therapeutically effective amount of a compound of Formula XXXI, or a pharmaceutical composition comprising a compound of Formula XXXI and one or more acceptable pharmaceutical carriers to the patient.

Another embodiment of this invention provides a compound of Formula XXXII:

XXXII

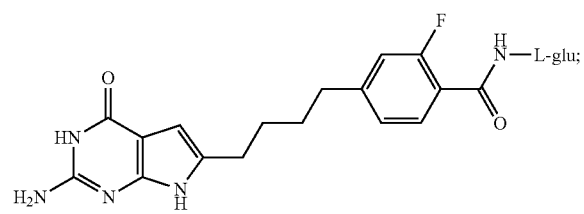

and optionally including a salt or a hydrate of said compound.

Another embodiment of this invention provides a pharmaceutical composition comprising a compound of Formula XXXII and one or more acceptable pharmaceutical carriers.

Another embodiment of this invention provides a method of treating a patient having cancer comprising administering a therapeutically effective amount of a compound of Formula XXXII, or a pharmaceutical composition comprising a compound of Formula XXXIIV and one or more acceptable pharmaceutical carriers to the patient.

Another embodiment of this invention provides a compound of Formula XXXIII:

XXXIII

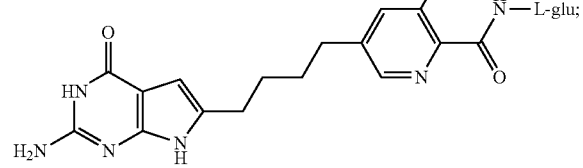

and optionally including a salt or a hydrate of said compound.

Another embodiment of this invention provides a pharmaceutical composition comprising a compound of Formula XXXIII and one or more acceptable pharmaceutical carriers.

Another embodiment of this invention provides a method of treating a patient having cancer comprising administering a therapeutically effective amount of a compound of Formula XXXIII, or a pharmaceutical composition comprising a compound of Formula XXXIII and one or more acceptable pharmaceutical carriers to the patient.

Another embodiment of this invention provides a compound of Formula XXXIV:

XXXIV

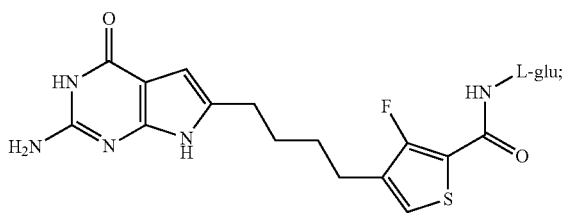

and optionally including a salt or a hydrate of said compound.

Another embodiment of this invention provides a pharmaceutical composition comprising a compound of Formula XXXIV and one or more acceptable pharmaceutical carriers.

Another embodiment of this invention provides a method of treating a patient having cancer comprising administering a therapeutically effective amount of a compound of Formula XXXIV, or a pharmaceutical composition comprising a compound of Formula XXXIV and one or more acceptable pharmaceutical carriers to the patient.

Another embodiment of this invention provides a compound of Formula IX:

IX

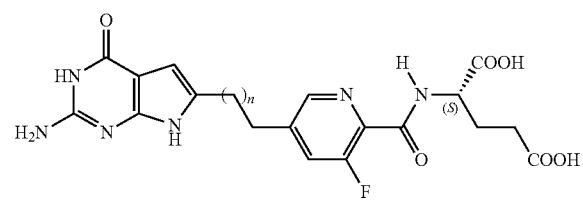

wherein n is 3; and optionally including a salt or a hydrate of said compound.

Another embodiment of this invention provides a pharmaceutical composition comprising a compound of Formula IX and one or more acceptable pharmaceutical carriers.

Another embodiment of this invention provides a method of treating a patient having cancer comprising administering a therapeutically effective amount of a compound of Formula IX, or a pharmaceutical composition comprising a compound of Formula IX and one or more acceptable pharmaceutical carriers to the patient.

Another embodiment of this invention provides a compound of the Formula XI:

XI

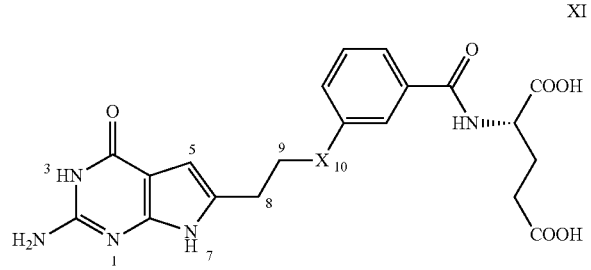

wherein X is $CH_2$, O, or NH; and optionally including a salt or a hydrate of said compound.

Another embodiment of this invention provides a pharmaceutical composition comprising a compound of Formula XI and one or more acceptable pharmaceutical carriers.

Another embodiment of this invention provides a method of treating a patient having cancer comprising administering a therapeutically effective amount of a compound of Formula XI, or a pharmaceutical composition comprising a compound of Formula XI and one or more acceptable pharmaceutical carriers to the patient.

Other embodiments of this invention include any one of the compounds of this invention as disclosed by the chemical formula set forth in the detailed description of this invention.

Other embodiments of this invention include methods of treating a patient having cancer comprising administering a therapeutically effective amount of any one or more of the compounds, or salts or hydrates of these compounds, of this invention as disclosed by the chemical formula set forth in the detailed description of this invention, or a pharmaceutical composition comprising any one or more of the compounds, or salts or hydrates of these compounds, of this invention as described in the detailed description of this invention and one or more acceptable pharmaceutical carriers, to the patient.

Section I: 6-Substituted Pyrido[3,2-D]Pyrimidines as Dihydrofolate Reductase Inhibitors and Potential Anti-Opportunistic Agents

*Pneumocystis jirovecii* (pj), *Toxoplasma gondii, Mycobacterium avium* and *M. intracellulare* are some of the most common organisms that cause life-threatening opportunistic infections in AIDS and other immunocompromised patients.[1] Despite the existence of the highly active antiretroviral therapy (HAART), the incidences of HIV cases persist due to non-adherence, toxicity arising from current treatments, emergence of drug resistant strains, late diagnosis of HIV and the rise in HIV cases in developing countries.[2] *Pneumocystis* pneumonia (PCP) was originally thought to be caused by the fungus *Pneumocystis carinii* (pc), but it is now known that the strain that is responsible for infecting humans is pj.[3-4] *P. carinii* is the strain that infects rats.[3]

Dihydrofolate reductase (DHFR) contributes to the de novo mitochondrial thymidylate biosynthesis pathway. DHFR catalyzes the reduction of 7,8-dihydrofolate to 5,6,7,8-tetrahydrofolate using NADPH as reductant. Due to the vital role of DHFR in the folate cycle as well as in thymidylate biosynthesis, the inhibition of DHFR leads to a "thymine-less cell death".[5] DHFR enzymes from pj (pjDHFR) and pc (pcDHFR) differ by 38% in amino acid sequence and exhibit different sensitivity to existing drugs.[4] No crystal structure of pjDHFR has been reported to date and known pcDHFR inhibitors act as poor surrogates for pjDHFR inhibition. In addition, difficulties in in-vitro cultures of pj outside of human lung and the lack of animal models have impeded the drug discovery efforts to obtain selective pjDHFR inhibitors.[6] Section I—FIG. 1 shows the structures of known dihydrofolate reductase inhibitors TMP and pyrimethamine (Section I—FIG. 1): first line therapy, are weak inhibitors of pjDHFR and must be co-administered with sulfonamides to compensate for their weak activities.1 However, combination therapy is successful only in 50-75% of the AIDS population and is limited due to severe side effects.[7,8] Trimetrexate (TMQ) and piritrexim (PTX) (FIG. 1): are potent, but non-selective DHFR inhibitors used in the treatment of moderate to severe PCP.[9] However, they cause high rates of myelosuppression and TMQ is co-administered with leucovorin (5-formyltetrahydrofolate) as a rescue agent to prevent host cell toxicity. 10 However, this dual therapy increases treatment cost and host cell rescue with leucovorin is not always successful.

Given the limitations of the existing regimen, it is highly desirable to develop single agent DHFR inhibitors that combine the potency of TMQ or PTX with the species selectivity of TMP and could also be co-administered sulfonamides and without leucovorin or used as immunotherapy for the treatment of pj infections.

Figure 2:
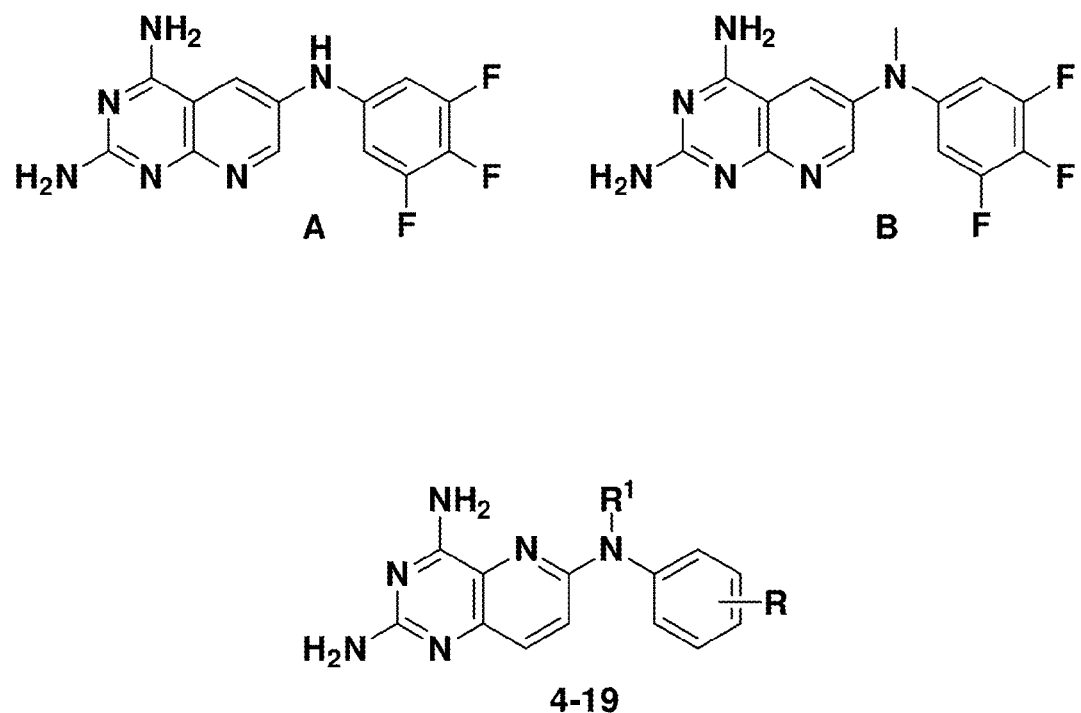
FIG. 2 (Section I—FIG. 2) shows chemical structures of the dihydrofolate reductase inhibitor compounds A, B, and 4-19, of this invention FIG. 3 (Section II—FIG. 1) shows the chemical structures of known microtubule targeting agents.

Section I—FIG. 2 shows the structures of novel dihydrofolate reductase inhibitors of this invention, namely, structures for compounds A, and B, and compounds 4-19.

Section I—

TABLE 1

Inhibitory concentrations (IC$_{50}$, in µM) against recombinant pjDHFR, hDHFR and selectivity ratio[a]

|   | R  | DHFR Pj (nM) | Human DHFR (nM) | Hu/Pj  |
|---|----|--------------|-----------------|--------|
| A | H  | 870          | 3100            | 3.5    |
| B | Me | 4.2          | 150             | 35     |
| TMP |  | 92           | 24.5            | 266.30 |
| PTX |  | 41           | 2               | 0.1    |

[a]These assays were carried out at 37° C. under 18 µM dihydrofolic acid concentration.

In 2013, Gangjee et al[11] reported a series of pyrido[2,3-d]pyrimidine analogues as potent and selective inhibitors of pjDHFR. In this series compound B (Section I—Figure 2), displayed a 35-fold higher selectivity (hDHFR/pjDHFR) compared to clinically used TMQ (0.1-fold selective).

N-7 methylation from A to B led to an increase in selectivity by 10-fold and potency by 200-fold due to formation of a hydrogen bond with Isoleucine123 in pjDHFR compared with Valine 115 in hDHFR.

Nitrogen atom of pyrido[2,3-d]pyrimidines is exposed to a hydrophobic environment in the pocket, whereas pyrido[3,2-d]pyrimidines has nitrogen atom exposed to a significantly more polar environment. This could enforce stronger binding in proposed pyrido[3,2-d] pyrimidines.

To further explore the structure activity relationship (SAR), substituted pyrido[3,2-d]pyrimidines were synthesized to evaluate the potency and selectivity against pjDHFR and other pathogen DHFR.

Scheme 1. Synthesis of 4-18.

Previous methods:

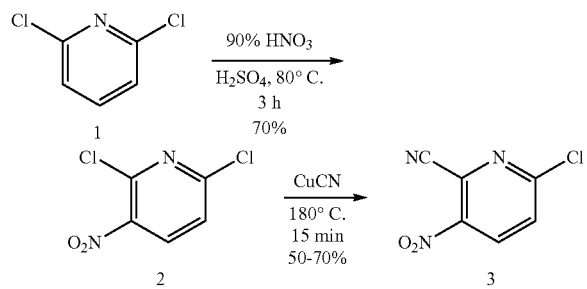

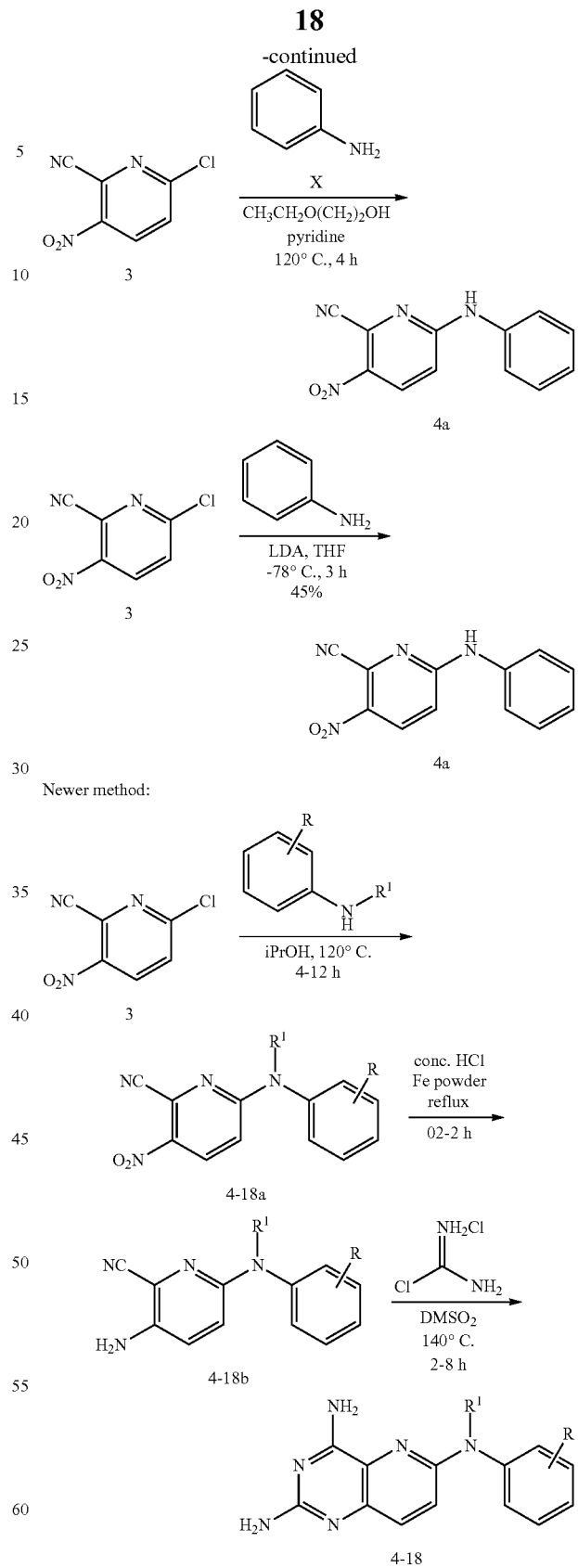

Prior synthesis[13] of pyrido[3,2-d]pyrimidines utilized ethoxyethanol and aniline for substitution on 3 (Scheme 1) whereas for substituted anilines, strong bases such as LDA were used to facilitate the reaction. Both methods suffer from long durations and stringent reaction conditions, respectively. A simpler and versatile synthetic route to obtain 4-18 from 3 was envisioned using appropriate anilines at reflux in isopropanol at 120° C., a highly versatile reaction process that provided good yields (75-83%). Reduction of the nitro group was performed using iron in conc. HCl (Bechamp reduction) or using $H_2$/Pd to give quantitative yields. Cyclization of the resultant intermediate with chlorformamidine in dimethylsulfone at 140° C. provided the desired target compounds.

Section I—Table 2:

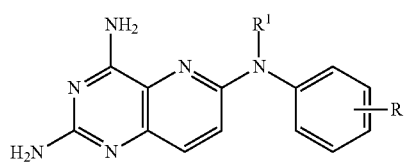

TABLE 2

Overall reaction yields (over 3 steps) for 4-18

| | $R^1$ | R | Yield (over 3 steps) (%) |
|---|---|---|---|
| 4 | H | H | 60 |
| 5 | H | 4'-Me | 50 |
| 6* | H | 4'-OH | 17 |
| 7* | H | 4'-OMe | 13 |
| 8 | H | 2',3'-$C_2H_4$ | 51 |
| 9 | H | 3',4'-$C_2H_4$ | 64 |
| 10 | H | 3',4'-diF | 43 |
| 11 | H | 3',4',5'-triF | 69 |
| 12 | H | 4'-$OCF_3$ | 42 |
| 13 | Me | H | 38 |
| 14 | Et | H | 34 |
| 15 | n-Pr | H | 65 |
| 16 | i-Pr | H | 32 |
| 17 | n-Bu | H | 77 |
| 18 | Me | 4'-$OCF_3$ | 38 |

*Compound 7 was obtained as a side-product from the synthesis of 6.

Section I—Table 3:

TABLE 3

Inhibitory concentrations ($IC_{50}$, in μM) against recombinant pjDHFR, hDHFR and selectivity ratio[a]

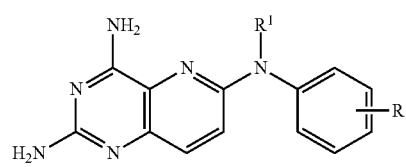

4-19

| | R' | R | DHFR Pj (nM) | Human DHFR (nM) | Hu/Pj |
|---|---|---|---|---|---|
| 4 | H | H | 122 | 1526 | 12.5 |
| 5 | H | 4'-Me | 174 | 1576 | 15.1 |
| 6 | H | 4'-OH | 150 | 2459 | 10.5 |
| 7 | H | 4'-OMe | 239 | 1098 | 10.3 |
| 8 | H | 2',3'-$C_2H_4$ | 112 | 3185 | 9.8 |
| 9 | H | 3'4'-$C_2H_4$ | 275 | 1808 | 11.6 |
| 10 | H | 3'4'-diF | 155 | 2253 | 11.7 |
| 11 | H | 3',4',5'-triF | 80 | 4125 | 28.2 |
| 12 | H | 4'-$OCF_3$ | 194 | 4125 | 21.3 |
| 13 | Me | H | 96 | 942 | 9.8 |
| 14 | Et | H | 150 | 1571 | 10.5 |
| 15 | n-Pr | H | 123 | 1338 | 10.9 |
| 16 | i-Pr | H | 201 | 1373 | 6.8 |
| 17 | n-Bu | H | 66 | 903 | 13.6 |
| 18 | Me | 4'-$OCF_3$ | 13 | 153 | 11.7 |
| A | H | 3',4',5'-triF | 870 | 3100 | 3.5 |
| TMP | — | — | 92 | 24500 | 266.3 |
| PTX | — | — | 41 | 2 | 0.1 |

[a]These assays were carried out at 37° C. under 18 μM dihydrofolic acid concentration.

Another embodiment of this invention provides a method of treating a patient having cancer comprising administering to a patient an effective amount of a compound comprising any one of the chemical structures and formulae set forth in the attached specification, A preferred embodiment of this invention comprises administering an effective amount of a salt or a hydrate of one of said compounds.

Section I—References

1. Kaplan, J. E.; Benson, C.; Holmes, K. H.; Brooks, J. T.; Pau, A.; Masur, H. Centers for Disease Control and Prevention (CDC); National Institutes of Health; HIV Medicine Association of the Infectious Diseases Society of America: Guidelines for prevention and treatment of opportunistic infections in HIV-infected adults and adolescents: recommendations from CDC, the National Institutes of Health, and the HIV Medicine Association of the Infectious Diseases Society of America. *MMWR Recomm. Rep.* 2009, 58, 1-207.

2. a) Catherinot, E.; Lanternier, F.; Bougnoux, M. E.; Lecuit, M. Couderc, L. J.; Lortholary, O. Pneumocystis jirovecii pneumonia. *Infect. Dis. Clin. N. Am.* 2010, 24, 107-138. b) Ong, E. L. C. Common AIDS-Associated Opportunistic Infections. *Clinical Medicine* 2008, 8, 539-543. c) Kelly, M. N.; Shellito, J. E. Current understanding of Pneumocystis immunology. *Future Microbiol.* 2010, 5, 43-65. d) Huang, L.; Crothers, K. HIV-Associated Opportunistic Pneumonias. *Respirology,* 2009, 14, 474-485. e) Huovinen, P. Resistance to trimethoprim-sulfamethoxazole. *Clin. Infect. Dis.* 2001, 32, 1608-1614.

3. a) Gangjee, A.; Kurup, S.; Namjoshi, O. Dihydrofolate reductase as a target for chemotherapy in parasites. *Curr. Pharm. Des.* 2007, 13, 609-639. b) Ma, L.; Kovacs, J. A. Expression and characterization of recombinant human-derived Pneumocystis carinii dihydrofolate reductase. *Antimicrob. Agents Chemother.* 2000, 44, 3092-3096.

4. Cody, V.; Chisum, K.; Pope, C.; Queener, S. F. Purification and characterization of human-derived Pneumocystis jirovecii dihydrofolate reductase expressed in Sf21 insect cells and in Escherichia coli. *Protein Expr. Purif.* 2005, 40, 417-423.

5. MacKenzie, R. E. Biogenesis and interconversion of substituted tetrahydrofolates. in *Folates and Pterins Chemistry and Biochemistry*; Blakley, R. L., Benkovic, S. J., Eds.; Wiley: New York, 1984; Vol. 1, 255-306.
6. Thomas, C. F.; Limper, A. H. Current insights into the biology and pathogenesis of *Pneumocystis Pneumonia*. *Nat. Rev. Microbio.* 2007, 5, 298-308.
7. Klepser, M. E.; Klepser, T. B. Drug treatment of HIV-related opportunistic infections. *Drugs* 1997, 53, 40-73.
8. a) Roudier, C.; Caumes, E.; Rogeaux, O.; Bricaire, F.; Gentilini M. Adverse cutaneous reactions to trimethoprim-sulfamethoxazole in patients with the acquired immunodeficiency syndrome and *Pneumocystis carinii* pneumonia. *Arch. Dermatol.* 1994, 130, 1383-1386.
9. Allegra, C. J.; Kovacs, J. A.; Drake, J. C.; Swan, J. C.; Chabner, B. A.; Masur, H. Activity of antifolates against *Pneumocystis carinii* dihydrofolate reductase and identification of a potent new agent. *J. Exp. Med.* 1987, 165, 926-931.
10. a) Sattler, F. R.; Frame, P.; Davis, R.; Nichols, L.; Shelton, B.; Akil, B.; Baughman, R.; Hughlett, C.; Weiss, W.; Boylen, C. T.; van der Horst, C.; Black, J.; Powderly, W.; Steigbigel, R. T.; Leedom, J. M.; Masur, H.; Feinberg, J. Trimetrexate with leucovorin versus trimethoprim-sulfamethoxazole for moderate to severe episodes of *Pneumocystis carinii* pneumonia in patients with AIDS: a prospective, controlled multicenter investigation of the AIDS Clinical Trials Group Protocol 029/031. *J. Infect. Dis.* 1994, 170, 165-172. b) Masur, H.; Polis, M. A.; Tuazon, C. U.; Ogata-Arakaki, D.; Kovacs, J. A.; Katz, D.; Hilt, D.; Simmons, T.; Feuerstein, I.; Lundgren, B.; Lane, H. C.; Chabner, B. A.; Allegra, C. J. Salvage trial of trimetrexate-leucovorin for the treatment of cerebral toxoplasmosis in patients with AIDS. *J. Infect. Dis.* 1993, 167, 1422-1426.
11. Gangjee, A.; Namjoshi, O.; Raghavan, S.; Queener, S.; Kisluik, R.; Cody, V. Design, Synthesis, and Molecular Modeling of Novel Pyrido[2,3-d]pyrimidine Analogues As Antifolates; Application of Buchwald-Hartwig Aminations of Heterocycles. *J. Med. Chem.* 2013, 56 (11), 4422-4441.
12. Molecular Operating Environment (MOE), 2014.09; Chemical Computing Group Inc., 1010 Sherbooke St. West, Suite #910, Montreal, QC, Canada, H3A 2R7, 2014.
13. Gangjee, A.; Zhu, Y.; Queener, S. 6-Substituted 2,4-Diaminopyrido[3,2-d]pyrimidine Analogues of Piritrexim as Inhibitors of Dihydrofolate Reductase from Rat Liver, *Pneumocystis carinii*, and *Toxoplasma gondii* and as Antitumor Agents. *J. Med. Chem.*, 1998, 41 (23), 4533-4541.

Section II—Pyrrolo (2,3-d)pyrimidines as Tubulin Inhibitors

Microtubules are key components of the cell and are involved in maintenance of cell shape and cell division. Small molecule inhibitors targeting microtubules arrest the cell cycle progression by interfering with mitotic spindle assembly. Currently available microtubule assembly inhibitors including paclitaxel have major limitations against multidrug resistance (MDR) tumors. Overexpression of P-glycoprotein (Pgp) and/or βIII-tubulin can severely limit their clinical utility as cancer chemotherapeutic agents. Recently, we reported pyrrolo[2,3-d]pyrimidines with the N-methyl-4'-methoxyaniline moiety at the 4-position that overcome clinically relevant mechanisms of drug resistance. In this study, a series of bicyclic pyrrolo[2,3-d]pyrimidines were designed and synthesized to explore further the SAR at the 4-position of the pyrrolopyrimidine scaffold. The chloro moiety of the 4-chloro-2-methyl-7H-pyrrolo[2,3-d]pyrimidine was replaced with various anilines. The structure-activity relationship and the in vitro evaluations of these agents with respect to their abilities to disrupt cellular microtubules and tumor cell inhibitory activities is set forth herein.

Introduction

Microtubules are dynamic filamentous polymers of αβ-tubulin heterodimers in cells and play a role in fundamental cellular processes such as cell division, formation and maintenance of cell shape, motility, cell signaling, secretion, and intracellular transport. In a recent report[1], it was revealed that microtubule targeting agents (MTAs) inhibit a majority of human tumors by interfering with essential interphase functions such as microtubule trafficking. Thus attacking microtubules is an attractive target for anticancer agents. An overly simplistic classification of MTAs includes microtubule-stabilizing agents or polymerizing agents (exemplified by taxanes) and microtubule destabilizing agents (exemplified by the vincas).[2] Taxanes bind to the interior of the microtubule on β-tubulin. In contrast, the vinca alkaloids also bind to β tubulin but at a site distinct from that of taxoids. Recently, the colchicine domain binding agent, combretastatin A-4P (CA4P) was advanced to clinical trials.[3] The colchicine site is primarily on β-tubulin at its interface with the α-subunit of the same tubulin heterodimer. Interfering with microtubule polymerization has been a viable strategy for the development of highly successful antitumor drug classes. Section II—FIG. 1 show structures of microtubule targeting agents. Section II—FIG. 2, shows the chemical structure of a lead compound 1, and the target compounds 2-7 of this invention.

Mutations in the p53 gene account for almost 50% of human tumors, and the most effective drugs in p53-mutant cell lines are tubulin-binding agents.[4] This further highlights the importance of developing novel tubulin-binding drugs that are active against resistant tumors. Despite the unprecedented success of MTAs in cancer chemotherapy, multidrug resistance (MDR) is a major limitation. Overexpression of P-glycoprotein (Pgp) has been reported in the clinical setting in several tumor types, particularly after patients have received chemotherapy.[6] Moreover, Pgp expression may act as a prognostic indicator in certain cancers and is associated with poor response to chemotherapy by inducing resistance in the presence of cytotoxic drug.[6] Another clinical mechanism of resistance to tubulin-binding drugs is the overexpression of specific isotypes of β-tubulin, particularly βIII-tubulin.[5] The overexpression of βIII-tubulin in multiple tumor types, including breast, ovarian and non-small cell lung cancers,[6] is involved in resistance to taxanes and vinca alkaloids. Thus analogs that are potent MTAs and overcome the resistance mechanisms to currently used MTAs are highly prized.

Rationale

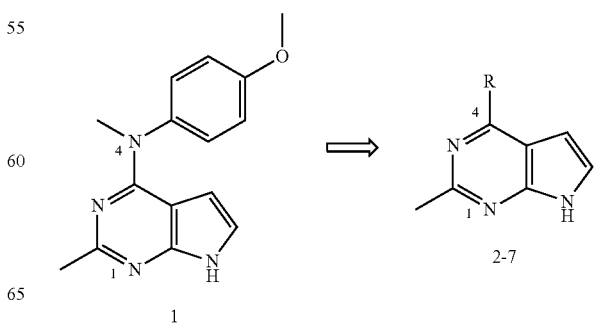

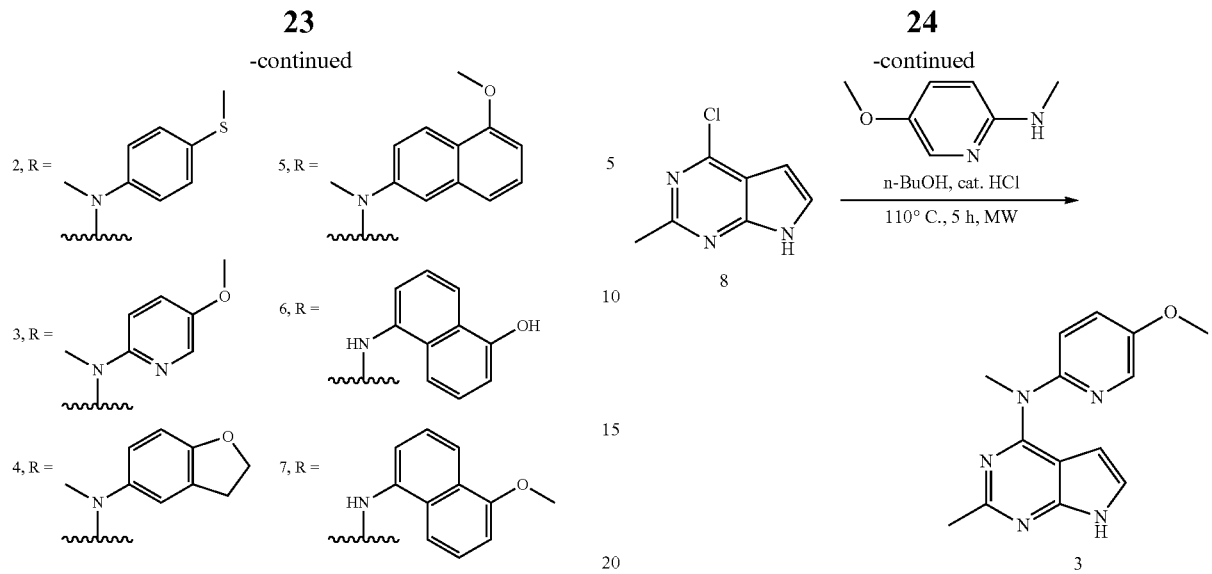

A lead compound 1 and target compounds 2-7 of this invention.

Gangjee et al.[7] reported compound 1 with the N-methyl-4'-methoxyaniline moiety at the 4-position as a potent microtubule depolymerizing agent (Section II—FIG. 2). This compound inhibits the growth of tumor cells with $IC_{50}$ values in the submicromolar range and also circumvents the Pgp and βIII-tubulin resistance mechanisms that limit the activity of MTAs. This finding prompted a structure-activity relationship (SAR study), and this report addresses the effect of variation of the N-methyl-4'-methoxyaniline moiety of 1 with various mono- and bicyclic amines in the 4-position of the pyrrolo[2,3-d]pyrimidine ring of 1.

Analogs 2-7 were synthesized and evaluated for their biological activity in microtubule depolymerization assay and antiproliferative assay as well as against cell lines overexpressing the multidrug resistance proteins Pgp and βIII-tubulin. Tumors with Pgp and βIII-tubulin impart significant resistance to several antitubulin agents, including paclitaxel, vincristine and vinblastine.

Chemistry

Compounds 2-7 were synthesized as described in Scheme 1-Section II.

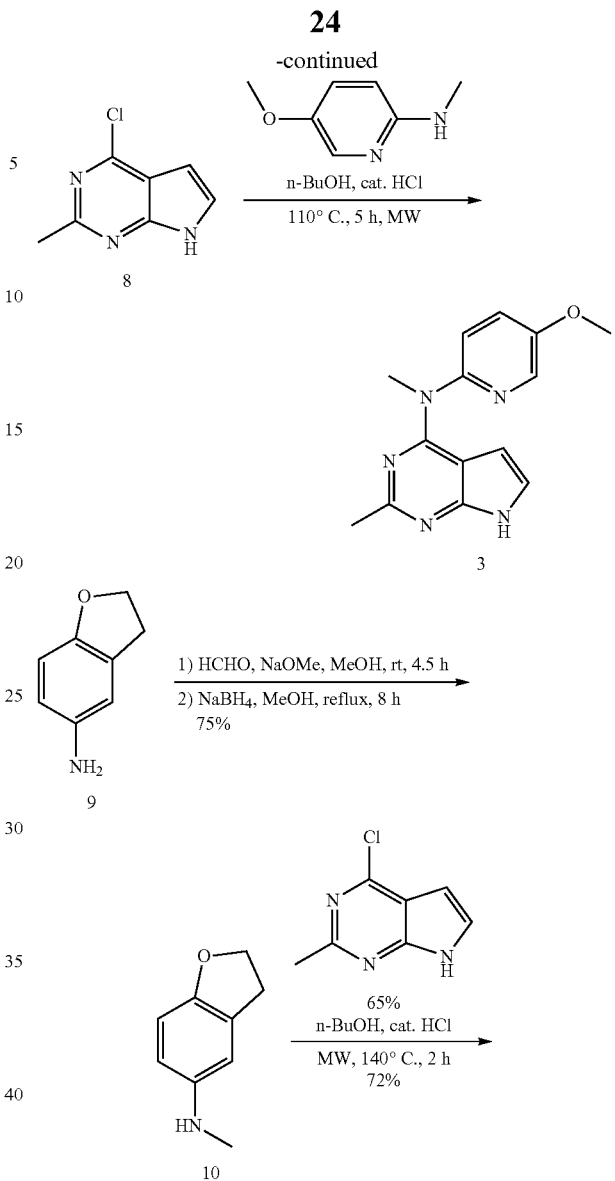

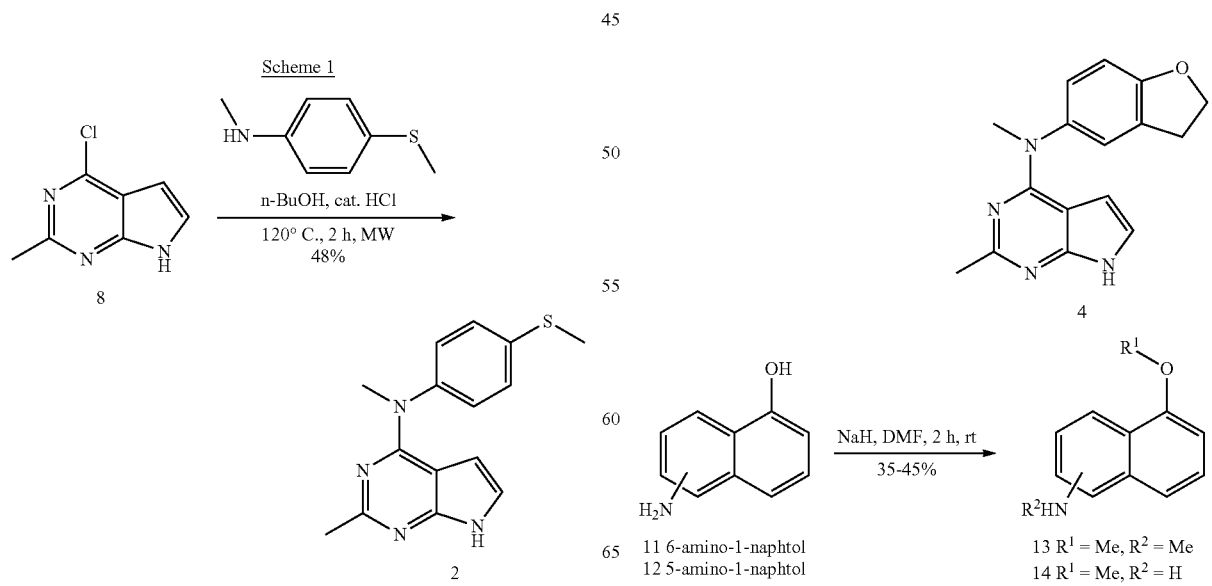

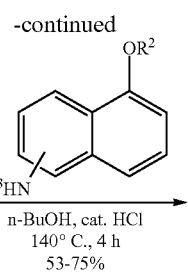

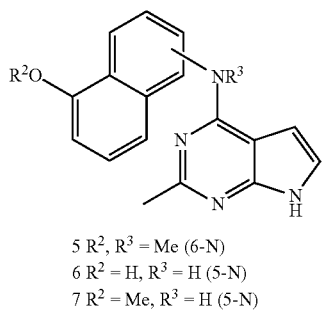

5 R², R³ = Me (6-N)
6 R² = H, R³ = H (5-N)
7 R² = Me, R³ = H (5-N)

Aniline 9 was methylated using a suspension of sodium methoxide and formaldehyde in methanol and stirred for 4.5 h. Sodium borohydride was then added, and the solution kept at reflux for 2 h to afford compound 10 in 75% yield. Amino-napthols 11 and 12 were methylated using sodium hydride in the presence of DMF as solvent to yield 13 and 14 respectively. 4-Chloro-2-methyl-7H-pyrrolo[2,3-d]pyrimidine 8 (Scheme 1) was then subjected to nucleophilic displacement with appropriate aryl amines and a catalytic amount of concentrated HCl in the presence of butanol to yield final compounds 2-7 in 48-75% yield.

Biological Activity

Section II—

TABLE 1

Biological activities

| Compd. | MDA-MB-435 $IC_{50}$ ± SD (nM) | Microtubule depolymerization (A-10 cells) $EC_{50}$ ± SD (μM) |
|---|---|---|
| CA4 | 3.4 ± 0.6 | 13 nM |
| 1 | 183 ± 3 | 5.8 |
| 2 | 198 ± 23 | 8.1 |
| 3 | ND | >10 |
| 4 | 550 ± 86 | 8 |
| 5 | 37.1 ± 9.4 | 365 |
| 6 | ND | >10 |
| 7 | ND | >10 |

ND—not determined

Evaluation of Microtubule Targeting and Antiproliferative Effects.

Compounds 2-7 were evaluated for antiproliferative activity against the drug-sensitive MDA-MB-435 cancer cells in culture using the sulforhodamine B assay (SRB assay), and $IC_{50}$ values (concentration required to cause 50% inhibition of proliferation) were calculated (Table 1). The $EC_{50}$ (concentration required to cause 50% loss of cellular microtubules) was also determined. Bioisosteric replacement of the 4'-methoxy of the lead 1 with a 4'-thiomethyl moiety afforded 2 that retained potency in the antiproliferative assay and was only 1.4-fold less potent against microtubule depolymerization than lead compound 1. The electron poor 4'-methoxypyridine moiety in place of 4'-methoxyaniline moiety in compound 3 was detrimental to both antiproliferative activity and cellular microtubule loss which indicates that the pyridine ring is detrimental for activity. A fused bicyclic 4-N-methyl-2'-3'-dihydrobenzofuran moiety at the 4-position (4) of 2-methyl-7H-pyrrolo[2,3-d]pyrimidine was tolerated, albeit with a 3-fold less potent antiproliferative effect and 1.4-fold less potent depolymerizing effect than 1 indicating that conformational restriction of the $OCH_3$ moiety of 1 in a dihydrofuran ring is not conducive to potent activity. Compound 5 with a bulky 5'-methoxy-N-methyl-2-naphthalenamine moiety at the 4-position was found to have a 5-fold increase in potency for antiproliferative effects and a 16-fold increase in potency in cellular microtubule depolymerization activity compared to 1. Napthols 6 and 7 were found to be inactive which indicates that both the 4'-methoxy and the 4-N-methyl are necessary for the activity.

Molecular Modeling

Compounds 3 and 5 were docked in the colchicine site as lead compound 1 binds at the colchicine site of tubulin (70% inhibition of colchicine binding at 5 μM concentration).[7] Reason for the loss of potency of 3 could be explained by the loss of hydrophobic interactions as the polar pyridine ring of 3 lies in the hydrophobic part of the site. On the contrary, 5 provided extra hydrophobic bulk in the unfilled hydrophobic region of binding site (interactions with Leu242, Val 238, Ile318) and improved activity significantly.

Section II—

TABLE 2

Compounds 1, 2 and 4 circumvent clinically relevant models of drug resistance

| | Effect of Pgp on drug sensitivity[b] $IC_{50}$ + SD (nM) | | | Effect of βIII-tubulin on drug sensitivity[c] $IC_{50}$ + SD (nM) | | |
|---|---|---|---|---|---|---|
| Compd. | SK-OV-3 | SK-OV-3 MDR-1-6/6 | Rr[a] | HeLa | WT βIII | Rr[a] |
| paclitaxel | 3.0 ± 0.06 | 2600 ± 270 | 864 | 1.6 ± 0.2 | 7.7 ± 0.2 | 4.7 |
| CA4 | 4.5 ± 0.2 | 6.6 ± 1.3 | 1.5 | 4.7 ± 0.2 | 5.7 ± 0.4 | 1.2 |
| 1 | 278 ± 19 | 435 ± 33 | 1.6 | 270 ± 26 | 186 ± 21 | 0.7 |

TABLE 2-continued

Compounds 1, 2 and 4 circumvent clinically relevant models of drug resistance

| Compd. | Effect of Pgp on drug sensitivity[b] $IC_{50}$ + SD (nM) | | | Effect of βIII-tubulin on drug sensitivity[c] $IC_{50}$ + SD (nM) | | |
|---|---|---|---|---|---|---|
| | SK-OV-3 | SK-OV-3 MDR-1-6/6 | Rr[a] | HeLa | WT βIII | Rr[a] |
| 2 | 253 ± 23 | 438 ± 58 | 1.7 | 186 ± 19 | 152 ± 14 | 0.8 |
| 4 | 779 ± 47 | 1600 ± 0.10 | 2.1 | 545 ± 53 | 620 ± 49 | 1.1 |

[a]Rr: Relative resistance.
[b]Antiproliferative effects of 1, 2 and 4 in parental and MDR-1-transducted cell lines in comparison with other microtubule disrupting agents. The $IC_{50}$ values were determined using the SRB assay (n = 3 ( SD). The Rr was calculated by dividing the $IC_{50}$ of the Pgp overexpressing cell line by the $IC_{50}$ of the parental cell line.
[c]Effects of the expression of βIII-tubulin on the sensitivity of cell lines to microtubule-targeting agents. The Rr was calculated by dividing the $IC_{50}$ of the WT βIII cell line by the $IC_{50}$ of the parental HeLa cells The ability of 2 and 4 to circumvent Pgp-mediated drug resistance was evaluated using an SK-OV-3 isogenic cell line pair (Table 2). In this cell line pair, the relative resistance (Rr) of paclitaxel is 864 while Rr values of 1.7-2.1 were obtained with 2 and 4, consistent with the Rr value obtained with CA4 of 1.5. These data suggest that 2 and 4 are poor substrates for transport by Pgp and thus could have the ability to circumvent resistance over some clinically useful MTAs like paclitaxel. A second clinically relevant mechanism of drug resistance to these microtubule agents is the expression of βIII isotype of tubulin. An isogenic HeLa cell line pair was used to study the effects of βIII tubulin on the potency of 2 and 4 (Section II—Table 2). The WT βIII cell line was generated from HeLa cells transfected with the gene for βIII-tubulin. Compounds 2 and 4 have Rr values that range from 0.8-1.1, suggesting that these compounds overcome drug resistance mediated by βIII-tubulin as compared with paclitaxel, which has a Rr of 4.7 in these cell lines. Thus compounds 2 and 4 inhibit the proliferation of human cancer cells without regard to their expression of Pgp or βIII-tubulin and are lead compounds for further structural modification to optimize activity.

Pyrrolo(2,3-d)pyrimidines as tubulin inhibitors

AG241

RM/AG/169-222

AG300

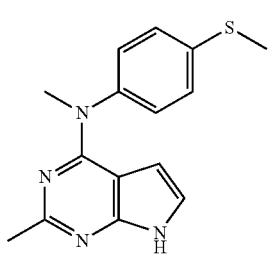

RM/AG/169-249

-continued

AG250

RM/AG/169-228

AG346

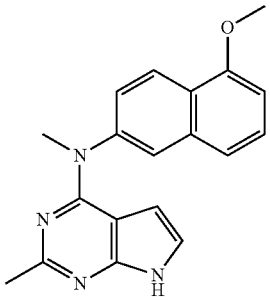

RM/AG/169-295

AG305

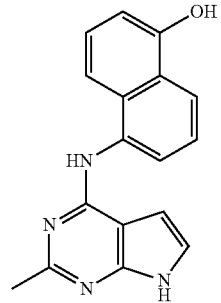

RM/AG/169-259

-continued

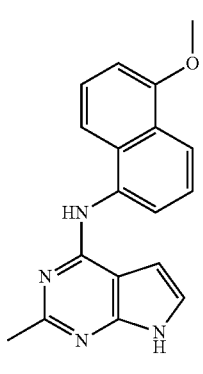

AG307

RM/AG/169-275

Summary

In summary, compounds 2-7 were synthesized and evaluated, and SAR for substitution at the 4-position of 2-methyl-7H-pyrrolo[2,3-d]pyrimidine was studied. Compounds 2, 4 and 7 were found to have microtubule depolymerization effects as well as antiproliferative actions. In addition, 2 and 4 overcome two clinically important tumor resistance mechanisms that limit activity of microtubule targeting agents, expression of Pgp and βIII-tubulin. However, these modifications in 2-7 afford analogs less potent than CA4. Further structural changes are currently underway to improve the potency.

Section II—References:
1. Komlodi-Pasztor, E.; Sackett D.; Wilkerson J.; Fojo T. Mitosis is not a key target of microtubule agents in patient tumors. Nat. Rev. Clin. Oncol. 2011, 8, 244-250.
2. Dumontet, C.; Jordan, M. A. Microtubule-binding agents: A dynamic field of cancer therapeutics. Nat. Rev. Drug Discov. 2010, 9, 790-803.
3. Massarotti, A.; Coluccia, A.; Silvestri, R.; Sorba, G.; Brancale, A. The Tubulin Colchicine Domain: a Molecular Modeling Perspective. Chem Med Chem. 2012, 7, 33-42.
4. Fojo, A. T.; Menefee, M. Microtubule targeting agents: Basic mechanisms of multidrug resistance (MDR). Semin. Oncol. 2005, 32, S3-S8
5. McCarroll, J. A.; Gan, P. P.; Liu, M.; Kavallaris, M. βIII-Tubulin is a multifunctional protein involved in drug sensitivity and tumorigenesis in non-small cell lung cancer. Cancer Res. 2010, 70, 4995-5003.
6. Chiou, J. F.; Liang, J. A.; Hsu, W. H.; Wang, J. J.; Ho, S. T.; Kao, A. Comparing the relationship of taxol-based chemotherapy response with P-glycoprotein and lung resistance-related protein expression in non-small cell lung cancer. Lung 2003, 181, 267-273.
7. Gangjee, A.; Zhao, Y.; Lin, L.; Raghavan, S.; Roberts, E. G.; Risinger, A. L.; Hamel, E.; Mooberry, S. L. Synthesis and Discovery of Water-Soluble Microtubule Targeting Agents that Bind to the Colchicine Site on Tubulin and Circumvent Pgp Mediated Resistance. J. Med. Chem. 2010, 53, 8116-8128.

Section III: Antifolate Compounds

The two major obstacles in cancer chemotherapy are toxicity due to non-selective uptake and tumor resistance of clinically used antifolates including pemetrexed (PMX). Currently marketed antifolates suffer from dose-limiting toxicity due to their transport by the ubiquitously expressed reduced folate carrier (RFC). We have reported a series of 6-substituted pyrrolo[2,3-d]pyrimidine classical antifolates that are selectively taken up by folate receptors (FR) and inhibit FR expressing tumor cells (KB and IGROV1) at sub-nanomolar $IC_{50}$ values. The target enzyme inhibited was glycinamide ribonucleotide formyl transferase (GARFTase) in purine bio-synthesis. As an extension of the SAR, we now explore the role of conformational restriction in the glutamate sidechain induced by designed intramolecular hydrogen bonding, for increased selectivity and potential multiple-enzyme inhibitory activity. A series of classical 6-substituted pyrrolo[2,3-d]pyrimidines with a variety of hydrogen bonding substituents on the side chain (het)aromatic ring, were designed and synthesized that resulted in increased potency and selectivity for target enzymes and tumor cells. The synthesis and in vitro evaluation of these compounds as substrates for folate transporters—RFC, FR and the proton coupled folate transporter (PCFT) and as inhibitors of KB tumor cells ($IC_{50}$) due to inhibition of one or more of the following, GARFTase, aminoimidazole carboxamide ribonucleotide formyl transferase (AICARFTase), thymidylate synthase (TS) and dihydrofolate reductase (DHFR) enzymes, will be set forth herein.

Introduction:

Folates are essential dietary vitamins vital for growth and regeneration of cells and tissue. Classical antifolates act as antiproliferative agents by inhibiting the uptake via transporters and utility of folates for DNA synthesis. The lack of de novo synthesis of folates, in mammals, requires transporters for uptake of folates from the diet. There are three major folate transporter systems: (1) The reduced folate carrier (RFC or SLC19A1) is, the main transporter of folates and antifolates. It is ubiquitously expressed and functions as anion anti-porter.[7] Antifolate uptake by RFC results in dose-limiting toxicity; (2) Folate receptors (FRs) α and β transport folates by endocytosis.[3] Since FRs show restricted tissue distribution compared to RFC, and are overexpressed by several tumor cells, FR-selective therapeutics have been designed to selectively target tumor cells that overexpress FRs; (3) The proton coupled folate transporter (PCFT; SLC46A1) is a proton symporter that transports folates/antifolates optimally at acidic pH.[4-6] Design of PCFT selective antifolates finds application in selectively targeting solid tumors that exist in acidic microenvironment.

Fluorine finds a wide range of applications in drug design and development and in medicinal chemistry due to the unique properties associated with it. Introducing a fluorine into a molecule can productively affect pKa, membrane permeability, conformation, potency, pharmacokinetic properties and metabolic pathways.[11] In the current study, we analyze the effects of strategic incorporation of fluorine via an induced intramolecular hydrogen bonding on our previously published tumor selective potent antifolates. Section III—FIG. 1 shows the structures of clinically used antifolates.

The folate-dependent biosynthetic pathways and their inhibition by antifolates include: (1) dihydrofolate reductase (DHFR), involved in the synthesis of purines and pyrimidines and a principle target of MTX; (2) thymidylate synthase (TS), involved in the synthesis of pyrimidines and inhibited by RTX and PMX; and (3) β-glycinamide ribonucleotide formyl transferase (GARFTase) and (4) 5-aminoimidazole-4-carboxamide ribonucleotide formyl transferase (AICARftase) which are involved in de novo purine synthesis and are secondary enzyme targets for PMX (Section III—FIG. 1).[8-9]

A major obstacle in cancer chemotherapy is the dose-limiting toxicity of all the clinically available antifolates (Section III—FIG. 1). These are all transported by the ubiquitously expressed RFC.[8-9] Thus it is of interest to design targeted antifolates that are selectively taken up by FRs and/or PCFT that are expressed by several tumors, over RFC. Additionally, enzyme-resistance towards antifolates in tumors can potentially be circumvented by designing single agent drugs that inhibit more than one folate metabolizing enzyme in both the purine and pyrimidine pathways. We previously reported targeted antifolates that are selectively transported by FRα and FRβ and/or PCFT and inhibit GARFTase and/or AICARFTase. Our current study was to explore the role of intramolecular fluorine hydrogen bonding induced conformational restriction of the glutamic acid side chain in our previously reported non-fluorinated targeted antifolates[1-2] to improve their selective uptake via transporters and as multiple folate enzyme inhibitors (Section III—FIG. 2).

Antifolate Compounds of this Invention:

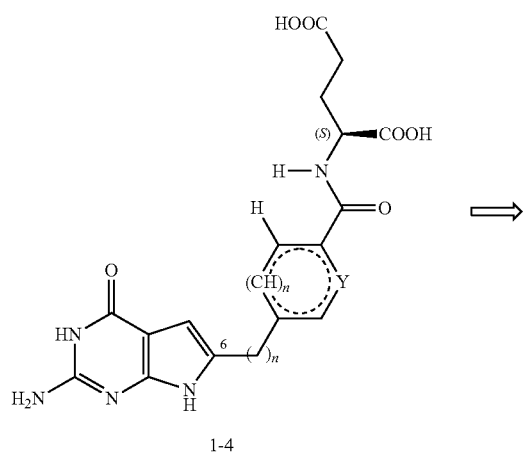

1-4 n = 3
n = 4
n = 1, Y = C, N
n = 0, Y = S

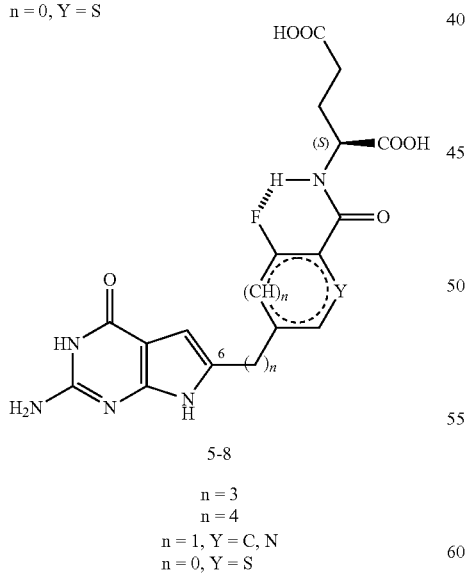

5-8 n = 3
n = 4
n = 1, Y = C, N
n = 0, Y = S

Section III—FIG. 2 shows the regioisomeric placement of the fluorine allows conformational restriction of the side chain (het) aromatic ring to explore the SAR of fluorine-hydrogen bond induced transporter uptake and purine biosynthesis enzyme inhibition.

We[1-2] previously reported a series of potent 6-substituted pyrrolo[2,3-d]pyrimidine antifolates that inhibit GARFTase in the de novo purine biosynthetic pathway via selective FR and/or PCFT uptake. Duch, et al.[10] observed that introduction of fluorine induced intramolecular fluorine-hydrogen bond with the side chain amide of L-glutamate improves potency in classical antifolates. In an attempt to improve the antitumor activity of our previous targeted analogs we synthesized and evaluated (Table 1) a series of 6-substituted pyrrolo[2,3-d]pyrimidines with possible side-chain conformational restriction through potential intramolecular fluorine hydrogen bonding forming a 6-membered ring (Section III—FIG. 2).[11] Introduction of strategically positioned fluorine also provides metabolic stability and conformational changes that alter the shape of the molecule for a better fit in the binding regions required for both selectivity in transport and potency at the enzyme.

Molecular Modeling

Molecular modeling was performed and wherein (1) the superimposition of docked poses of 1 and 4 in FR□□(PDB: 4LRH).[13] Modeled using MOE 2014.08.[12] and a ligand interaction plot of 4 in FR□ (not shown), and (ii) the superimposition of docked poses of 1 and 4 and in GARFTase (PDB: 1NJS).[14] Modeled using MOE 2014.08.[12] and a ligand interaction plot of 4 in GARFTase (not shown). A docked pose of the fluorinated analog 4 in FRα (PDB ID: 4LRH) and GARFTase (PDB ID: 1NJS) respectively, was performed (not shown). With the exception of the side chain glutamates, both compounds retain the interaction patterns of the bicyclic scaffold and side chain aryl moiety as the parent analog 1 in both proteins. The L-glutamate side chain of 4 is oriented with the —NH of the glutamate facing the fluorine to facilitate a pseudo 6-membered ring via a possible fluorine hydrogen bond. The distance between the fluorine and —NH was 2.99 Å and 2.68 Å in the docked poses of 4 in FRα and GARFTase respectively, which are both within hydrogen bonding range.[11]

Syntheses:

Syntheses of the 4-Carbon Linker Intermediates 11 and 13 in the Targeted Antifolates Scheme 1

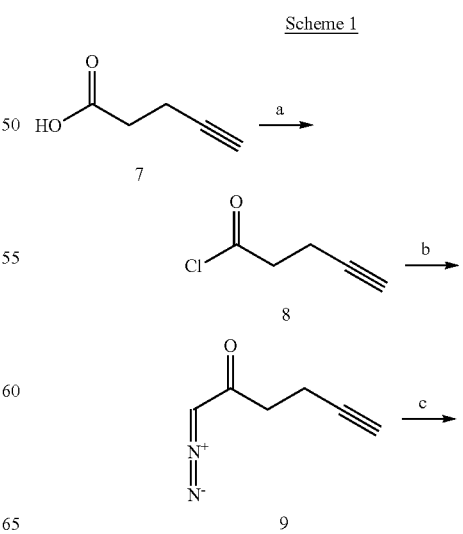

33
-continued
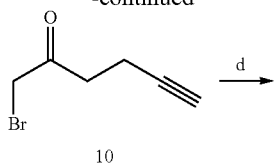
10
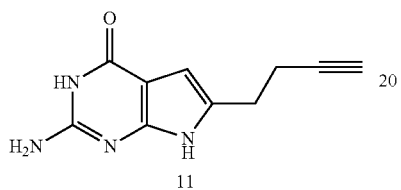
11
Reagents and conditions: (a) (COCl)₂, DCM, reflux, 1 h (b) CH₂N₂, (Et)₂O, 0° C.-rt, 1 h (c) 48% HBr, (Et)₂O, 80° C., 2 h (d) 2, 4-diamino-6-hydroxypyrimidine, DMF, rt, 3 days, 55%
34
Scheme 2
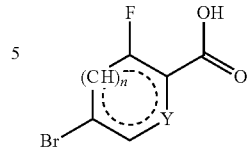
12
n = 1, Y = C, N
n = 0, Y = S
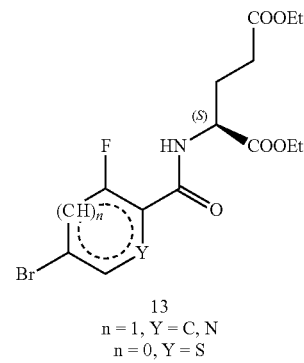
13
n = 1, Y = C, N
n = 0, Y = S
Reagents and conditions: (a) NMM, 2,4-dimethoxy-6-chloro-triazine, diethyl-L-glutamate, DMF, rt, 12 h,
Scheme 3
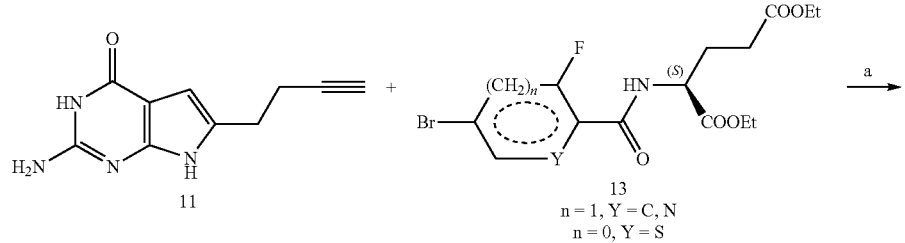
13
n = 1, Y = C, N
n = 0, Y = S
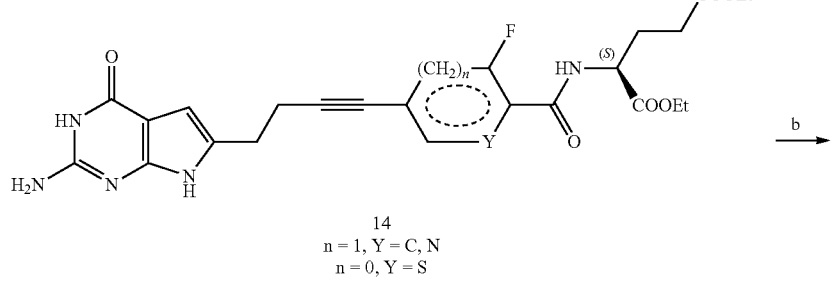
14
n = 1, Y = C, N
n = 0, Y = S -continued

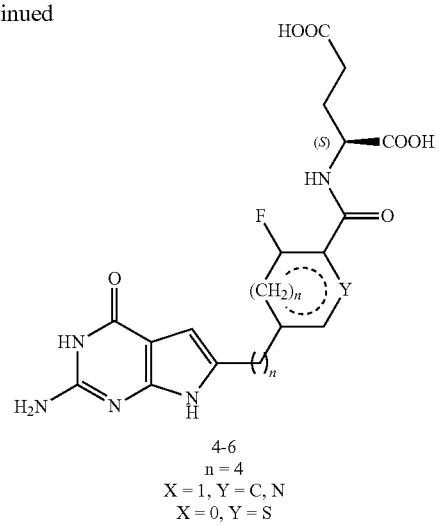

4-6
n = 4
X = 1, Y = C, N
X = 0, Y = S

Reagents and conditions: (a) CuI, Pd(0), TEA, DMF, 60° C., μW, 12 h, 43-60% (b) 1) 10% Pd/C, H$_2$, 12 h; 2) 1N NaOH, rt, 1 h, 70-76%

Chemistry

Commercially available acetylene carboxylic acid 7 was converted to α-chloromethylketone 10, which was cyclized to the key intermediate, 2-amino-4-oxo-6-alkynyl-pyrrolo[2,3-d]pyrimidine 11 (Scheme 1). Sequential Sonogashira coupling with bromo-(het)aryl-fluoro-glutamate esters 13, hydrogenation and saponification afforded the target compounds 4-6 (Schemes 2-3).

Biological Evaluation and Discussion

Section III—Table 1. IC$_{50}$ values (nM) for 6-substituted pyrrolo[2,3-d]pyrimidine antifolates with fluorine in the side chain (het)aryl ring 4, 5, and 6 in comparison with their des-fluoro parent analogs 1, 2[15], and 3 and the clinically used classical antifolate PMX in RFC-, PCFT-, and FR-expressing Chinese hamster ovary (CHO) cell lines and KB tumor cells. $^a$Growth inhibition assays for CHO sublines engineered to express human RFC (PC43-10), FRα (RT16), or PCFT (R2/PCFT4) were compared with results for transporter-null (R2 and R2(VC)) CHO cells and for the KB human tumor sub-lines (expressing RFC, FRα, and PCFT). The data shown summarize results from 3 to 10 experiments. The results are presented as mean IC$_{50}$ values corresponding to the concentrations that inhibit growth by 50% relative to cells incubated without drug.

Section III—

TABLE 1

| Antifolate | KB (nM) RFC/FRα/PCFT | PC43-10 (nM) RFC | R2 (nM) Null | RT16 (nM) FRα | D4/(nM) FRβ | PCFT4 (nM) PCFT |
|---|---|---|---|---|---|---|
| PMX | 9.94 | 30.6 | 894 | 18.2 | 60 | 22.3 |
| 1 | 1.9 | >1000 | >1000 | 6.3 | 10 | 213 |

TABLE 1-continued

| Antifolate | KB (nM) RFC/FRα/PCFT | PC43-10 (nM) RFC | R2 (nM) Null | RT16 (nM) FRα | D4/(nM) FRβ | PCFT4 (nM) PCFT |
|---|---|---|---|---|---|---|
| 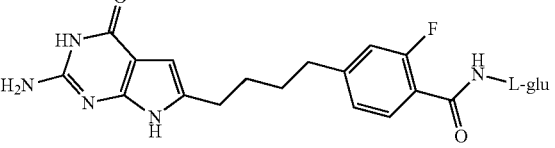 4 | 0.549 | >1000 | >1000 | 0.47 | 0.88 | 75 |
| 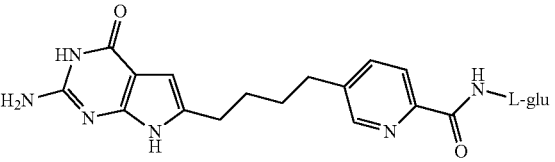 2 | 0.34 | >1000 | >1000 | 1.27 | 0.52 | 57.6 |
| 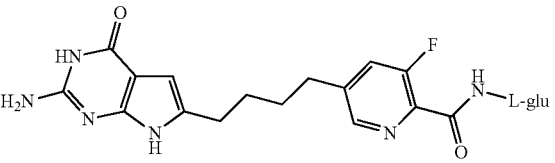 5 | 0.23 | 937 | >1000 | 0.69 | 1.61 | 73 |
| 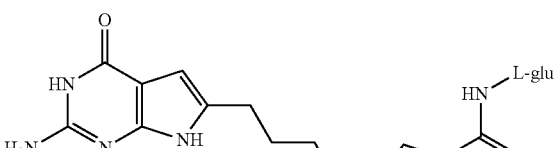 3 | 0.48 | >1000 | >1000 | 2.54 | 0.43 | 41.54 |
|  6 | 0.68 | 207 | >1000 | 0.35 | 1.9 | 8.23 |

In FRα and β expressing R16 and D4 CHO cell lines and in KB human tumor cells, the introduction of fluorine on the phenyl side chain in 4 resulted in greater potency compared to the des-fluoro parent analog 1, as reflected in $IC_{50}$ values for inhibition of cell proliferation (Table 1). However, for 2 and 3 with heteroaryl side chain, there was limited impact of fluorine substitutions in 5 and 6 on FR-targeted activity. In the PCFT-expressing CHO cell line (R2/PCFT4), the fluorine analogs 4 and 6 showed improved activities (decreased $IC_{50}$ values) compared to the corresponding des-fluoro analogs 1 and 3, respectively. For compounds 2 and 5, the activity toward PCFT-expressing R2/PCFT4 cells was comparable. Of particular interest, the $IC_{50}$ for the PCFT-targeted with R2/PCFT4 cells compound 6 was 8.23 nM, approaching that for the most potent PCFT-targeted compounds reported to date. For compounds 1-5, activity toward RFC-expressing PC43-10 cells was insignificant up to 1000 nM. While compound 6 showed an $IC_{50}$ with RFC-expressing PC43-10 cells of 207 nM, this was still well in excess of that for either FR- or PCFT-expressing cells.

Summary

The synthesis of a fluorine ortho to the L-glutamate moiety in our previously synthesized des-fluoro targeted antifolates afforded varied results. For the phenyl side chain compound 4, the potency increased toward FR- and PCFT-expressing CHO and KB cells. While potencies for 5 and 6 toward FR-expressing CHO and KB cells were preserved compared the corresponding des-fluoro analogs, compound 6 was unique from compound 5 in its dramatic ~5-fold increased potency toward PCFT-expressing CHO cells, approaching that of the most potent PCFT-targeted agents yet described. Fluorinated antifolates typified by compounds 4-6 offer a structural simplicity for drug design and represent an important step toward further optimizing the tumor-targeted antifolates with selective transport via FRs and PCFT over RFC.

This invention provides the following compounds:

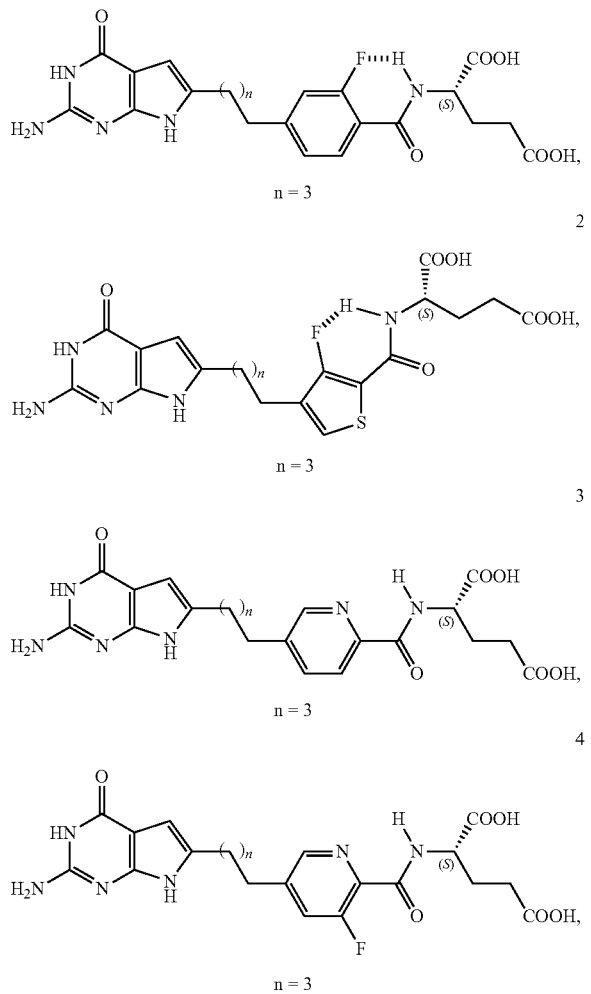

Section III References:
1) Wang, L.; Cherian, C.; Desmoulin, S. K.; Mitchell-Ryan, S.; Hou, Z.; Matherly, L. H.; Gangjee, A. Synthesis, biological and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase. *J. Med. Chem.* 2012, 55, 1758-1770.
2) Deng, Y.; Wang, Y.; Cherian, C.; Hou, Z.; Buck, S. A.; Matherly, L. H.; Gangjee, A. Synthesis and discovery of high affinity folate receptor-specific glycinamide ribonucleotide formyltransferase inhibitors with antitumor activity. *J. Med. Chem.* 2008, 51, 5052-5063.
3) Elnakat, H.; Ratnam, M. Distribution, functionality and gene regulation of folate receptor isoforms: implications in targeted therapy. *Adv. Drug. Deliv. Rev.* 2004, 56, 1067-1084.
4) Nakai, Y.; Inoue, K.; Abe, N.; Hatakeyama, M.; Ohta, K.; Otagiri, M.; Hayashi, Y.; Yuasa, H. Functional characterization of human proton-coupled folate transporter/heme carrier protein 1 heterologously expressed in mammalian cells as a folate transporter. *J. Pharmacol. Exp. Ther.* 2007, 322, 469-476.
5) Qiu, A.; Jansen, M.; Sakaris, A.; Min, S.; Chattopadhyay, S.; Tsai, E.; Sandoval, C.; Zhao, R.; Akabas, M.; Goldman, I. D. Identification of an intestinal folate transporter and the molecular basis for hereditary folate malabsorption. *Cell.* 2006, 127, 917-928.
6) Qiu, A.; Min, S.; Jansen, M.; Malhotra, U.; Tsai, E.; Cabelof, D.; Matherly L. H., Zhao, R.; Akabas, M.; Goldman, I. D. Rodent intestinal folate transporters (SLC46A1): secondary structure, functional properties, and response to dietary folate restriction. *Am. J. Physiol. Cell. Physiol.* 2007, 293, 1669-1678.
7) Matherly, L. H.; Hou, Z.; Deng, Y. Human reduced folate carrier: translation of basic biology to cancer etiology and therapy. *Cancer Metastasis Rev.* 2007, 26, 111-128.
8) Zhao, R.; Goldman, I. D. Resistance To Antifolates. *Oncogene.* 2003, 22, 7431-7457.
9) Baldwin, S. W.; Tse. A.; Gossett, L. S.; Taylor, E. C.; Rosowsky, A.; Shih, C.; Moran, R. G. Structural features of 5,10-dideaza-5,6,7,8-tetrahydrofolate that determine inhibition of mammalian glycinamide ribonucleotide formyltransferase. *Biochemistry.* 1991, 30, 1997-2006.
10) Duch, D. S.; Banks, S.; Dev, I. K.; Dickerson, S. H.; Ferone, R.; Heath, L. S.; Humphreys, J.; Knick, V.; Pendergast, W.; Singer, S.; Smith, G. K.; Waters, K.; Wilson, H. R. Synthesis of conformationally-constrained glutamate analogues of the antitumor agents DDATHF, LY254155, and LY231514. *Cancer Res.* 1993, 53, 810.
11) Eric P. G; Kyle J. E.; Matthew D. H.; David J. D.; and Nicholas A. M. *Applications of fluorine in medicinal chemistry. J. Med. Chem.* ASAP. DOI: 10.1021/acs.jmedchem.5b00258.
12) MOE 2014.08; Chemical Computing Group: Montreal, Quebec, Canada, 2014.
13) Chen, C.; Ke, J.; Zhou, X. E.; Brunzelle, J. S.; Li, J.; Yong, E.-L.; Xu, H. E.; Melcher, K. Structural basis for molecular recognition of folic acid by folate receptors. *Nature.* 2013, 500, 486-489
14) Zhang, Y.; Desharnais, J.; Marsilje, T. H.; Li, C.; Hedrick, M. P.; Gooljarsingh, L. T.; Tavassoli, A.; Benkovic, S. J.; Olson, A. J.; Boger, D. L.; Wilson, I. A. Rational design, synthesis, evaluation, and crystal structure of a potent inhibitor of human GAR tfase: 10 (trifluoroacetyl)-5,10-dideazaacyclic-5,6,7,8-tetrahydrofolic acid. *Biochemistry.* 2003, 42, 6043-6056.
15) Gangjee, A.; Wang, L.; and Matherly, L. H. Unpublished results.

Section IV: 6-Substituted Pyrrolo[2,3-d]Pyrimidines as Targeted Antifolate Compounds Reduced folates are essential cofactors for the biosynthesis of purines and pyrimidines. Since humans do not synthesize folate, it is necessary to obtain these cofactors from dietary sources. In mammals, three specialized systems exist that mediate membrane transport of folates and antifolates across biological membranes. These include the reduced folate carrier (RFC), the primary route for the uptake of folates and antifolates in mammalian cells, folate receptors (FRs) α and β, and the proton-coupled folate transporter (PCFT). Whereas RFC is ubiquitously expressed, FRs and PCFT show a narrower pattern of tissue expression. Toxicity of clinically used antifolates is attributed in part, to their lack of selectivity for tumor cells over normal cells due to RFC transport. Antifolates with tumor-specific FR and/or PCFT drug uptake would circumvent major toxicities of currently used antifolates. Our three carbon atom chain analog AGF17 had shown 25-fold greater selectivity for FR transport over RFC with excellent cell inhibitory activity against KB human tumor cells ($IC_{50}$=1.8 nM). On the basis of results with AGF17, three novel analogues, AGF233 with regioisomeric replacement of para C10 to meta C10, AGF220 with oxygen in place of carbon at C10 of AGF233 and AGF256 with nitrogen in place of carbon at C10 of AGF233 were designed and synthesized. This simple regioisomeric and isosteric replacement of carbon with heteroatoms in the bridge provides compounds with different chain lengths, angles, conformations and extra hydrogen bond donors and/or acceptors compared to the parent carbon chain analogues. AGF17 had shown low levels of inhibitory activity toward the growth of a Chinese hamster ovary (CHO) cell line (PC43-10) expressing human RFC ($IC_{50}$=648 nM), however the analogues AGF233, AGF220 and AGF256 were inactive in the CHO cell line expressing RFC transport at concentrations up to 1000 nM. However, AGF233, AGF220 and AGF256 were active in inhibiting a CHO cell line (RT16) expressing human FRα ($IC_{50s}$ of 60.29, 30.33 and 15.9 nM, respectively). AGF233, AGF220 and AGF256 were also potently inhibitory toward KB tumor cells ($IC_{50}$s of 2.61, 13.14 and 14.8 nM, respectively). Structural formulae for compounds AGF233, AGF220 and AGF256 of this invention are provided below:

folate carrier (RFC), the primary route for the uptake of folates and antifolates in mammalian cells,[1-3] folate receptors (FRs) α and β,[4-5] and the proton-coupled folate transporter (PCFT).[6-7] Whereas RFC is ubiquitously expressed, FRs and PCFT show a narrower pattern of tissue expression.[2-4] Toxicity of clinically used antifolates is attributed in major part, to their lack of selectivity for tumor cells over normal cells due to RFC transport. Antifolates with tumor-specific FR and/or PCFT drug uptake would circumvent major toxicities of currently used antifolates. Our three carbon atom chain analog AGF17 had shown 25-fold greater selectivity for FR transport over RFC with excellent cell inhibitory activity against KB human tumor cells ($IC_{50}$=1.8 nM).[8] On the basis of results with AGF17, three novel analogues; AGF233 with regioisomeric replacement of a para C10 substitution to a meta C10; and AGF220 and AGF256 with isosteric oxygen and nitrogen, respectively in place of carbon at C10 of AGF233 were designed and synthesized. This simple regioisomeric and isosteric replacement of carbon with heteroatoms in the bridge provides compounds with different chain lengths, angles, conformations and extra hydrogen bond donors and/or acceptors compared to the parent carbon chain analogues.

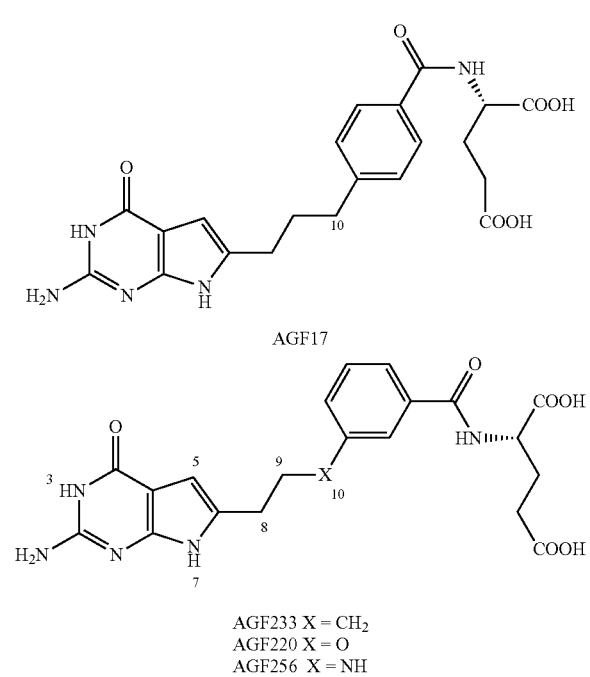

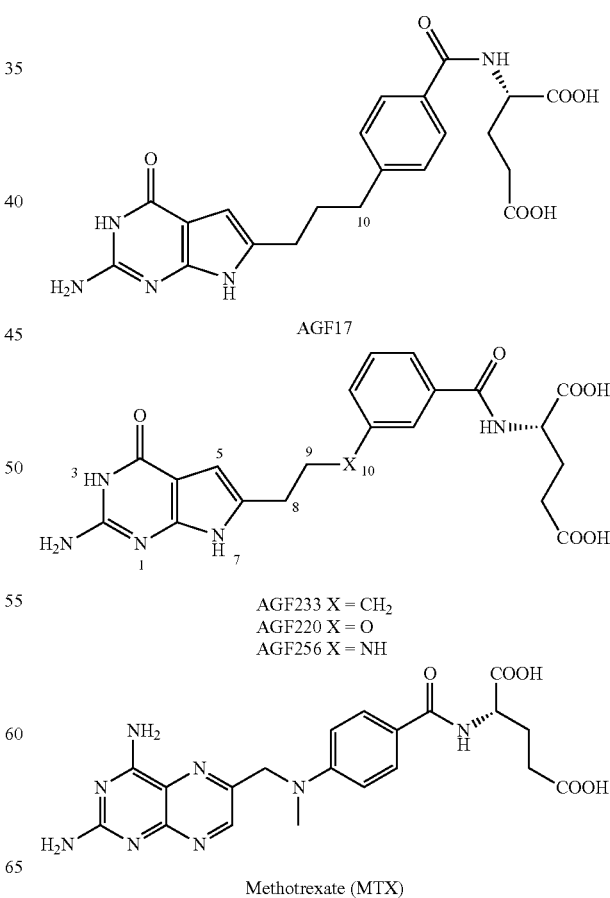

Introduction

Reduced folates are essential cofactors for the biosynthesis of purines and pyrimidines. Since humans do not synthesize folate, it is necessary to obtain these cofactors from dietary sources. In mammals, three specialized systems exist that mediate membrane transport of folates and antifolates across biological membranes.[1-3] These include the reduced

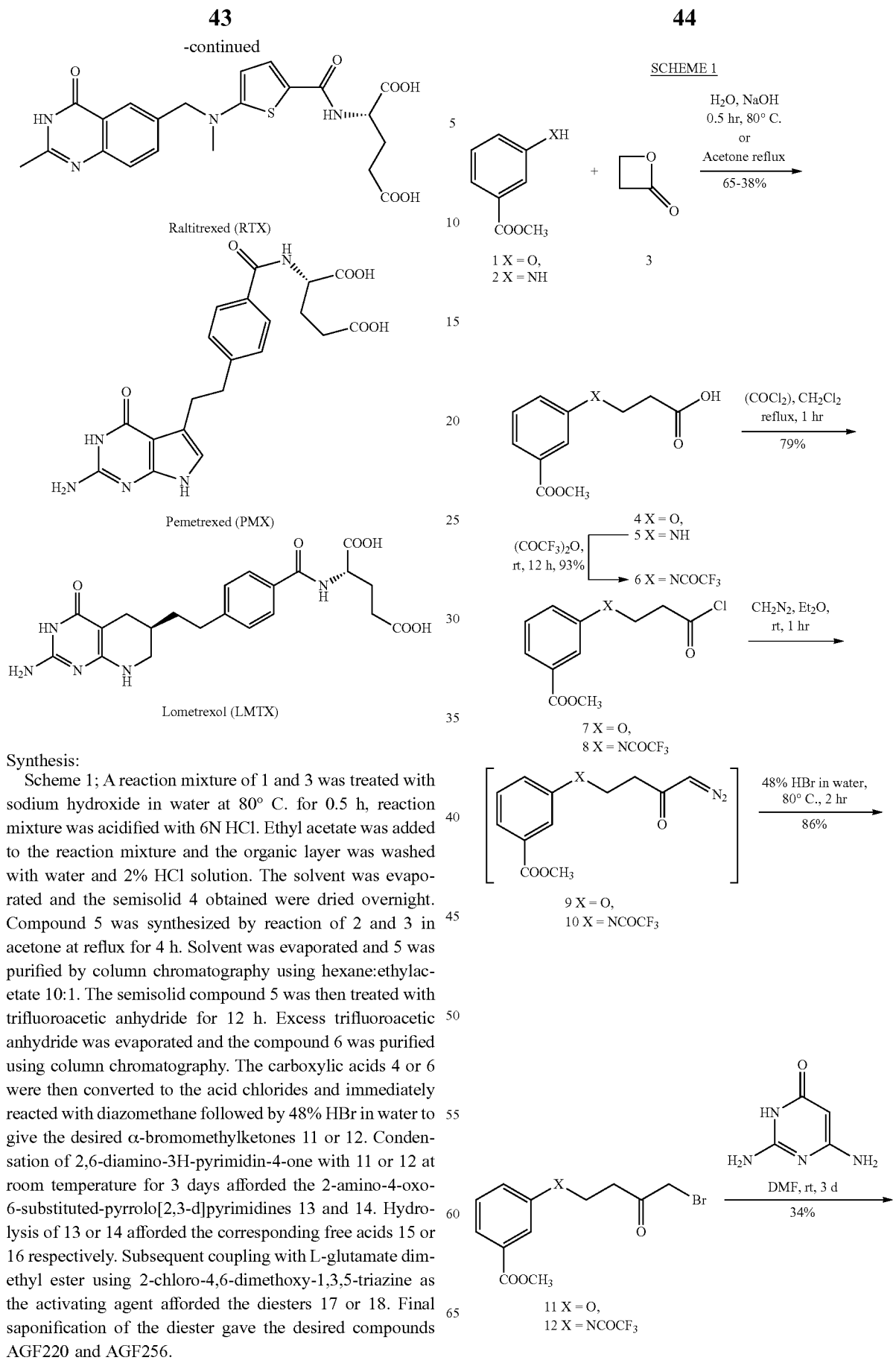

Synthesis:
Scheme 1; A reaction mixture of 1 and 3 was treated with sodium hydroxide in water at 80° C. for 0.5 h, reaction mixture was acidified with 6N HCl. Ethyl acetate was added to the reaction mixture and the organic layer was washed with water and 2% HCl solution. The solvent was evaporated and the semisolid 4 obtained were dried overnight. Compound 5 was synthesized by reaction of 2 and 3 in acetone at reflux for 4 h. Solvent was evaporated and 5 was purified by column chromatography using hexane:ethylacetate 10:1. The semisolid compound 5 was then treated with trifluoroacetic anhydride for 12 h. Excess trifluoroacetic anhydride was evaporated and the compound 6 was purified using column chromatography. The carboxylic acids 4 or 6 were then converted to the acid chlorides and immediately reacted with diazomethane followed by 48% HBr in water to give the desired α-bromomethylketones 11 or 12. Condensation of 2,6-diamino-3H-pyrimidin-4-one with 11 or 12 at room temperature for 3 days afforded the 2-amino-4-oxo-6-substituted-pyrrolo[2,3-d]pyrimidines 13 and 14. Hydrolysis of 13 or 14 afforded the corresponding free acids 15 or 16 respectively. Subsequent coupling with L-glutamate dimethyl ester using 2-chloro-4,6-dimethoxy-1,3,5-triazine as the activating agent afforded the diesters 17 or 18. Final saponification of the diester gave the desired compounds AGF220 and AGF256.

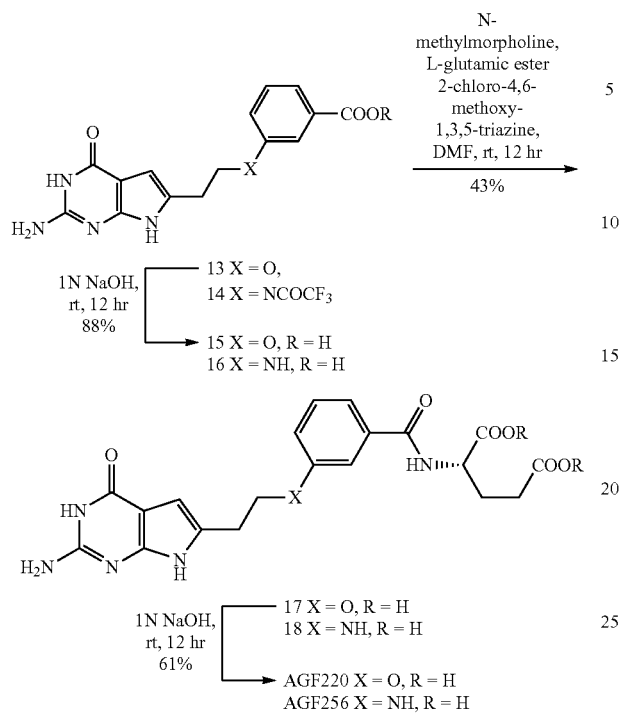

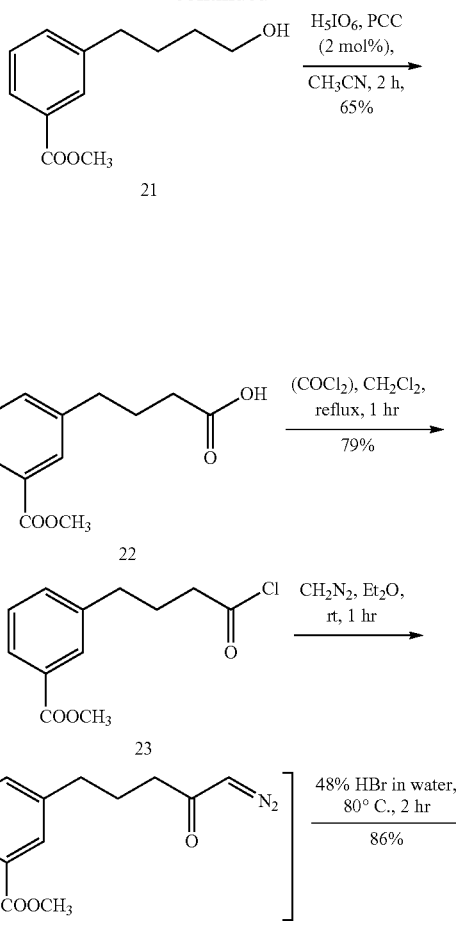

In SCHEME 2, a Sonogashira coupling of 19 with 4-butyn-1-ol afforded 20 in 60% yield. Subsequent hydrogenation of 20 afforded 21. Compound 21 was oxidized using periodic acid and pyridinium chlorochromate to 22. Intermediate 22 was converted to the acid chloride and immediately reacted with diazomethane, followed by 48% HBr to give the desired α-bromomethylketone 25. Condensation of 2,6-diamino-3H-pyrimidin-4-one with 25 at room temperature for 3 days afforded the 2-amino-4-oxo-6-substituted-pyrrolo[2,3-d]pyrimidine 26. Hydrolysis of 26 gave the corresponding free acid 27. Subsequent coupling with L-glutamate dimethyl ester afforded 28. Final saponification of the ester gave the desired compound AGF256, in 61% yield (note: in "SCHEME 2—'AGF256'" wherein R═H is also identified as compound AGF233 herein).

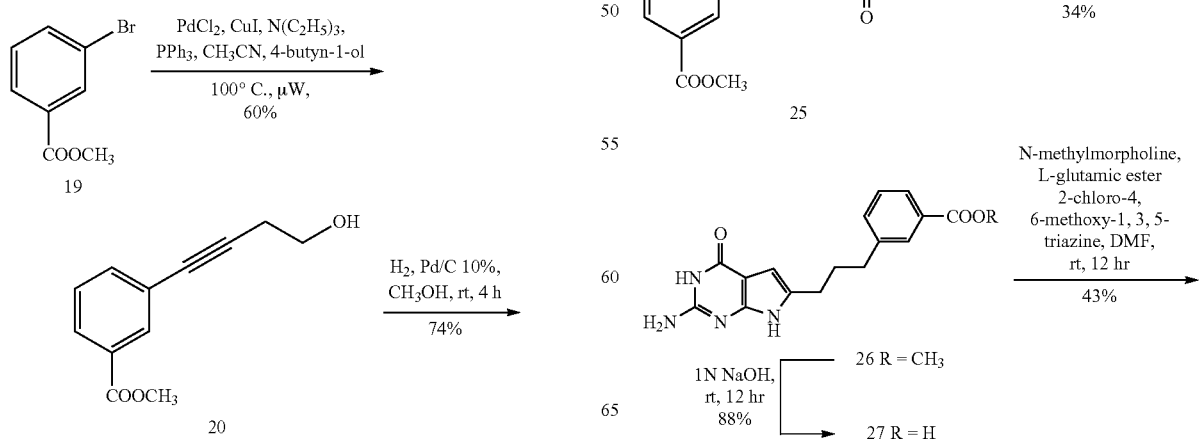

-continued

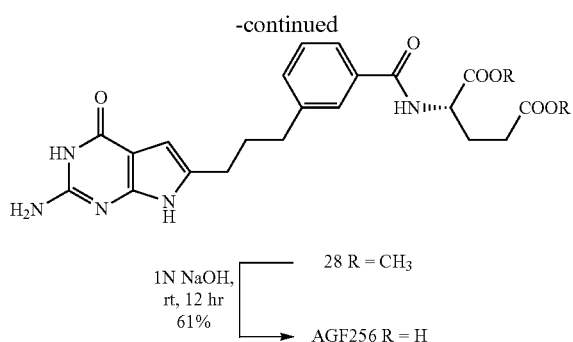

28 R = CH₃

1N NaOH, rt, 12 hr 61%

AGF256 R = H

Section IV—Table 1:

TABLE 1

IC$_{50}$s (in nM) for 6-substituted pyrrrolo[2,3-d]pyrimidine thienoyl antifolates AGF17, AGF233, AGF220, and AGF256 classical antifolates in RFC-, PCFT-, and FR-expressing cell lines.

| | | | FRα | | FRβ | | PCFT | | RFC/FRα/PCFT | |
|---|---|---|---|---|---|---|---|---|---|---|
| | RFC | | RT16 | | D4 | | R2/ | R2 | | KB |
| Antifolate | PC43-10 | R2 | RT16 | (+FA) | D4 | (+FA) | hPCFT4 | (VC) | KB | (+FA) |
| AGF17 | 648 (38.1) | >1000 | 3.2 (1.6) | >1000 | 2.7 (1.2) | >1000 | 23 (3.25) | >1000 | 1.8 (0.7) | >1000 |
| AGF233 | >1000 | >1000 | 60.29 (0.96) | >1000 | 17.24 (1.51) | >1000 | >1000 | >1000 | 2.61 (0.74) | >1000 |
| AGF220 | >1000 | >1000 | 30.33 (0.32) | >1000 | ND | ND | ND | ND | 13.14 (0.30) | >1000 |
| AGF256 | >1000 | >1000 | 15.9 (0.32) | >1000 | 4.19 | >1000 | ND | ND | 14.8 (0.05) | >1000 |
| MTX | 12 (1.1) | 114 (31) | 114 (31) | 216 (8.7) | 106 (11) | 211 (43) | 121 (17) | >1000 | 6.0 (0.6) | 20 (2.4) |
| PMX | 138 (13) | 42 (9) | 42 (9) | 894 (93) | 60 (8) | 254 (78) | 13.2 (2.4) | 974 (18) | 68 (12) | 327 (103) |
| RTX | 6.3 (1.3) | 15 (5) | 15 (5) | >1000 | 22 (10) | 746 (138) | 99.5 (11.4) | >1000 | 5.9 (2.2) | 22 (5) |
| LMTX | 12 (2.3) | 12 (8) | 12 (8) | >1000 | 2.6 (1.0) | 275 (101) | 38.0 (5.3) | >1000 | 1.2 (0.6) | 31 (7) |

Molecular Modeling

Molecular Operating Environment (MOE), 2014.09 was used for docking and conformational analysis. The docked poses of AGF17, AGF233, AGF220, and AGF256 in FRα bound to folic acid.[9] were performed (not shown) wherein docking of AGF17, AGF233, AGF220, and AGF256 in the folate receptor alpha crystal structure (PDB; 4LRH)[9]. The 2-NH$_2$ and 3-NH of AGF17, AGF233, AGF220, and AGF256 interact with the same amino acids as the corresponding groups of folic acid. The α-carboxylic acid of AGF17, AGF233, AGF220, and AGF256 is oriented similar to the α-carboxylic acid of folic acid and forms a hydrogen bond with the Trp102 side chain. The docking scores of all four analogs were in the range of −9.20 to −8.06 kcal/mol compared with folic acid of −9.12 kcal/mol. The docking scores of the four analogs were in the order, AGF17<AGF256<AGF220<AGF233. Since AGF17 was shown to target glycinamide ribonucleotide formyltransferase (GARFTase), it was of interest to dock all four analogues to explore the molecular basis of their activity against GARFTase. Molecular modeling studies were carried out using the X-ray crystal structure of human GARFTase bound to trifluoroacetyl-5,10-dideaza-acyclic-5,6,7,8-tetrahydrofolic acid.[10] The docked pose of 10-(trifluoroacetyl)-5,10-dideazaacyclic-5,6,7,8-tetrahydrofolic acid, AGF17, AGF233, AGF220, and AGF256 were performed (not shown) wherein docking of AGF17, AGF233, AGF220, and AGF256 in the GARFTase crystal structure (PDB; 1NJS)[10].

The pyrrolo[2,3-d]pyrimidine scaffold of all four analogs binds in the region occupied by the diaminopyrimidine ring in 10-CF$_3$CO-DDACTHF. The 2-NH$_2$, 3-NH and 7-NH of all four analogs interact with the same amino acids as the corresponding groups of 10-CF$_3$CO-DDACTHF. The pyrrolo[2,3-d]pyrimidine scaffold of all four analogs forms hydrophobic interactions with Ile91 and Val143. The α-carboxylic acid of AGF17, AGF233, AGF220, and AGF256 does not show any interactions. The γ-carboxylic acid of all four analogs interact with Arg64 and Arg90. The docking scores of the four analogs were in the order, AGF17<AGF233<AGF220<AGF256. These interactions and the number of low energy docked conformations explain, in part, the rank order of the potent inhibition (IC$_{50s}$ values) against KB tumor cells in Table 1 of the four analogs as AGF17<AGF233<AGF220<AGF256.

Summary

AGF17 had shown comparatively low levels of inhibitory activity toward the growth of a Chinese hamster ovary (CHO) cell line (PC43-10) expressing human RFC (IC$_{50}$=648 nM), however the analogues AGF233, AGF220 and AGF256 were inactive in the CHO cell line expressing RFC transport at concentrations up to 1000 nM. AGF233, AGF220 and AGF256 were active in inhibiting CHO cell line (RT16) expressing human FRα (IC$_{50s}$ of 60.29, 30.33 and 15.9 nM, respectively). AGF233, AGF220 and AGF256 were also potently inhibitory toward KB tumor cells (IC$_{50}$s of 2.61, 13.14 and 14.8 nM, respectively). Thus AGF233, AGF220 and AGF256 have absolute selectively for FR α and β over RFC and are potential analogues for further preclinical studies and analogue design as targeted antifolates.

Section IV References:

1. Matherly, L. H.; Goldman, I. D. Vitam. Horm. 2003, 66, 403-456.
2. Matherly, L. H.; Hou, Z.; Deng, Y. Cancer Metastasis Rev. 2007, 26, 111-128.
3. Zhao, R.; Matherly, L. H.; Goldman, I. D. Expert Rev. Mol. Med. 2009, 11, No. e4.
4. Salazar, M. D.; Ratnam, M. Cancer Metastasis Rev. 2007, 26, 141-152.
5. Elnakat, H.; Ratnam, M. Adv. Drug Delivery 2004, 56, 1067-1084.
6. Goldman, I. D. et al. Cell 2006, 127, 917-928.
7. Zhao, R.; Goldman, I. D. Cancer Metastasis Rev. 2007, 26, 129-139.
8. Deng, Y.; Wang, Y.; Cherian, C.; Hou, Zhanjun; Buck, S. A.; Matherly, L. H.; Gangjee, A. J. Med. Chem. 2008, 51, 5052-5063.
9. Chen, C.; Ke, J.; Zhou, X. E.; Yi, W.; Brunzelle, J. S.; Li, J.; Yong, E.-L.; Xu, H. E.; Melcher, K. Nature 2013, 500 (7463), 486-489.

10. Zhang, Y.; Desharnais, J.; Marsilje, T. H.; Li, C.; Hedrick, M. P.; Gooljarsingh, L. T.; Tavassoli, A.; Benkovic, S. J.; Olson, A. J.; Boger, D. L.; Wilson, I. A. Biochemistry 2003, 42 (20), 6043-6056.

Section V: Monocyclic Pyrimidine Analogs as Novel Colchicine Site Binding Anti-Tubulin Compounds Microtubule binding agents represent a widely used class of chemotherapeutic agents which act by interfering with microtubule dynamics. They are mainly classified as microtubule stabilizing agents, binding to taxol binding site or the laulimalide/peloruside A site on the tubulin and microtubule destabilizing agents, binding to either vinca binding site or the colchicine binding domain (CBD). Development of agents binding to CBD is of particular interest because of their ability to overcome β-III resistant as well as Pgp mediated resistance in cancer cell lines. Also, no agent binding to the CBD has been clinically approved so far. We had previously reported a series of pyrrolo[2,3-d]pyrimidine analogs binding to the CBD. To see the minimal structural requirement for compounds to be effective inhibitors at the CBD, monocyclic pyrimidine analogs were proposed and presented. This work is an extension of the same study wherein alkyl substitutions at the N-6 position of the 6-amino-5-chloro-2-methyl $N^4$-substituted pyrimidine scaffold were carried out. To have a thorough understanding of the SAR some additional analogs were also synthesized. The design, synthesis and biological activities of these compounds is set forth herein. The structures of the compounds of this invention are as follows:

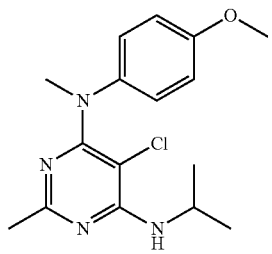

1

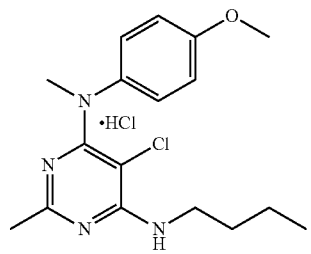

2

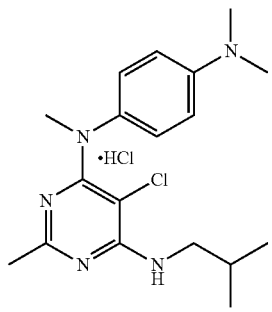

3

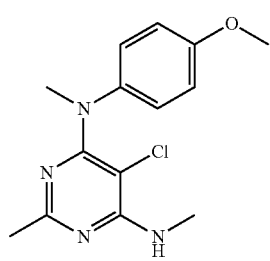

4

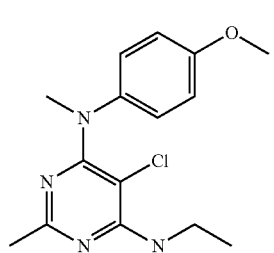

5

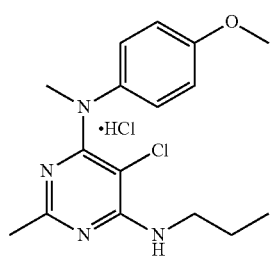

6

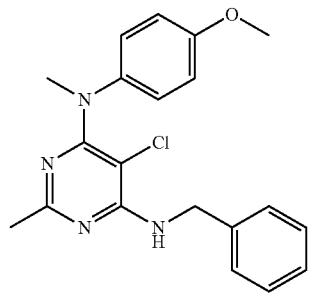

7

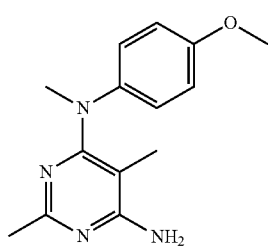

8

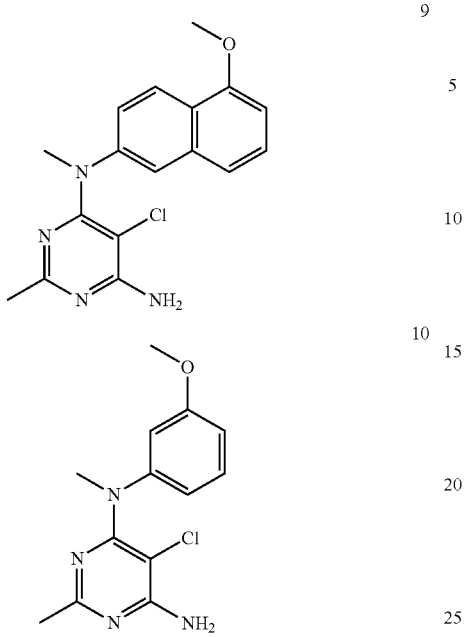

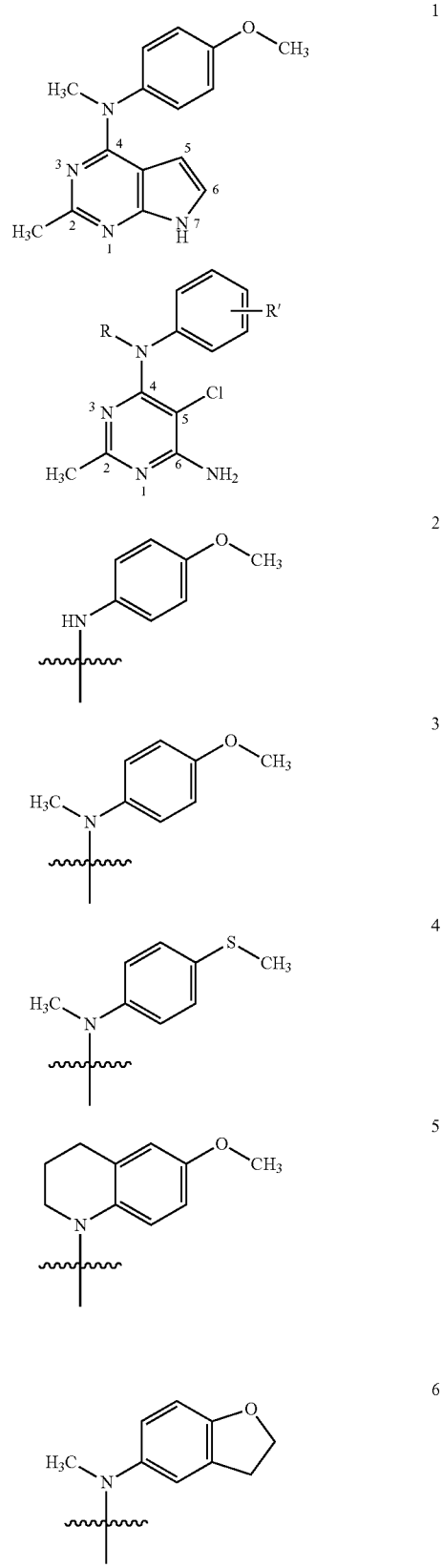

Microtubules (MTs) are one of three major components of the eukaryotic cytoskeleton, and MTs are composed of αβ-tubulin. MTs are highly dynamic, filamentous polymers that are involved in vital cellular processes like intracellular transport, cellular signaling, vesicle formation, maintaining shape and size of the cell and comprise mitotic spindle.[1] The dynamic behavior of MTs arises from their ability to undergo polymerization and depolymerization. In the presence of GTP, the soluble α,β-tubulin heterodimers polymerize into MTs of varying lengths.[2]

Antitubulin agents act as mitotic poisons, but recent evidence suggests that their ability to interrupt interphase signaling events likely contributes to their anticancer actions.[3] Based on their ability to affect cellular MT density, they are classified as microtubule stabilizers or microtubule destabilizers. Amongst the stabilizers are compounds binding to the taxol site and the laulimalide/peloruside site.[4,5] Under the category of destabilizers are compounds binding to the vinca site, the colchicine site or the maytansine site.[6,7]

Gangjee et al.[8,9] previously reported 1 and its structurally simplified derivatives (FIG. 2) to explore the minimum structural requirement for the inhibitory effect of these compounds on tubulin polymerization, cellular microtubule and cell growth. These analogs were successful in inhibiting cell growth in β-III-tubulin overexpressing and P-gp expressing cancer cell lines.[9] The relevance of this finding is particularly important as it has been observed that overexpression of β-III-tubulin is associated with resistance towards clinically approved agents like vinorelbine and taxanes.[4,10] In addition, P-gp is involved in the active cellular efflux of vinca alkaloids and taxanes and expression leads to multidrug resistance.[4,10]

Structure of a lead compound 1 and analog compounds 2-6 of this invention.

Section V—Table 1:

TABLE 1

| Compound No. | IC$_{50}$ MDA-MB-435 (nM) | EC$_{50}$ Microtubule depolymerization (μM) |
|---|---|---|
| 1 | 183 ± 3.4 | 5.8 |
| 3 | 71.3 ± 6.1 | 1.5 | ally, a benzyl group was also substituted to determine the effect of bulk at the N6 position. To evaluate the importance of the 5-Cl substitution for its electron withdrawing and/or steric effects, compound 16 with a 5-CH$_3$ was designed.

Molecular Modeling: Molecular modeling (not shown) was performed wherein the proposed compounds were docked at the colchicine site (PDB ID: 4O2B)[12] using the docking suite of Molecular Operating Environment software (2013.0801).[13] The docking protocol reported previously[8] was used.

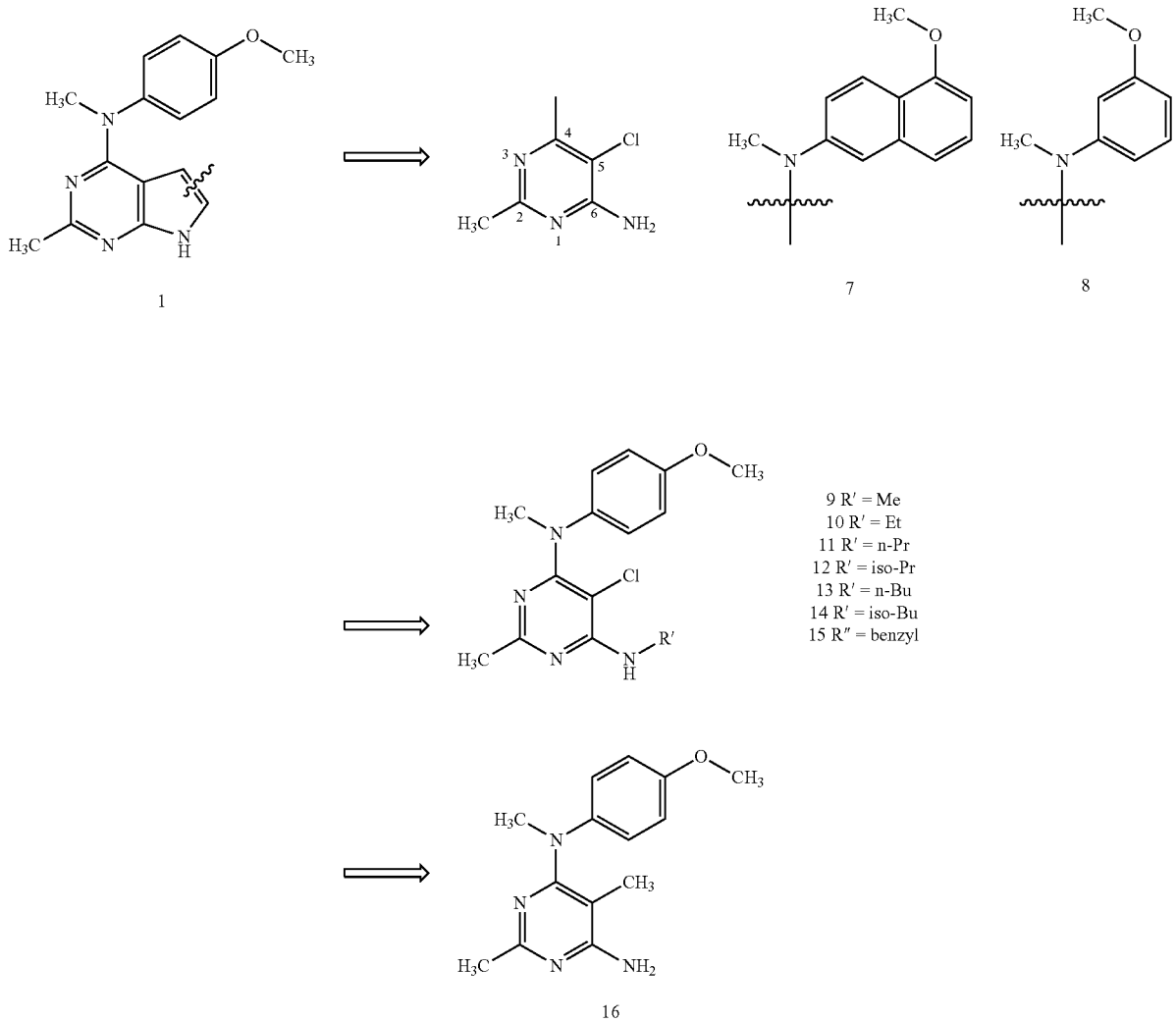

Pyrimidine analogs compounds 7-16 of this invention

We had initially reported the biological effect of varying substitution at the N4-position of 5-chloro-N4-substituted-2-methylpyrimidine-4,6-diamines.[9] Compounds with additional substituents were synthesized, and the 4-methoxy-N-methyl aniline proved to be the optimum substitution at the N4 position in the pyrimidine. On the basis of the reported size of the colchicine binding site (10×10×4-5 Å),[11] we proposed that the activity of these compounds (FIG. 3) could be further enhanced by incorporating bulk at the N6 position. Hence, N6-alkyl substituted compounds were synthesized to evaluate the effect of N-homologation on their cytotoxic and microtubule disrupting activities. Addition- The syntheses of compounds 7-16 are presented in Schemes 1, 2 and 3.

Scheme 1

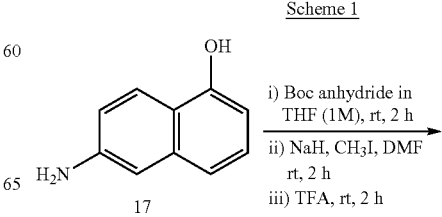

i) Boc anhydride in THF (1M), rt, 2 h
ii) NaH, CH$_3$I, DMF rt, 2 h
iii) TFA, rt, 2 h

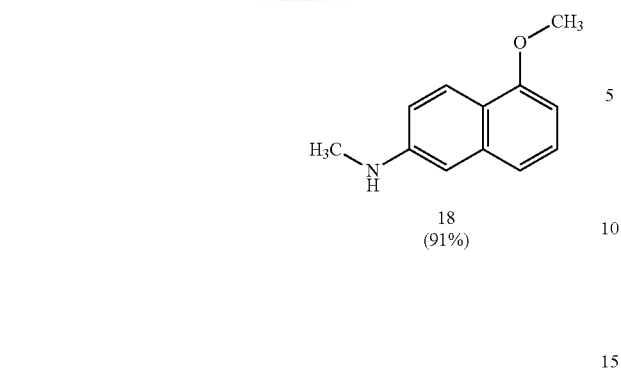
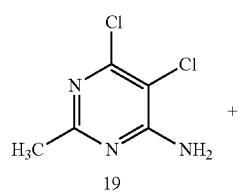
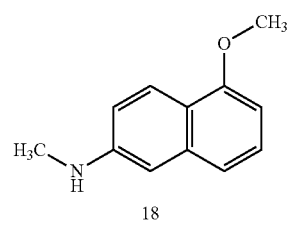
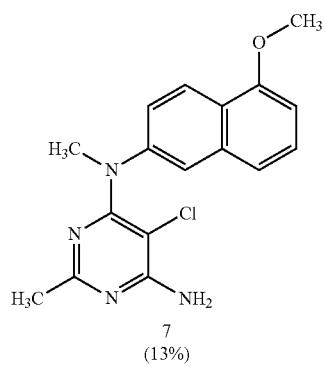
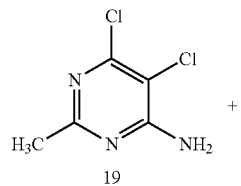
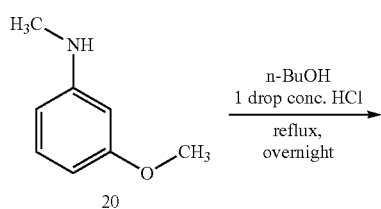
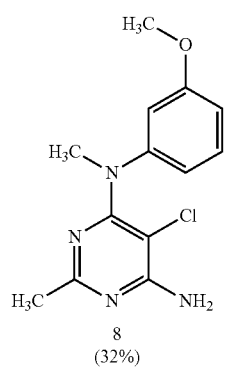
Scheme 2
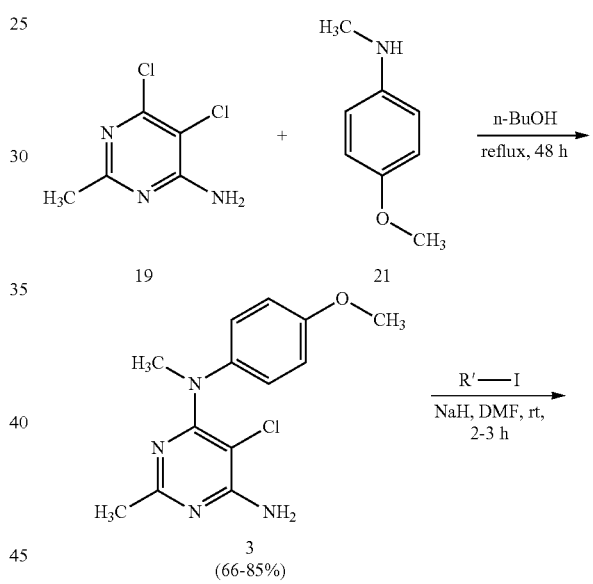
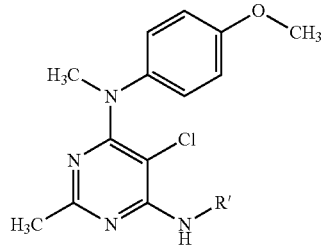
9 R' = Me (30%)
10 R' = Et (36%)
11 R' = n-Pr (semi-solid)
12 R' = iso-Pr (46%)
13 R' = n-Bu (semi-solid)
14 R' = iso-Bu (semi-solid)
15 R' = benzyl (29%)*
*BnBr was used for the conversion of 3 to 15

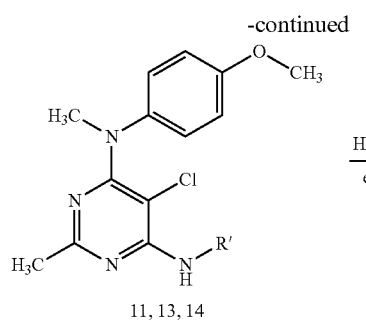

HCl (g) ether →

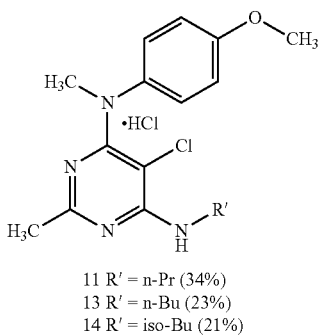

11 R' = n-Pr (34%)
13 R' = n-Bu (23%)
14 R' = iso-Bu (21%)

Scheme 3

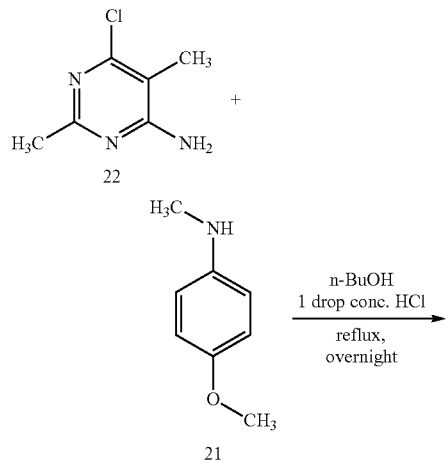

n-BuOH
1 drop conc. HCl
reflux,
overnight
→

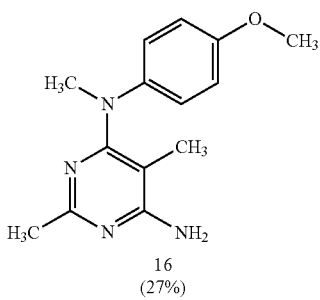

16
(27%)

Compounds 7-16 were tested for their ability to inhibit tumor cell proliferation and to affect cellular microtubule depolymerization (Table 2). Most of the compounds (4-13) were also evaluated for inhibition of the assembly of purified tubulin and inhibition of colchicine binding to tubulin (Section V-Table 3).

Section V—Table 2:

TABLE 2

| Compound No. | $IC_{50}$ MDA-MB-435 (nM) | $EC_{50}$ Microtubule depolymerization (μM) | $EC_{50}/IC_{50}$ Ratio |
|---|---|---|---|
| 7 | 56.1 ± 5.0 | 831 | 14.8 |
| 8* | ND | ND | — |
| 9 | 103.3 ± 11.8 | 2.1 μM | 20 |
| 10 | 50.4 ± 8.0 | 305 | 6.1 |
| 11 | 24.4 ± 1.4 | 123 | 5.0 |
| 12 | 684.8 ± 53.7 | 7.4 μM | 11 |
| 13 | 84.4 ± 8.0 | 432 | 5.1 |
| 14 | 78.1 ± 2.8 | 394 | 5.0 |
| 15 | ND | >10 μM | — |
| 16 | 206.4 ± 8.9 | 8 μM | 38.8 |
| Paclitaxel | 4.5 ± 0.52 | — | — |
| CA-4 | 4.4 ± 0.46 | 9.8 | 2.2 |

Rr = Relative resistance,
CA-4 = Combretastatin A-4,
ND = Not Determined
*Compound was inactive in the preliminary microtubule assay, and was not tested further.

From comparing the activity of 3 and 7 in inhibiting microtubule depolymerization, we observed that the 5'-methoxy-N-methyl naphthyl-2'-amine substitution (7) was 2-fold more potent than the 4'-methoxy-N-methyl aniline substitution in 3. Moving the methoxy from the 4'-position of the phenyl ring to the 3'-position (8) led to complete loss of activity. Homologation of methyl (9) to ethyl (10) substitution at N6-position led to a 2-fold increase in potency towards inhibition of tumor cell proliferation and a 6-fold increase towards microtubule depolymerization. Further extending the N6-alkyl chain to n-propyl (11) led to the most potent compound in the series. With iso-propyl substitution (12), there was a dramatic loss in potency for both cell proliferation and depolymerization compared to 11. Further increase in chain length to n-butyl (13) and iso-butyl (14) led to similar activity as 10 for microtubule depolymerization and inhibition of cell proliferation. In general, homologation led to an improvement in potency of the monocyclic pyrimidine analogs of 3. In addition, in 15, substitution of the side chain with a N-benzyl led to a loss of activity, suggesting that a benzyl group is not tolerated at this position. Compound 16 was less potent than 3 for microtubule depolymerization and cell proliferation indicating that the potency of 3 could be due to the electron withdrawing effect of the C5-C1 rather than to steric effects.

Section V—Table 3:

TABLE 3

| Compound No. | Inhibition of tubulin assembly $IC_{50}$ (μM) ± SD | Inhibition of colchicine binding % Inhibition ± SD | |
|---|---|---|---|
| | | 1 μM inhibitor | 5 μM inhibitor |
| 4 | 2.4 ± 0.2 | — | 71 ± 4 |
| 5 | 2.1 ± 0.2 | — | 61 ± 5 |
| 6 | 2.9 ± 0.2 | — | 60 ± 3 |
| 8 | >20 | — | — |
| 9 | 2.6 ± 0.4 | — | 68 ± 4 |
| 10 | 1.6 ± 0.1 | — | 74 ± 3 |
| 12 | 8.4 ± 0.4 | — | — |
| 13 | 1.7 ± 0.01 | — | 84 ± 2 |
| CA-4 | 1.2 ± 0.05 | 85 ± 3 | 99 ± 0.07 |

All compounds examined were less potent than CA-4 in inhibiting tubulin assembly. However, 10 and 13 were closest in potency to CA-4 for inhibiting tubulin assembly, and these two compounds were also the most active in the series as inhibitors of the binding of [$^3$H]colchicine to tubulin, indicating that these compounds bind to the colchicine site on tubulin.

In summary, the monocyclic pyrimidine analogs (10, 11, 14) were more potent than our bicyclic lead 1 and support the notion that introducing flexibility in the rigid bicyclic molecule 1 by structural simplification and additional bulk at the N6-position can improve potency. Further optimization of this scaffold is currently underway, and additional compounds will be the topic of future presentations.

Section V References:

1. Desai, A.; Mitchison, T. J. Microtubule polymerization dynamics. *Annu. Rev. Cell Dev. Biol.* 1997, 13, 83-117.
2. Nogales, E. Structural insight into microtubule function. *Annu. Rev. Biophys. Biomol. Struct.* 2001, 30, 397-420.
3. Pasztor-Komlodi, E.; Sackett, D.; Wilkerson, J.; Fojo, T. Mitosis is not a key target of microtubule agents in patient tumors. *Nat. Rev. Clin. Oncol.* 2011, 8, 244-250.
4. Dumontet, C.; Jordan, M. A. Microtubule-binding agents: a dynamic field of cancer therapeutics. *Nat. Rev. Drug Discov.* 2010, 9, 790-803.
5. Prota, A. E.; Bargsten, K.; Northcote, P. T.; Marsh, M.; Altmann, K. -H.; Miller, J. H.; Diaz, J. F.; Steinmetz, M. O. Structural basis of microtubule stabilization by laulimalide and peloruside A. *Angew. Chem. InL Ed.* 2014, 53, 1621-1625.
6. Field, J. J.; Waight, A. B.; Senter, P. D. A previously undescribed tubulin binder. *Proc. Natl. Acad. Sci. USA* 2014, 111, 13684-13685.
7. Prota, A. E.; Bargsten, K.; Diaz, J. F.; Marsh, M.; Cuevas, C.; Liniger, M.; Neuhaus, C.; Andreu, J. M.; Altmann, K. -H.; Steinmetz, M. O. A new tubulin-binding site and pharmacophore for microtubule-destabilizing anticancer drugs. *Proc. Natl. Acad. Sci. USA* 2014, 111, 13817-13821.
8. Gangjee, A.; Zhao, Y.; Lin, L.; Raghavan, S.; Roberts, E. G.; Risinger, A. L.; Hamel, E.; Mooberry, S. L. Synthesis and discovery of water-soluble microtubule targeting agents that bind to the colchicine site on tubulin and circumvent Pgp mediated resistance. *J. Med. Chem.* 2010, 53, 8116-8128.
9. Gangjee, A.; Choudhary, S.; Mooberry, S. L. Design, synthesis and biological evaluation of 6-amino-5-chloro-2-methyl N4-substituted pyrimidine analogs as potential anti-tubulin agents. Abstracts of Papers, 248th ACS National Meeting, San Francisco, Calif., United States, Aug. 10-14, 2014.
10. Kavallaris, M. Microtubules and resistance to tubulin-binding agents. *Nat. Rev. Cancer* 2010, 10, 194-204.
11. Nguyen, T. L.; McGrath, C.; Hermone, A. R.; Burnett, J. C.; Zaharevitz, D. W.; Day, B. W.; Wipf, P.; Hamel, E.; Gussio, R. A common pharmacophore for a diverse set of colchicine site inhibitors using a structural-based approach. *J. Med. Chem.* 2005, 48, 6107-6116.
12. Prota, A. E.; Danel. F.; Bachmann, F.; Bargsten, K.; Buey, R. M.; Pohlmann, J.; Reinelt, S.; Lane, H.; Steinmetz, M. O. The novel microtubule-destabilizing drug BAL27862 binds to the colchicine site of tubulin with distinct effects on microtubule organization. *J. Mol. Biol.* 2014, 426, 1848-1860.
13. Molecular Operating Environment (MOE 2013.0801); Chemical Computing Group, Inc.: Montreal, Quebec, Canada, 2013; www.chemcomp.com.

Section VI: Amide Bridged Pyrrolo[2,3-d]pyrimidine Antifolate Compounds

In the era of personalized drugs, an ideal antitumor agent only kills the tumor cells and has little damage to normal cells. The reduced folate carrier (RFC) is ubiquitously expressed in mammalian cells as the primary folates uptake transporter. However, some tumors overexpress folate receptors (FRs). The proton coupled folate receptor (PCFT) is another folate uptake transporter which functions best at an acidic pH environment such as that found in certain solid tumors. We demonstrated that antifolates which were selectively transported by FR and/or PCFT over RFC can be used as targeted antitumor agents. In this paper, we report the discovery of a novel series of targeted classical antifolates with an amide bridge between the pyrrolo[2,3-d]pyrimidines scaffold and the terminal glutamic acid. Among them, AGF238 with a methylene amide phenyl in the bridge, was selectively transported by FRα ($IC_{50}$=1.72 nM in R16 Chinese hamster ovary (CHO) cells) and PCFT ($IC_{50}$=40 nM in R2/PCFT4 CHO cells) over RFC. This compound was also found to exhibit highly potent antitumor activity ($IC_{50}$=0.6 nM in KB human tumor cells).

We synthesized our target compounds through the intermediate 6-aminomethyl pyrrolo[2,3-d]pyrimidines, which could be prepared by a Mannich reaction. However, direct Mannich reaction on pyrrolo[2,3-d]pyrimidines results in a highly polar and organic solvent-insoluble 6-aminomethyl pyrrolo[2,3-d]pyrimidine product, which made purification impractical. Here, we report a scalable and practical way to aminomethylate the pyrrolo[2,3-d]pyrimidines.

Introduction

Antifolates that inhibit the folate related enzymes or cofactors are important agents for anticancer chemotherapy. Despite the success of methotrexate (MTX), pralatrexate (PDX), raltitrexed (RTX) and pemetrexed (PMX) (FIG. 1) in hematologic malignancies and solid tumors treatments, dose limiting toxicities plague their clinic utility. These toxicities are most likely due to their cellular uptake into normal tissues, as well as into tumors, due to their uptake via the folate transporter mechanisms.[1] Section VI—FIG. 1 shows clinically used folate related cancer drugs.

There are three principal mechanisms of cellular uptake of (anti)folates. The reduced folate carrier (RFC) is an anion antiporter which is ubiquitously expressed in tissues and tumors. Other cellular uptake mechanisms include folate receptors (FRs) α and β and the proton-coupled folate transporter (PCFT). FRα is abundantly expressed on the membranes in several malignancies such ovarian cancer where it is exposed to the circulation, whereas in the few normal epithelial tissues where it is expressed (e.g., renal tubules), FRα is inaccessible to the circulation. This provides a compelling rationale for antifolate therapeutics which selectively target FRα. PCFT is a proton symporter that is expressed in a range of solid tumors, including ovarian cancer and non-small-cell lung cancer, and is highly active at the acidic pHs characteristic the solid tumor microenvironment. Although certain normal tissues also express PCFT, including the proximal small intestine, liver, and kidney, with the exception of the proximal small intestine, the pH of the microenvironments of most normal tissues are not conducive to PCFT transport.[2]

Although there are a number of FRα-targeted therapeutics, including [N-[4-[2-propyn-1-yl[(6S)-4,6,7,8-tetrahydro-2-(hydroxymethyl)-4-oxo-3H-cyclopenta[g]quinazolin-6-yl]amino]benzoyl]-L-γ-glutamyl-D-glutamic acid (ONX0801)], monoclonal antibody [farletuzumab (Morphotech)], cytotoxic folate conjugates [e.g., vintafolide (EC145; Endocyte)], all of which have been evaluated in clinic trials, to date no targeted antifolate has been FDA approved for clinical use with cancer.[3] Thus, novel antifolates that are selectively transported into tumors would afford a paradigm shift in cancer chemotherapy via targeted antifolates.
Rationale
Section VI—FIG. 2 shows the structure of Compound 1 and its two different docking poses in FRα and GARFTase, as well as designed compounds.

We[4] reported that the potent and targeted classical antifolate, 1, adopted two different docking poses in FRα and GARFTase (Section VI—FIG. 2). Literature[5] indicates that amides can adopt "pseudo-cis" and "pseudo-trans" orientations as the lowest energy interchangeable conformers. As such, classical antifolates with an amide linkage in the bridge presumably have the two lowest energy conformers. Molecular modeling (not shown) showed that the pseudo-cis amide is the best docked pose of 2 in FRα, and the pseudo-trans amide is the best docked pose of 2 in GARFTase. A N-methyl group was introduced on the amide nitrogen to increase the metabolic stability of the designed amide to hydrolysis.

We were also interested in a sulfonamide bridge compound 3 (Section VI—Table 1). The aromatic ring in the side chain plays an important role in the selectivity and potency and the antitumor activity of antifolates. Literature[6] suggests that replacing the phenyl ring in side chain with a thiophene could increase potency. Thus, the para- and meta-substituted phenyl, as well as different regioisomers of meta-substituted thiophene side chains 3-7 (Section VI—Table 1), were designed to explore optimization of the side chain for antitumor activity.

Chemistry

Currently, there are two available synthetic methods for 6-substituted classical antifolates.[1,5,6] The first method is using a Sonogashira coupling to link the pyrrolo[2,3-d]pyrimidines with aromatic side chains. This approach is not suitable for heteroatom side chain compounds. The second method is to cyclize a α-bromoketone with 2, 6-diamino-4-hydroxy pyrimidine to afford the pteroic acid precursor. This approach requires methane diazonium as one of the starting materials, which is dangerous. Hence, a new synthetic method was necessary for our proposed amide compounds.

The key intermediate in our synthetic method is 6-aminomethyl substituted pyrrolo[2,3-d]pyrimidine, which can form an amide or sulfonamide bond through simple amide or sulfonamide coupling reactions. Although utilizing the Mannich reaction to add an aminomethyl moiety to pyrrolo[2,3-d]pyrimidines has been established for more than fifty years,[7] at least three unsolved problems hinder its practical application. First, the 5- and 6-position regioselectivity of Mannich reaction on pyrrolo[2,3-d]pyrimidines is still open for debate due to different results from different research groups.[8,9] The highly polar and hydrophilic Mannich reaction product is the second obstacle. As a result, water based chromatography is the only currently available purification method. Finally, Mannich reaction on pyrrolo[2,3-d]pyrimidines gives tertiary amino products, which are difficult to functionalize.

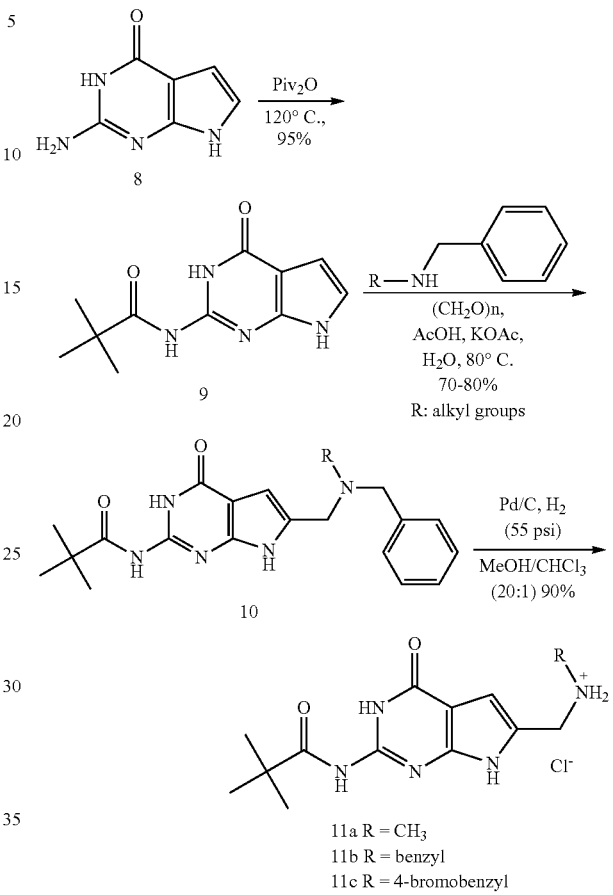

Scheme 1. Synthesis of N-monosubstituted (11) 6-amiomethyl pyrrolo[2, 3-d]pyrimidines.

11a R = CH₃
11b R = benzyl
11c R = 4-bromobenzyl

Our practical synthetic method for 6-aminomethyl pyrrolo[2,3-d]pyrimidine is shown in scheme 1. Pivaloylation of the 2-amino moiety of pyrrolo[2,3-d]pyrimidine 8 gave 9 (95% yield). The purpose of this step was to decrease the polarity and increase the solubility of 8. The product 9 directly precipitated from the reaction mixture by the addition of hexane and ethyl acetate (5:1). Mannich reaction on 9 afforded 10 in 70-80% yield. KOAc was used to form a buffer, at which pH the pivalic protection group was stabilized. Pd-catalyzed debenzylation of 10 provided 11 in 90% yield. None of these steps require chromatographic purification. For 10, after removal of the solvent and addition of acetone and filtration, the filtrate was distilled to afford a semisolid, crude 10, which can be directly used in the next step. For 11, filtration of the Pd/C and removal of the solvent, affords a residue that is washed with acetone to provide pure 11.

HMBC spectrum of 11a, was performed and the HMBC signals $^3J$ CH signals and $^2J$ CH signals were observed (not shown). In order to determine the regioselectivity of the Mannich reaction, compound 11a was analyzed by NOESY and HMBC. A weak NOE signal of $N^7$—H and 6'-H, which is probably due to the quadrupole $N^7$—H, in NOESY and the signal of $^3J(C^4$—$H^5)$, as well as $^3J(C^5$ or $C^9$—$H^3$ or $H^7)$ in HMBC (not shown), confirmed 11a with the amiomethyl substitution at the 6-position.

Scheme 2. Synthesis of 12a-f.

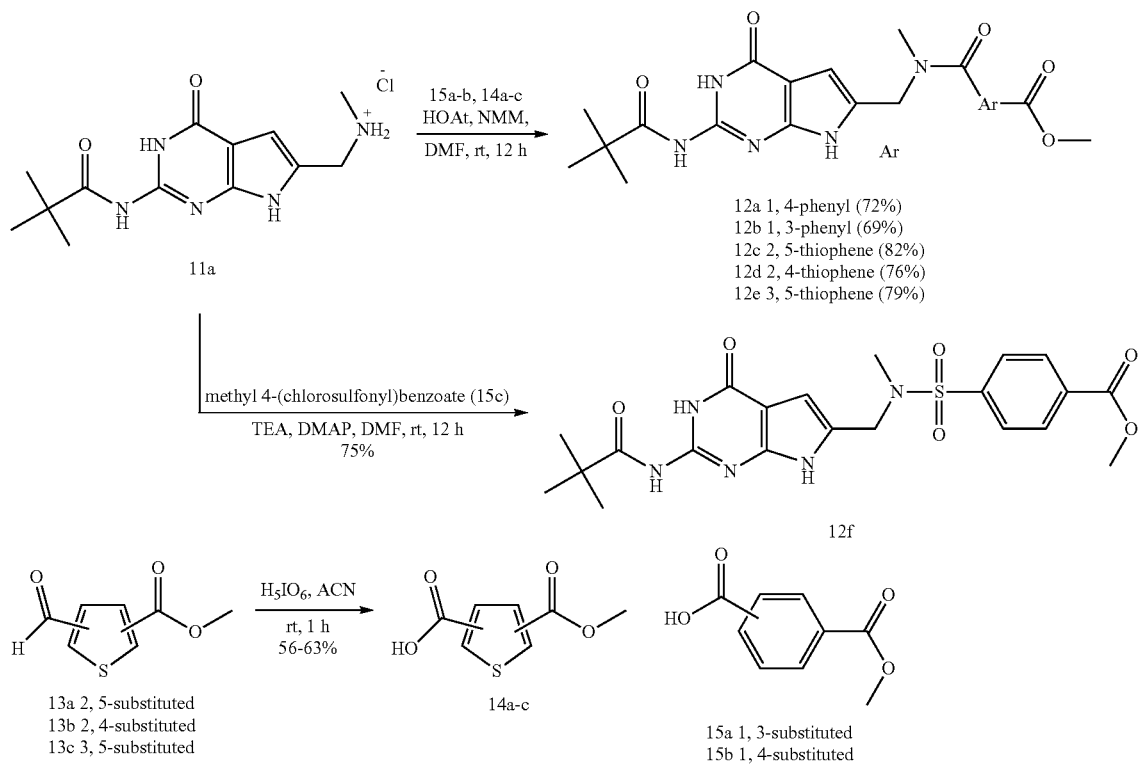

Amide or sulfonamide coupling of 11a with corresponding acid 15a-b, 14a-c or methyl 4-(chlorosulfonyl)benzoate 15c afforded 12a-f in 69-82% yield (Scheme 2). Compounds 14a-c were in turn synthesized by periodic acid oxidation of the appropriate aldehydes 13a-c in 56-63% yields.

Scheme 3. Synthesis of target compounds 2-7.

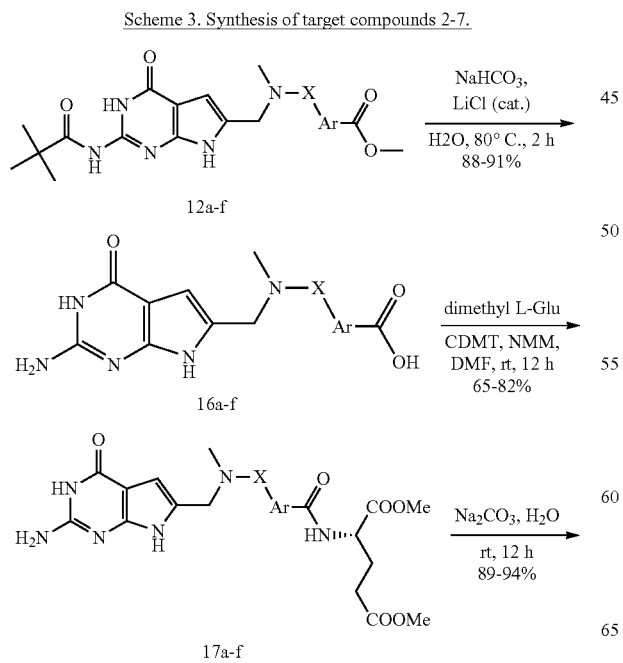

-continued

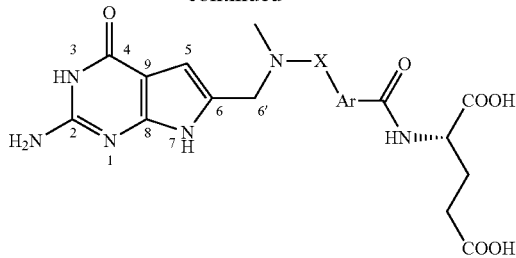

Depivaloylation and hydrolysis of the methyl esters in 12a-f with sodium bicarbonate and a catalytic amount of LiCl afforded pteroic acids 16a-f in 88-91% yields (scheme 3). CDMT auxiliary amide coupling of 16a-f with dimethyl L-glutamic acid afforded 17a-f in 65-82% yields. Sodium carbonate hydrolysis of 17a-f provided the target classical antifolates 2-7 in 90% yields.

Proton NMR of these compounds (12a-f, 16a-f, 17a-f, 2-7) showed two sets of peaks for the protons near the amide moiety (5-H, 6'-H and $6'^N$-CH$_3$) (Scheme 3) with the ratio around 6 to 4. This attested the two lowest energy conformers suggestion.

Biological Evaluation

Section VI-Table 1. Structures of 1-7 and the IC$_{50}$ values for inhibition of proliferation of FRα (RT16), FRβ (D4), PCFT (R2/PCFT4), and RFC (PC43-10)-expressing CHO cells and KB human tumor cells (expresses FRα, RFC, and PCFT) in culture. Abbreviations: MTX, methotrexate; PMX, pemetrexed; RTX, raltitrexed.

Section VI—

TABLE 1

Structure 1: 2-amino-4-oxo-pyrrolopyrimidine with propyl-thiophene-carboxamide-glutamic acid Structure 2-7: 2-amino-4-oxo-pyrrolopyrimidine-CH₂-N(CH₃)-X-C(O)-NH-glutamic acid

| X | FRα/PCFT/RFC (nM) KB | RFC (nM) PC43-10 | RFC (nM) R2 | FRα (nM) R16 | PCFT (nM) R2/PCFT4 | FRβ (nM) D4 |
|---|---|---|---|---|---|---|
| 1 | 0.20 | 101.0 | 289.0 | 0.19 | 3.64 | 0.20 |
| 2 (para-benzoyl) | 1.13 | >1000 | >1000 | 1.72 | 40 | 2.36 |
| 3 (para-phenylsulfonyl) | 674 | >1000 | >1000 | >1000 | >1000 | >1000 |
| 4 (meta-benzoyl) | 6.13 | >1000 | >1000 | 1.72 | 747 | 6.11 |
| 5 (2,5-thiophene carbonyl) | 4.28 | >1000 | >1000 | 7.92 | 873 | 21.8 |
| 6 (2,4-thiophene carbonyl) | 894 | >1000 | >1000 | >1000 | >1000 | >1000 |

TABLE 1-continued

| # | Structure | | | | | |
|---|---|---|---|---|---|---|
| 7 | (thiophene-acyl linker) | 38.87 | >1000 | >1000 | >1000 | >1000 |
| MTX | | 6.0 | 12 | 216) | 114 | 120.5 | 106 |
| PMX | | 68 | 138 | 894 | 42 | 13.2 | 60 |
| RTX | | 5.9 | 6.3 | >1000 | 15 | 99.5 | 22 |

Compounds 2-7 were tested in cell proliferation assays with a unique panel of isogenic Chinese hamster ovary (CHO) cell lines individually expressing RFC (PC43-10), PCFT (R2/PCFT4), FRα (RT16), or FRβ (D4), and results were compared to those for 1 and to standard antifolates without transporter selectivity. Negative controls for RFC- and PCFT-expressing cells included RFC-, FR-, and PCFT-null MTXRIIOua$^R$2-4 (R2) CHO cells [either the parental R2 subline or vector control R2(VC) cells, with identical results]; for the FR-expressing CHO cells, cells were treated with excess folic acid (200 nM) to block cellular uptake by FR as a negative control. The experiments with the CHO sublines were extended to KB human nasopharengeal carcinoma cells which express highly elevated FRα, along with RFC and PCFT. The results are summarized in Section VI-Table 1.

Compound 2 was slightly less active than 1 in KB human tumor cells which express FRα, PCFT and RFC, and in RT16 (FRα), D4 (FRβ) and R2/PCFT4 (PCFT) CHO cells. Whereas 1 showed a non-specific uptake component (see PC43-10; also seen in R2 cells), this was not seen with 2. The sulfonamide 3 was inactive against all the transporters. This indicates that the sulfonamide in the side chain either prevents uptake by this non-mediated process and/or does not inhibit folate metabolizing enzymes if taken up into cells. Regioisomer 4 was 30-fold less active than 1 in KB ($IC_{50}$=6.13 nM) and FR-β expressing CHO (D4) ($IC_{50}$=6.11 nM) cells, and 9-fold less active toward FRα expressing (RT16) CHO cells ($IC_{50}$=1.72 nM). This indicates that decreasing the distance between the scaffold and the L-glu moiety is detrimental to antitumor activity.

Isosteric replacement of the phenyl side chain with a thiophene ring resulted in decreased or a complete absence of activity. Among all three, compound 5 demonstrated activity in FRα-expressing KB ($IC_{50}$=4.28 nM) and CHO (RT16) ($IC_{50}$=7.92 nM) cells, and in FRβ-expressing CHO cells (D4) ($IC_{50}$=21.8 nM cells). 5 was inactive toward RFC-(PC43-10) and PCFT-(R2/PCFT4) expressing CHO cells. 7 was active toward KB cells ($IC_{50}$=38.87 nM) but was inactive toward the CHO sublines.

Figure 3:
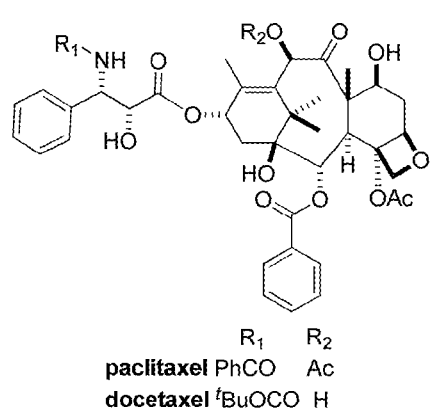
Figure 3:
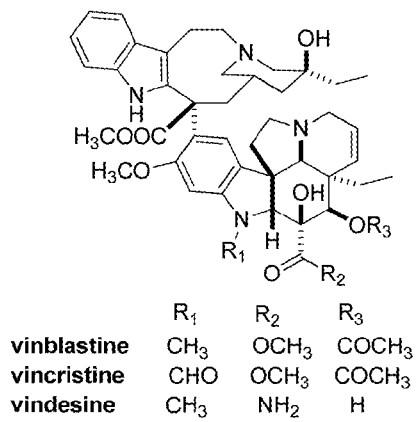
Figure 3:
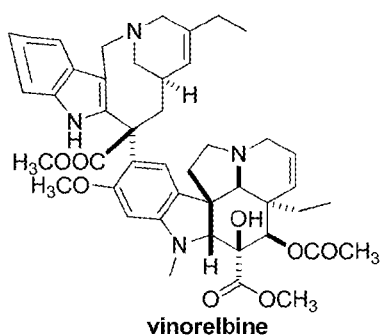
Figure 3:
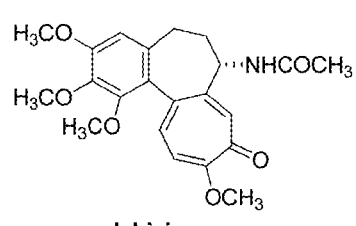
Figure 3:
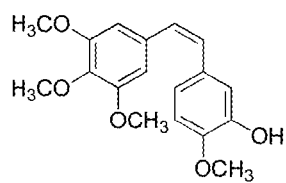
Figure 4:
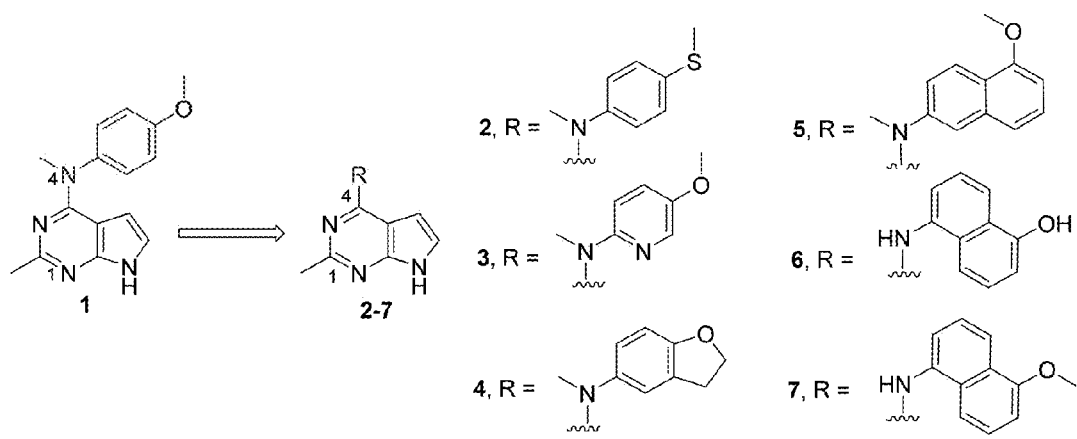
FIG. 4 (Section II—FIG. 2) shows the chemical structures of the microtubule inhibiting compounds 2-7 of this invention.
Figure 5:
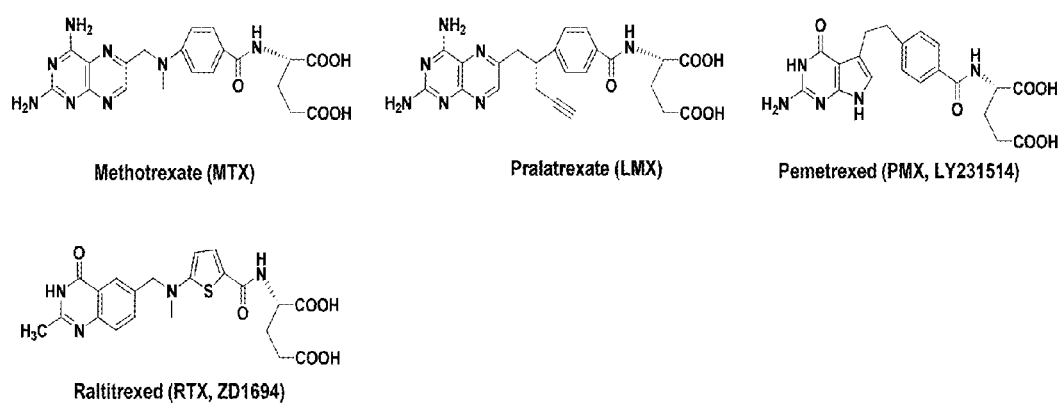
FIG. 5 (Section III—FIG. 1) shows the chemical structures of known antifolate compounds.
Figure 6:
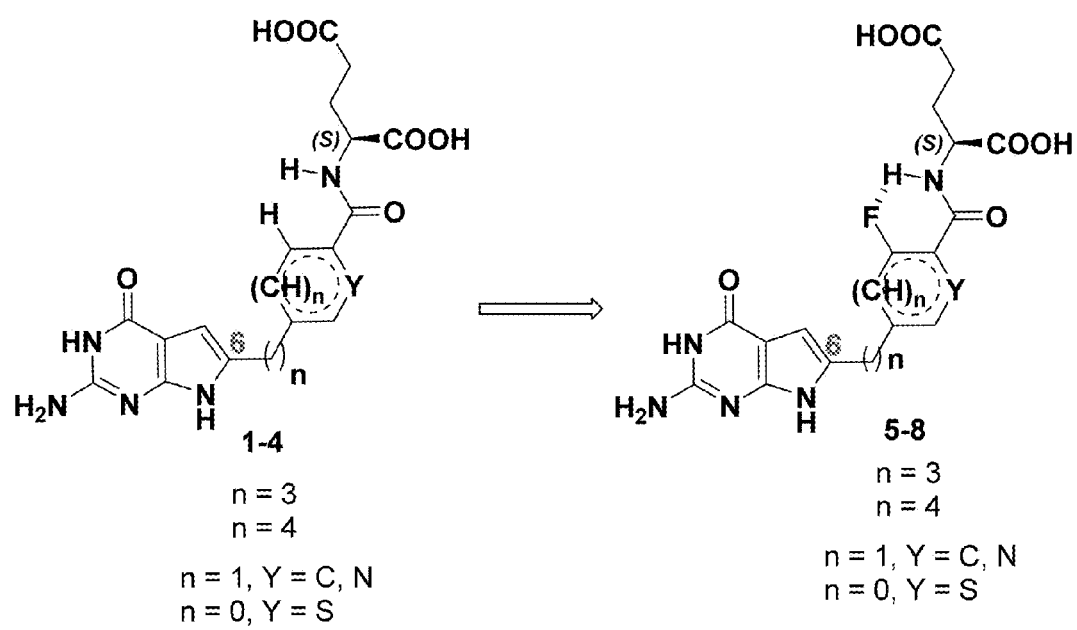
FIG. 6 (Section III—FIG. 2) shows the chemical structure of the antifolate compounds of this invention.
Figure 7:
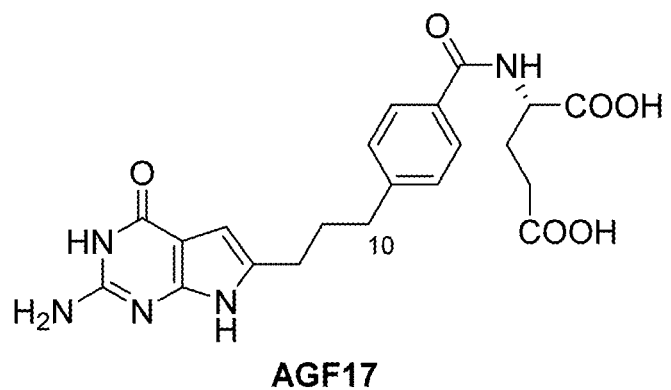
FIG. 7 (Section IV—FIG. 1) shows the chemical structure of compounds AGF233, 220, and 256 of this invention.
Figure 7:
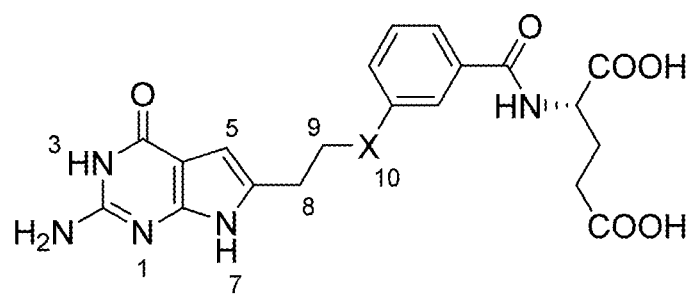
Figure 8:
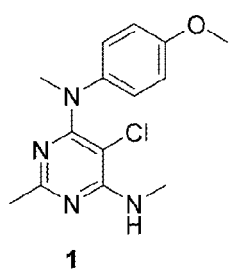
FIG. 8 (Section V—FIG. 1) shows the chemical structures of the compounds of this invention.
Figure 8:
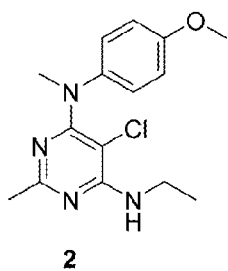
Figure 8:
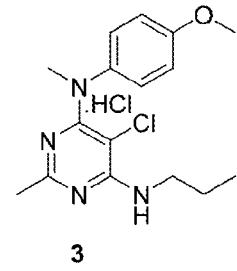
Figure 8:
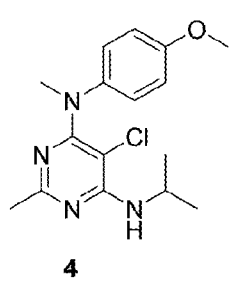
Figure 8:
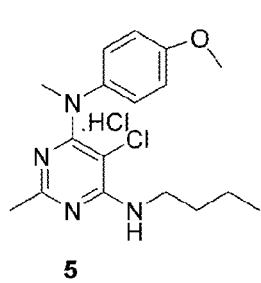
Figure 8:
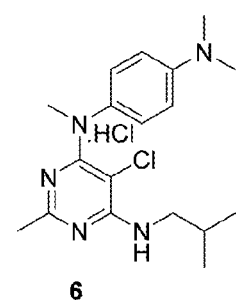
Figure 8:
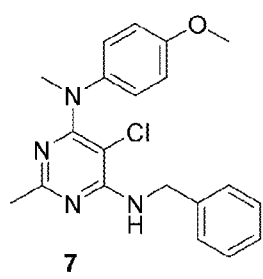
Figure 8:
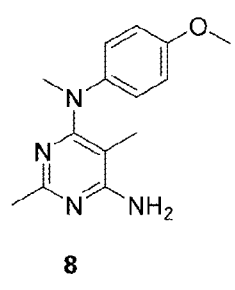
Figure 8:
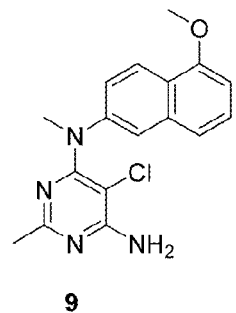
Figure 8:
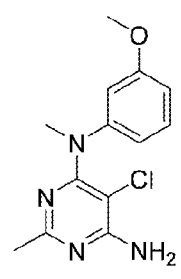
Figure 9:
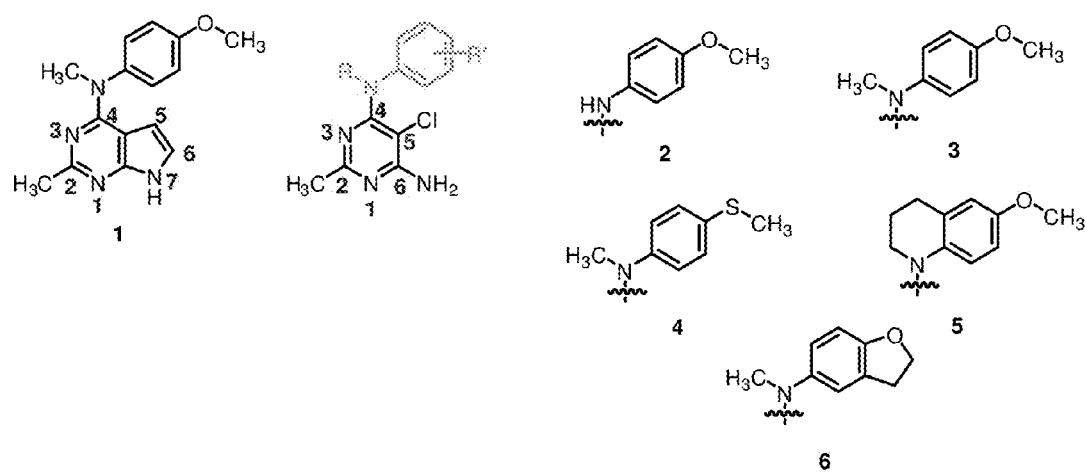
FIG. 9 (Section V—FIG. 2) shows the chemical structures of the compounds 2-6 of this invention wherein the moieties as set forth in compounds 2-6 are substituted for the nitrogen containing moiety of compound 1 at the fourth position carbon of the pyrimidine ring.
Figure 10:
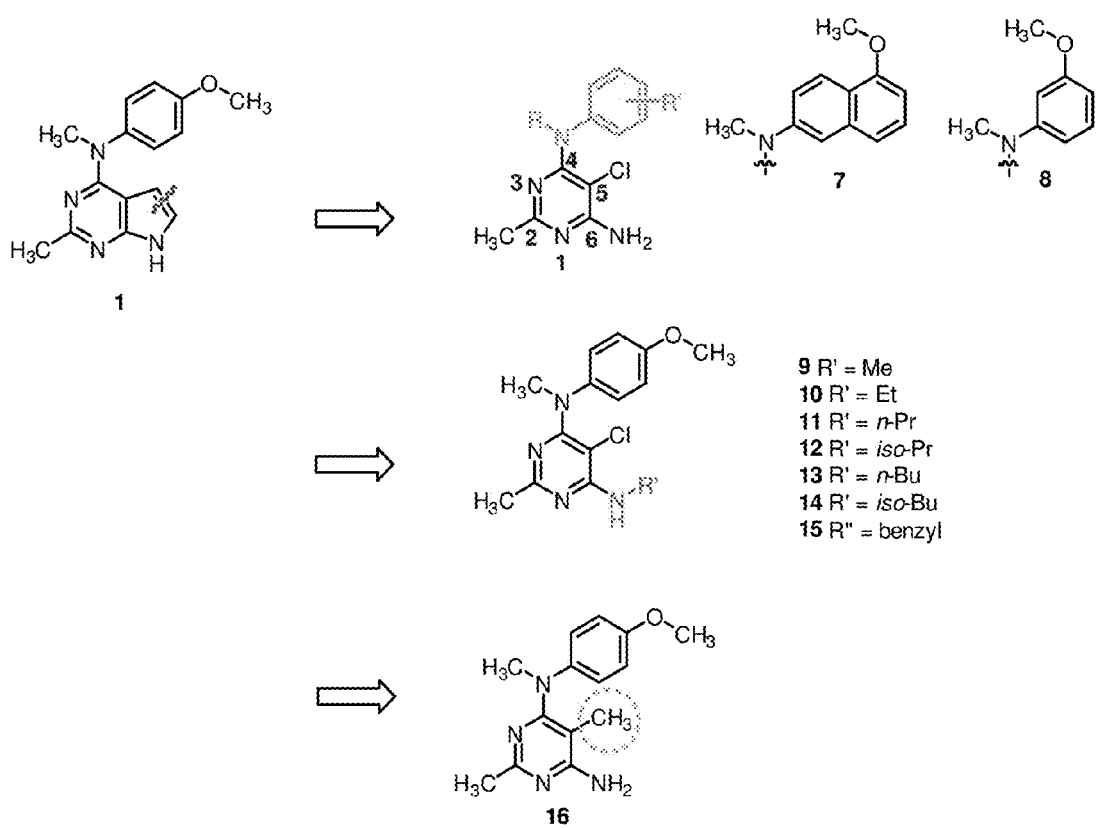
FIG. 10 (Section V—FIG. 3) shows the chemical structures of the pyrimidine analogs of this invention, wherein for the structures of compounds 7-8 of this invention the moieties as set forth in compounds 7-8 are substituted for the nitrogen containing moiety of compound 1 at the fourth position carbon of the pyrimidine ring.
Figure 11:
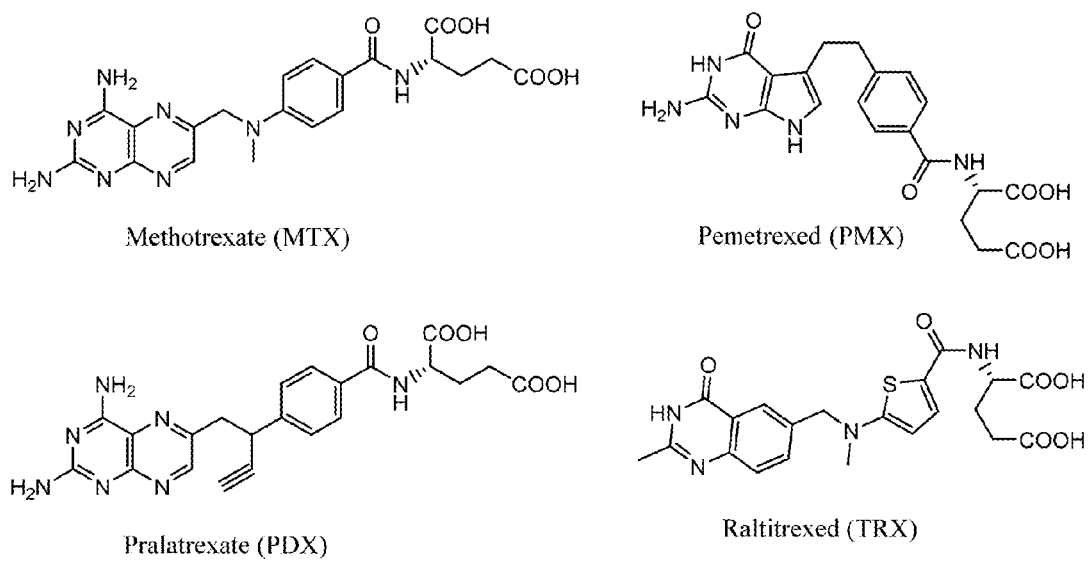
FIG. 11 (Section VI—FIG. 1) shows the chemical structures of clinically used cancer compounds.
Figure 12:
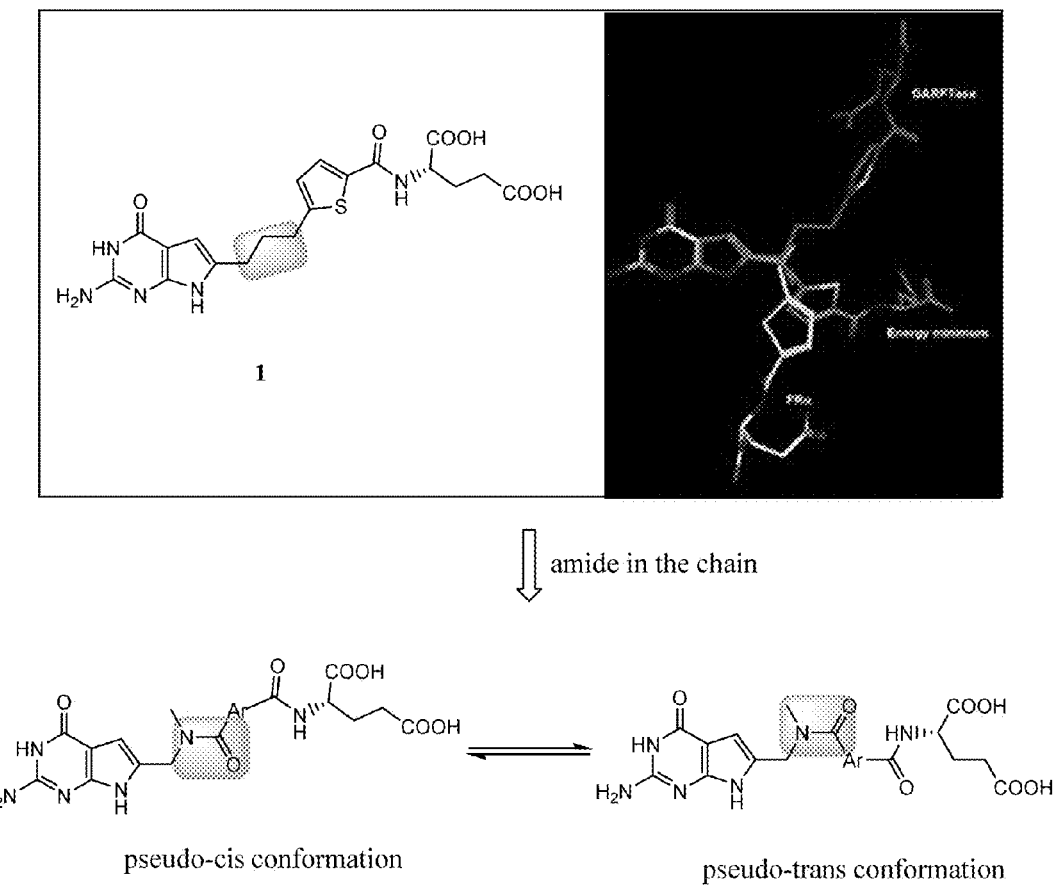
FIG. 12 (Section VI—FIG. 2) shows Compound 1 of Section VI and its two different docking poses and compounds of the present invention.
Figure 13:
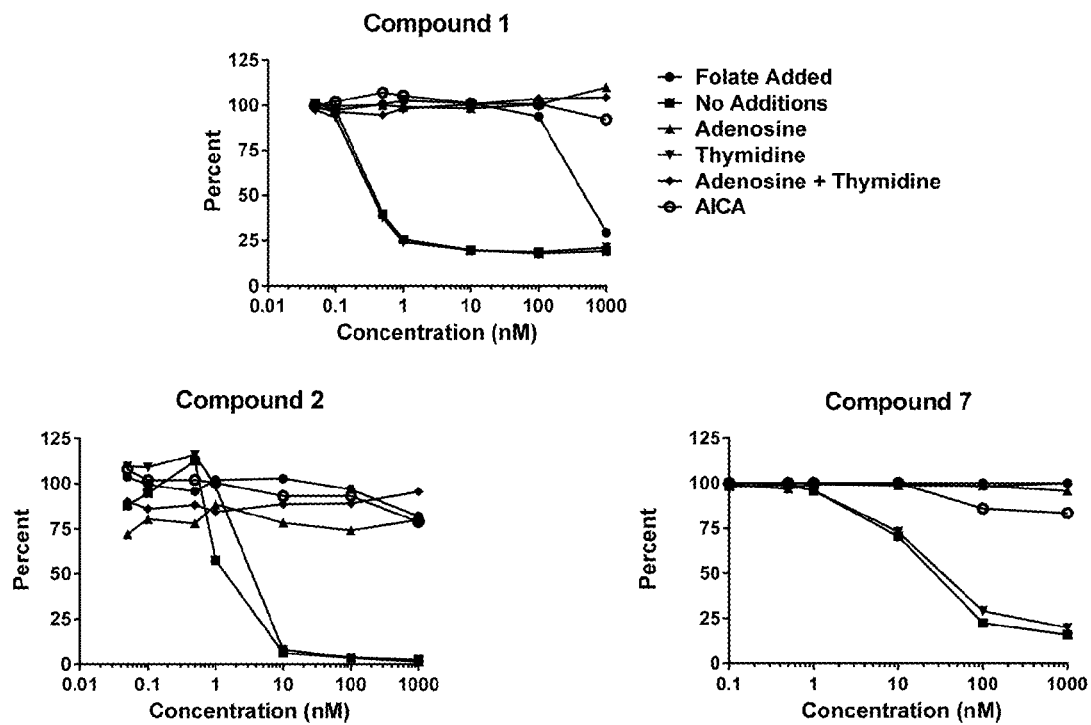
FIG. 13 (Section VI—FIG. 3) shows data for compound 1, and compounds 2 and 7 of this invention that support a de novo purine nucleotide biosynthesis as a targeted pathway.
Figure 14:
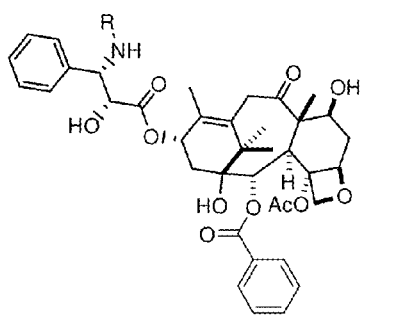
FIG. 14 (Section VII—FIG. 1) shows the chemical structures of known anti-cancer compounds.
Figure 14:
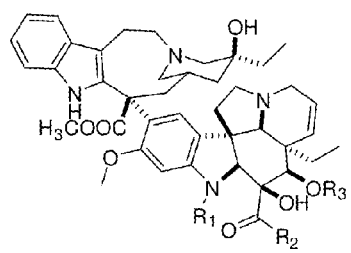
Figure 14:
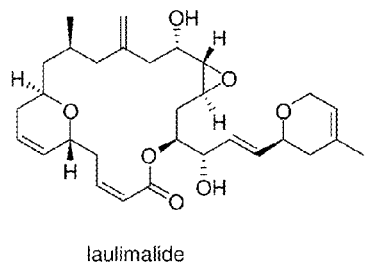
Figure 14:
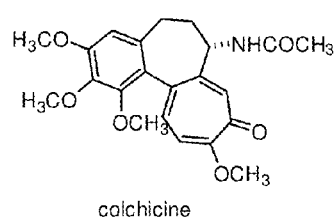
Figure 14:
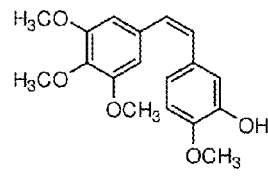
Figure 15:
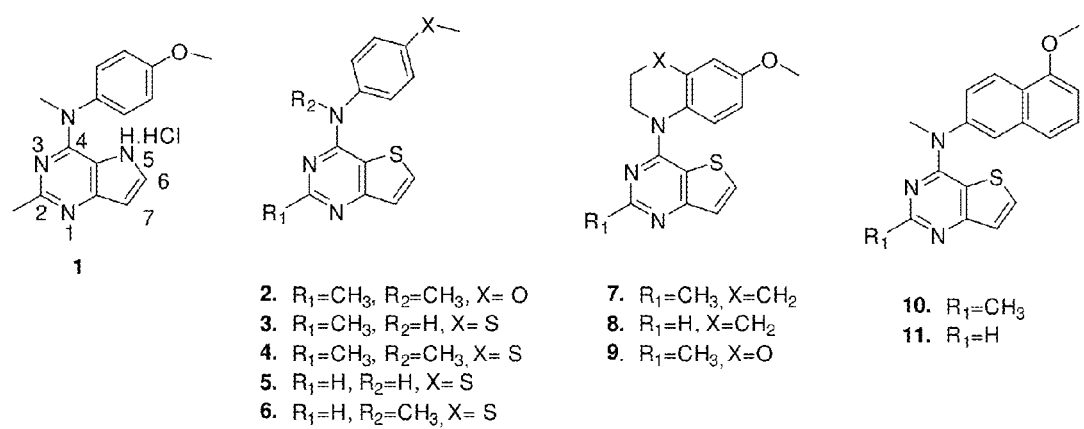
FIG. 15 (Section VII—FIG. 2) shows the chemical structures for compounds 2-11 of this invention.
Figure 16:
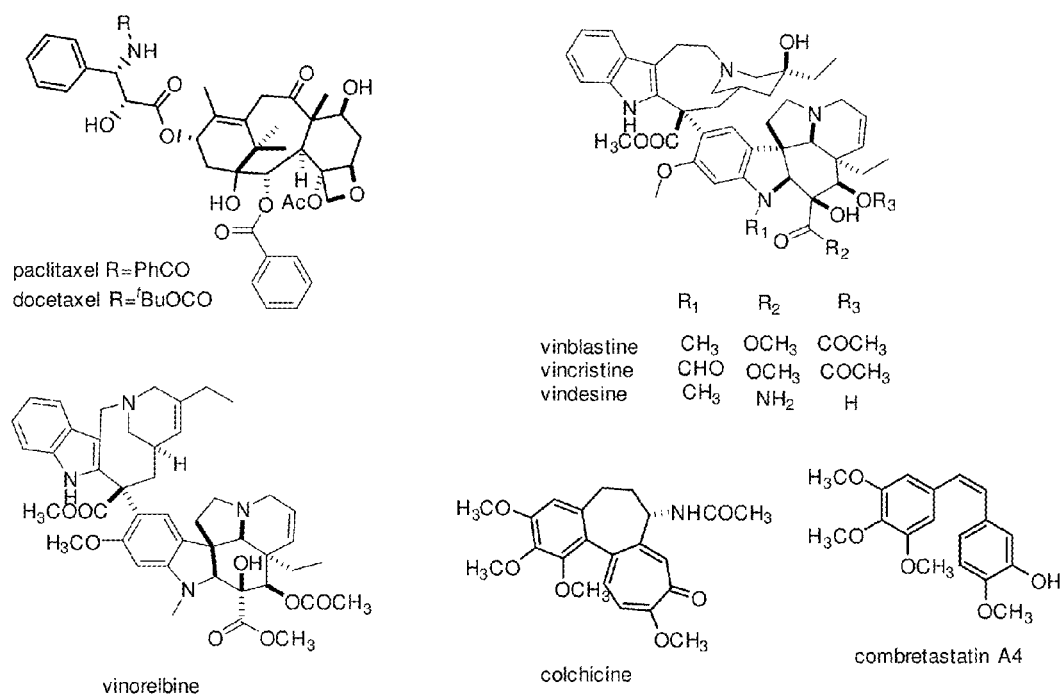
FIG. 16 (Section VIII—FIG. 1) shows the chemical structures of known vinca alkaloid compounds and colchicine site agents.
Figure 17:
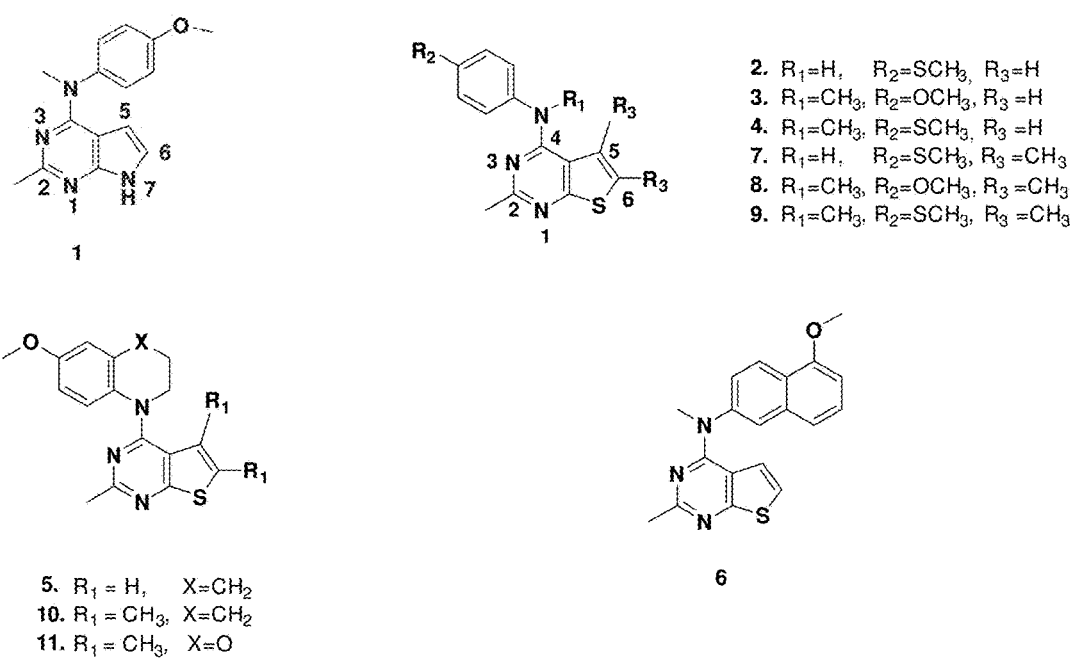
FIG. 17 (Section VIII—FIG. 2) shows the chemical structures of compounds 2-11 of the present invention.

Section VI—FIG. 3 shows nucleoside protection experiments, compounds 2, and 7, like 1, were completely protected by adenosine (60 μM) and 5-aminoimidazole-4-carboxamide (AICA) (320 μM) but not by thymidine (10 μM), establishing de novo purine nucleotide biosynthesis as the targeted pathway and glycinamide ribonucleotide formyl transferase (GARFTase) as the likely intracellular enzyme target.

Molecular Modeling

A docked pose (not shown) of 2 in FRα reveals an amide adopted pseudo-cis conformation. PDB ID: 4LRH. A docked pose (not shown) of 2 in GARFTase reveals an amide adopted pseudo-trans conformation. PDB ID: 4EW2. In an attempt to partially guide our design and explain the molecular basis of the potent activities of compound 2, we modeled it with FRα and GARFTase. The X-ray crystal structures of FRα (at 2.8 Å resolution; PDB ID 4LRH) and human GARFTase (at 1.60 Å resolution; PDB ID 4EW2) were obtained from the Protein Data Bank. The GARFTase crystal structure contains human GARFTase complexed with N-({4-[(1S)-4-(2,4-diamino-6-oxo-1,6-dihydropyrimidin-5-yl)-1-(methylsulfanyl)butyl]phenyl}carbonyl)-L-glutamic acid (10S-methylthio-DDACTHF) and FRα was co-crystallized with folic acid. Docking studies were performed using MOE (2013. 10).[10] The docked pose of 2 in FRα reveals 2 adopted the pseudo-cis conformation. The docked pose of 2 in GARFTase reveals 2 adopted the pseudo-trans conformation. The high activity of 2 in both FRα and GARFTase is a consequence of the ability of 2 to adopt different conformations dictated by the binding sites of the transporter (FRα) and the target enzyme (GARFTase).

Summary

Classical antifolates, including 1, adopt different low energy docking poses in FRα and GAFTase. We designed a series of classical antifolates with an amide in the bridge, which can adopt the pseudo-cis and pseudo-trans low energy conformations. Compound 2 when docked in FRα adopts the pseudo-cis conformation and in GARFTase the pseudo-trans conformation. Compound 2 was selectively transported by FRα and PCFT over RFC and showed potent antitumor activity towards FRα expressing KB human tumor cells.

In order to determine a convenient synthesis for the designed compounds, we discovered a practical method to the 6-aminomethyl pyrrolo[2,3-d]pyrimidine intermediate through a regiospecific Mannich reaction. This method does not require any chromatographic purification and easy provides scale up procedures for bulk synthesis. The aminomethyl at the 6-position of pyrrolo[2,3-d]pyrimidine was confirmed by HMBC.

This is a first in class of antifolates where the scaffold is bridged to the side chain aryl L-glutamate via an amide linkage that has absolute selectivity for transport via FRα, β and PCFT over RFC and possess efficacious antitumor activity in vitro.

Section VI References:
1. Wang, Y.; Mitchell-Ryan, S.; Raghavan, S.; George, C.; Orr, S.; Hou, Z.; Matherly, L. H.; Gangjee, A., Novel 5-Substituted Pyrrolo[2,3-d]pyrimidines as Dual Inhibitors of Glycinamide Ribonucleotide Formyltransferase and 5-Aminoimidazole-4-carboxamide Ribonucleotide Formyltransferase and as Potential Antitumor Agents. *Journal of Medicinal Chemistry* 2015, 58, 1479-1493.

2. Zhao, R.; Visentin, M.; Goldman, I. D., Determinants of the activities of antifolates delivered into cells by folate-receptor-mediated endocytosis. *Cancer chemotherapy and pharmacology* 2015, 75, 1163-73.
3. Assaraf, Y. G.; Leamon, C. P.; Reddy, J. A., The folate receptor as a rational therapeutic target for personalized cancer treatment. *Drug resistance updates: reviews and commentaries in antimicrobial and anticancer chemotherapy* 2014, 17, 89-95.
4. Golani, L. K.; George, C.; Zhao, S.; Raghavan, S.; Orr, S.; Wallace, A.; Wilson, M. R.; Hou, Z.; Matherly, L. H.; Gangjee, A., Structure—Activity Profiles of Novel 6-Substituted Pyrrolo[2,3-d]pyrimidine Thienoyl Antifolates with Modified Amino Acids for Cellular Uptake by Folate Receptors α and β and the Proton-Coupled Folate Transporter. *Journal of Medicinal Chemistry* 2014, 57, 8152-8166.
5. Avalos, M.; Babiano, R.; Barneto, J. L.; Cintas, P.; Clemente, F. R.; Jimenez, J. L.; Palacios, J. C., Conformation of secondary amides. A predictive algorithm that correlates DFT-calculated structures and experimental proton chemical shifts. *The Journal of organic chemistry* 2003, 68, 1834-42.
6. Wang, L.; Cherian, C.; Kugel Desmoulin, S.; Mitchell-Ryan, S.; Hou, Z.; Matherly, L. H.; Gangjee, A., Synthesis and Biological Activity of 6-Substituted Pyrrolo[2,3-d]pyrimidine Thienoyl Regioisomers as Inhibitors of de Novo Purine Biosynthesis with Selectivity for Cellular Uptake by High Affinity Folate Receptors and the Proton-Coupled Folate Transporter over the Reduced Folate Carrier. *Journal of Medicinal Chemistry* 2012, 55, 1758-1770.
7. West, R. A., 4-Hydroxypyrrolo[2,3-d]pyrimidine: Mannich Reaction. *The Journal of organic chemistry* 1961, 26, 4959-4961.
8. Hiroshi, A.; Eiko, E.; Takenori, H.; Hiroaki, M.; Susumu, M. Synthesis of queuine, the base of naturally occurring hypermodified nucleoside (queuosine), and its analog. *Journal of the Chemical Society, Perkin Transactions 1: Organic and Bio-Organic Chemistry* (1972-1999) 1998, (7), 1637-44.
9. Seela, Frank, S.; Chen, Y; Zulauf, M. Regioselectivity of the Mannich reaction on pyrrolo[2,3-d]pyrimidine nucleosides related to 7-deaza-2'-deoxyadenosine or 7-deaza-2'-deoxyguanosine. *Synthesis,* 1997, 9, 1067-1072.
10. mol_rmsd, Scientific Vector Language (SVL) source code provided by Chemical Computing Group Inc., 1010 Sherbooke St. West, Suite #910, Montreal, QC, Canada, H3A 2R7, 2013.10.

Section VII: Thieno[3,2-d]pyrimidines as Potent Antimitotic and Antitumor Agents Microtubles are a validated anticancer target. The taxanes and vinca alkaloids are clinically used drugs which act through disruption of cellular microtubules. However, multidrug resistance is a major drawback of these drugs. We have previously reported pyrrolo[3,2-d]pyrimidine (1) ($IC_{50}$=96.6 nM) as a potent water soluble inhibitor of proliferation of MDA-MB-435 cancer cells. Isosteric replacement of the pyrrole nitrogen in 1 provided thieno[3,2-d]pyrimidines which displayed improved antiproliferative potency in MDA-MB-435 cells. We have designed analogs with different substitutions at the 2 and N4-positions of the thieno[3,2-d]pyrimidine scaffold to explore the SAR and further improve the antiproliferative activities of these compounds. The design, synthesis and biological activities of these analogs is set forth herein.

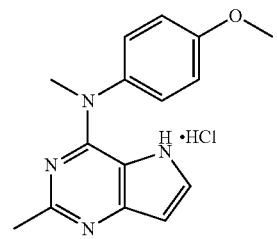

1

Section VII—Table 1:

TABLE 1

| | | sets forth the structures of the compounds of the present invention: | | | |
|---|---|---|---|---|---|
| Compound no. in poster | Compound no. | Structure | $IC_{50}$ ± SD in MDA-435 Cells | $EC_{50}$ for Microtubule Depolymerization in A · 10 Cells | $EC_{50}/IC_{50}$ Ratio |
| 1. | RP/AG/159-124 AG85* | ![structure] | 96.6 ± 5.3 nM | 1.2 µM | 12 |

TABLE 1-continued sets forth the structures of the compounds of the present invention:

| Compound no. in poster | Compound no. | Structure | $IC_{50} \pm SD$ in MDA-435 Cells | $EC_{50}$ for Microtubule Depolymerization in A · 10 Cells | $EC_{50}/IC_{50}$ Ratio |
| --- | --- | --- | --- | --- | --- |
| 2. | XLZ/AG/156-376 AG95 | 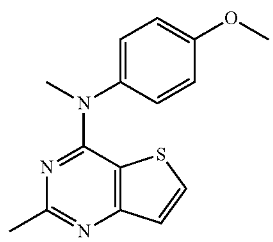 | $7.0 \pm 2.7$ nM | 27 nM | 3.7 |
| 3. | TQ/AG/175-112 AG326 | 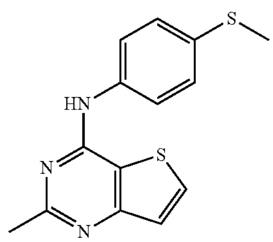 | $2.1 \pm 0.07$ μM | 25 μM | 12 |
| 4. | TQ/AG/175-113 AG327 | 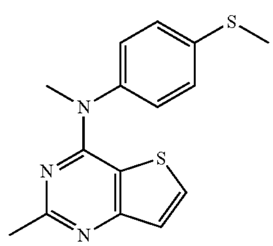 | $4.4 \pm 0.2$ nM | 42 nM | 9.5 |
| 5. | KS/AG/174-214 AG308 | 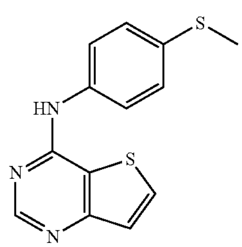 [SMILES: CSc1ccc(Nc2ncnc3ccsc23)cc1] | ND | >10 μM | — |
| 6. | KS/AG/174-176 AG310 | 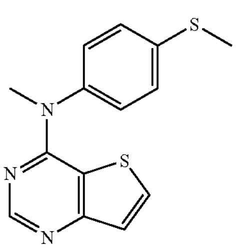 [SMILES: CSc1ccc(N(C)c2ncnc3ccsc23)cc1] | $28.2 \pm 5.5$ nM | 707 nM | 25 |
| 7. | TQ/AG/175-114 AG337 | 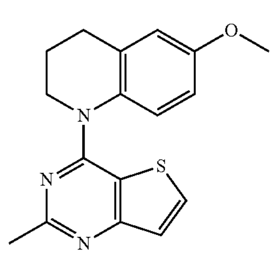 | $3.4 \pm 0.9$ nM | 8 nM | 2.4 |

TABLE 1-continued sets forth the structures of the compounds of the present invention:

| Compound no. in poster | Compound no. | Structure | $IC_{50} \pm$ SD in MDA-435 Cells | $EC_{50}$ for Microtubule Depolymerization in A·10 Cells | $EC_{50}/IC_{50}$ Ratio |
|---|---|---|---|---|---|
| 8. | KS/AG/174-221 AG309 | 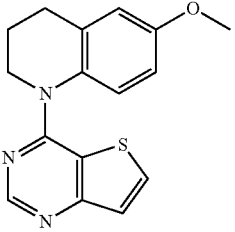 [SMILES: COc1ccc2c(c1)CCCN2c1ncnc2ccsc12] | $3.8 \pm 0.3$ nM | 22 nM | 5.8 |
| 9. | TQ/AG/175-115 | 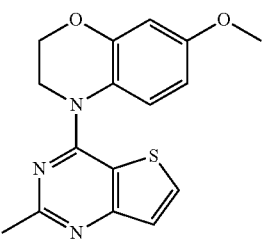 | 109 nM | 237 nM | 2.2 |
| 10. | TQ/AG/175-111 AG325 | 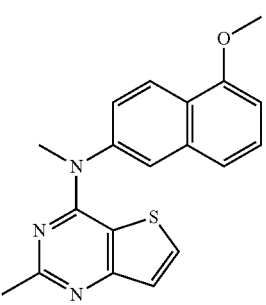 | $1.7 \pm 0.2$ nM | 3 nM | 1.8 |
| 11. | KS/AG/174-265 AG334 | 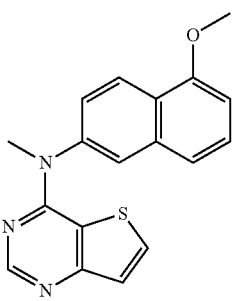 [SMILES: COc1cccc2cc(N(C)c3ncnc4ccsc34)ccc12] | $15.7 \pm 2.2$ nM | 61 nM | 3.9 |

Microtubule play central roles in many cellular processes including mitosis as well as the trafficking of many cellular constituents including organelles. The ability to disrupt these processes can impact cell proliferation and survival. Agents that target microtubules have found significant utility in treating cancer, however innate and acquired drug resistance and significant side effects limits the utility of many microtubule targeting drugs. The identification of new agents with superior properties provides an opportunity for overcoming the limitations of the existing drugs. MTAs are classified into two groups, microtubule-stabilizing agents (MSA) and microtubule-destabilizing agents (MDA).[2] Taxanes belong to the first group which bind to the interior of the microtubule. They are useful against breast, lung, ovarian and prostate carcinomas.[3] Laulimalide and peloruside A also belong to the first group which bind to the laulimalide site, a unique non-taxane site in β-tubulin located on the exterior of the microtubule.[4] Vinca alkaloids such as vincristine and vinblastine are microtubule destabilizers. These are β-tubulin binding agents used in leukemias, lymphomas and other cancers.[3] Rhizoxin and maytansine bind to the maytansine site in β-tubulin.[5] Colchicine site agents consist of a diverse collection of molecules which bind at the β-tubulin at its interface with α-tubulin.[1] These are also MDAs. Combretastatin A-4 (CA4) and its phosphorylated analog combretastatin A-4 phosphate (CA4-P) bind to the colchicine site on tubulin are currently in clinical trials. There are no approved colchicine site agents.[5] This suggests the need for developing colchicine site antitumor agents in order to determine the importance of these agents in the clinic. Section VII—FIG. 1 shows the structures of know agents.

Mutation in the p53 gene occurs in half of all tumors and MTAs are some of the most effective agents for treating p53 mutant cells.[7] Multidrug resistance (MDR) is a major limitation in cancer chemotherapy, and MDR tumors are particularly resistant to tubulin-binding agents.[8] Overexpression of P-glycoprotein (Pgp) has also been reported in a number of tumor types.[9] Attempts to reverse drug resistance by combining MTAs with inhibitors of drug efflux proteins produced disappointing results.[2] Expression of β-III tubulin is another clinical mechanism of resistance to tubulin binding agents in several tumor types including non-small cell lung,[10] breast[11] and ovarian cancer.[12] Stengel et al.[13] showed that colchicine site agents are the most effective agents against β-III tubulin resistance which further implicates the importance of developing this class of agents. Section VII—FIG. 2 shows the chemical structures of compounds 2-11 of the present invention.

The present invention provides the following compounds:

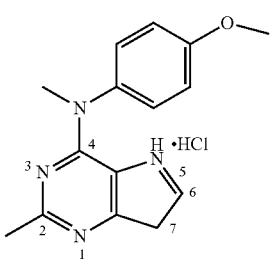

1

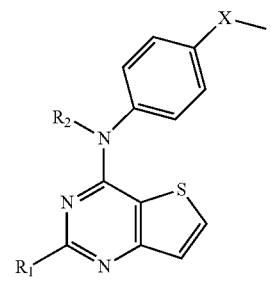

2. $R_1 = CH_3$, $R_2 = CH_3$, $X = O$
3. $R_1 = CH_3$, $R_2 = H$, $X = S$
4. $R_1 = CH_3$, $R_2 = CH_3$, $X = S$
5. $R_1 = H$, $R_2 = H$, $X = S$
6. $R_1 = H$, $R_2 = CH_3$, $X = S$

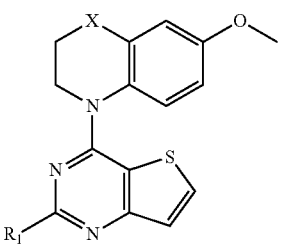

7. $R_1 = CH_3$, $X = CH_2$
8. $R_1 = H$, $X = CH_2$
9. $R_1 = CH_3$, $X = O$

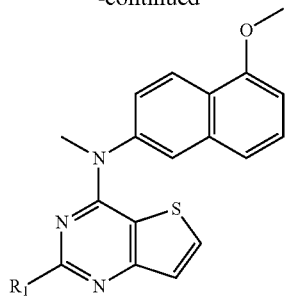

10. $R_1 = CH_3$
11. $R_1 = H$

In 2012, Gangjee et al.[14] reported pyrrolo[3,2-d]pyrimidine 1 as an inhibitor of the proliferation of human cancer cells (MDA-MB-435). Compound 1 inhibits the growth of cancercells with $Ic_{50}$ values in the nanomolar range and also circumvents Pgp and βIII-tubulin mediated resistance mechanisms that limit the activity of several microtubule targeting agents.[14] In this study an isosteric replacement of the scaffold and substituents at the 2-, 4- and 4'-positions were synthesized (2-11). The pyrrole nitrogen was isosterically replaced to provide thieno[3,2-d]pyrimidines, where the bicyclic scaffold size was increased. The replacement also removes a hydrogen bond donor (N5-H) which was expected to improve the lipophilicity of the scaffold. Variations of the 2-position of the scaffold were explored with 2-desmethyl analogs of the compounds (5, 6, 8 and 11). The 4'-methoxy group of the aniline ring was also isosterically replaced with a thiomethyl group to explore the importance of oxygen of the methoxy group. Finally, tetrahydroquinoline (7, 8) and naphthyl rings (10, 11) were introduced to replace the aniline and phenyl rings respectively, which could provide information regarding these rings and biological activity. Molecular modeling using MOE suggests that, in this series of compounds the naphthyl ring compound 10 orients the molecule for optimum interaction with the colchicine site of tubulin. Docked pose of 10 has a docking score of −7.45 kcal/mol whereas 1 scores −6.9 kcal/mol.

Molecular Modeling

Superimposition of the docked poses of 1, 10, and colchicine in the colchicine site of tubulin at the interface of the α-subunit and the β-subunit of tubulin was performed (not shown). PDB:4O2B[15]

Scheme 1:

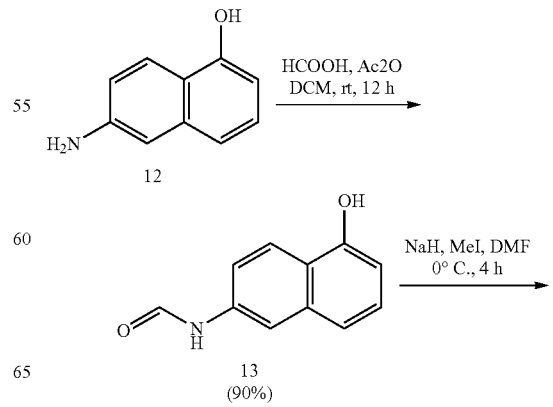

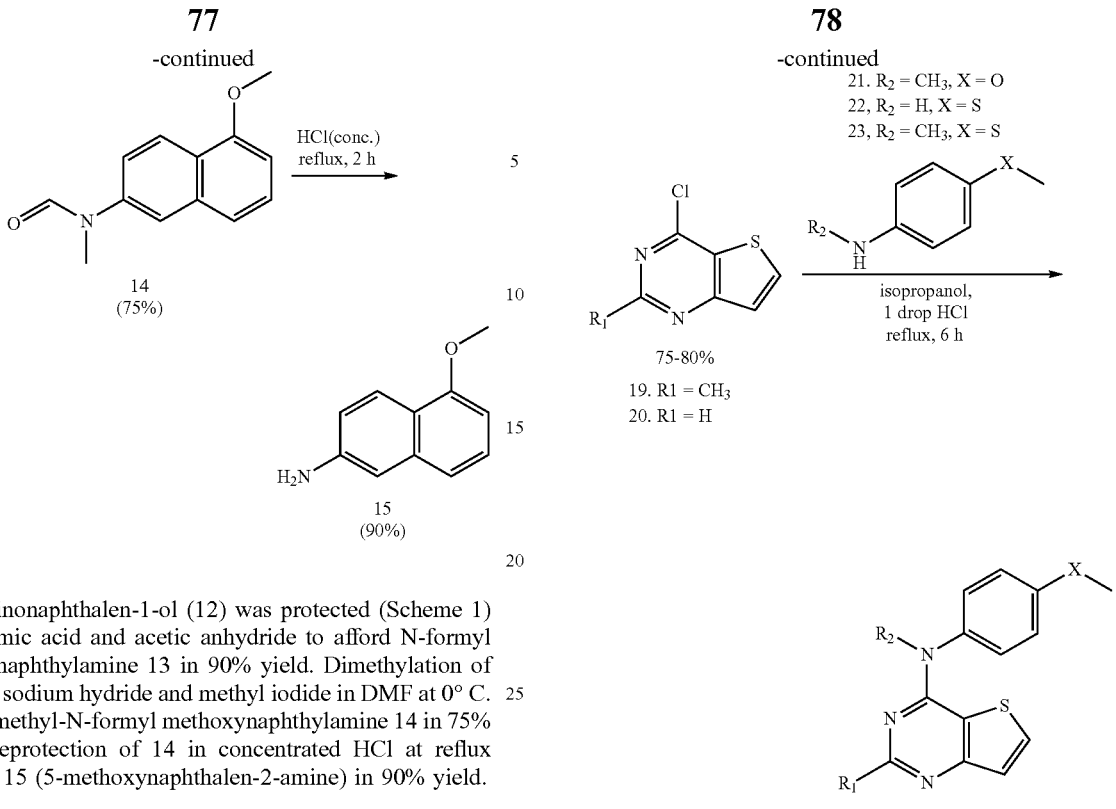
6-Aminonaphthalen-1-ol (12) was protected (Scheme 1) with formic acid and acetic anhydride to afford N-formyl hydroxynaphthylamine 13 in 90% yield. Dimethylation of 13 using sodium hydride and methyl iodide in DMF at 0° C. gave N-methyl-N-formyl methoxynaphthylamine 14 in 75% yield. Deprotection of 14 in concentrated HCl at reflux afforded 15 (5-methoxynaphthalen-2-amine) in 90% yield.
Scheme 2:
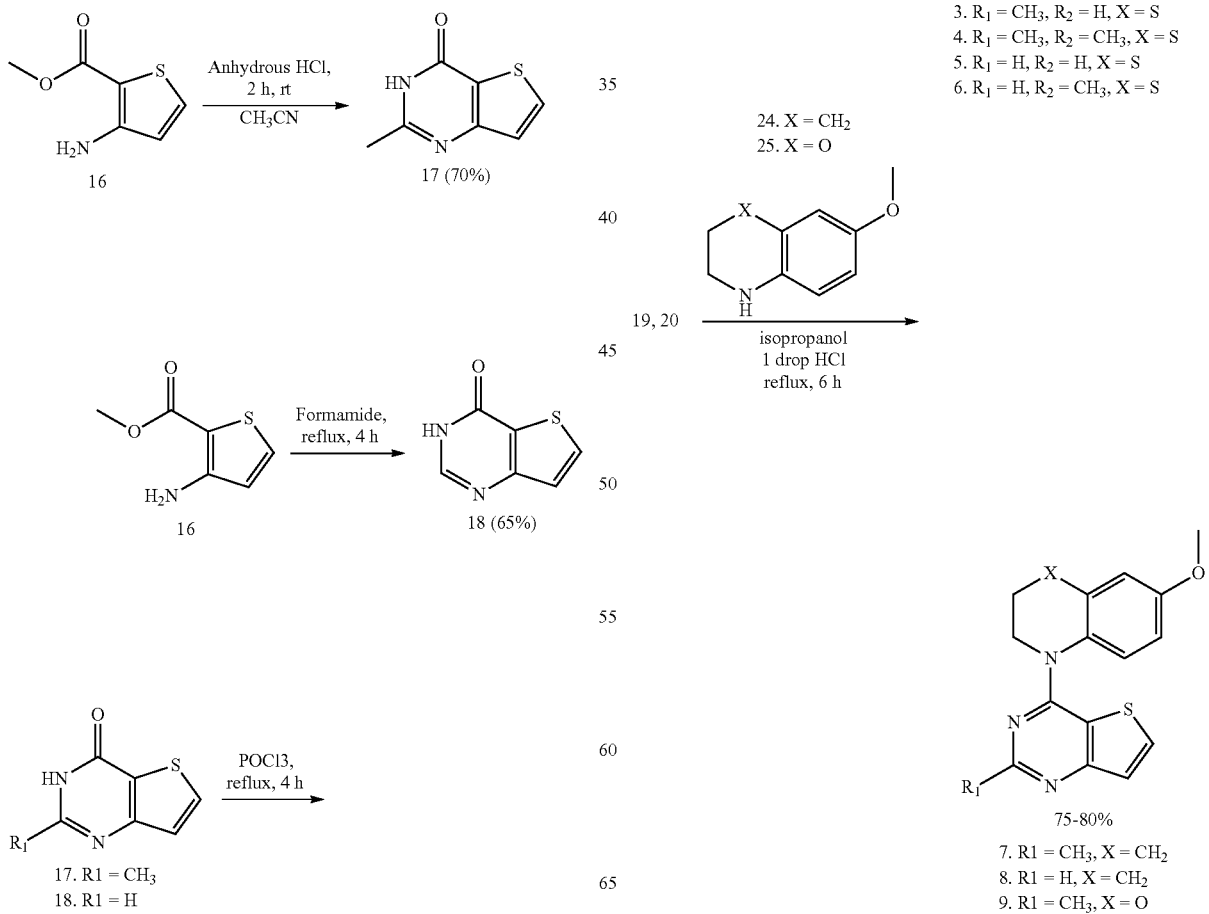

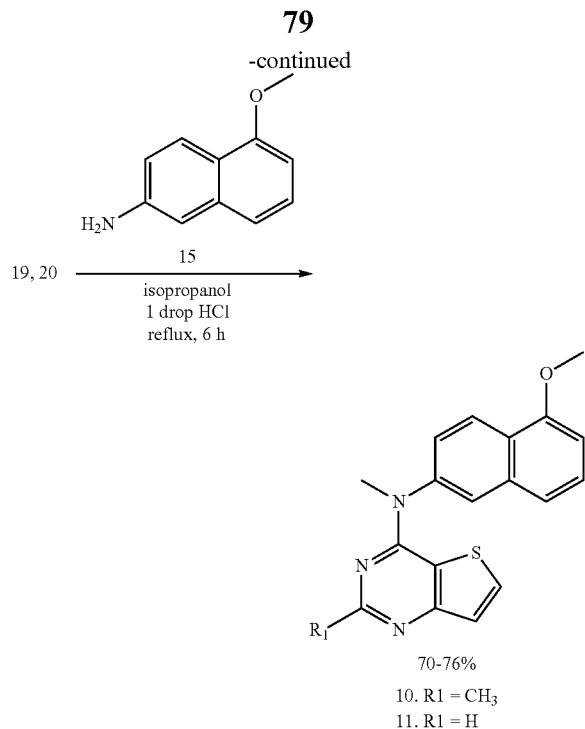

Commercially available methyl 3-aminothiophene-2-carboxylate 16 was cyclized (Scheme 2) with acetonitrile in presence of anhydrous HCl gas to afford 17 in 70% yield. Compound 16 was cyclized with formamide at reflux to afford 18 in 65% yield. Chlorination of 17 and 18 with $POCl_3$ at reflux afforded 4-chlorothieno[3,2-d]pyrimidin 19 and 20 in 75-80% yield. Nucleophilic displacement of 19 and 20 by various arylamines 21-25 and 15 afforded target compounds 2-11 in 70-84% yield.

Biological Activity
Section VII—Table 2:

TABLE 2

$IC_{50}$ values for inhibition of proliferation of MDA-MB-435 Cells and Effect on Microtubule Polymerization

| Compound No. | $IC_{50}$ ± SD (MDA-MB-435) Tumor cells | $EC_{50}$ in A-10 cells (Tubulin polymerization inhibitory activity) | $EC_{50}/IC_{50}$ Ratio |
|---|---|---|---|
| 1 | 96.6 ± 5.3 nM | 1.2 μM | 12 |
| 2 | 7.0 ± 2.7 nM | 27 nM | 3.7 |
| 3 | 2.1 ± 0.07 μM | 25 μM | 12 |
| 4 | 4.4 ± 0.2 nM | 42 nM | 9.5 |
| 5 | ND | >10 μM | — |
| 6 | 28.2 ± 5.5 nM | 707 nM | 25 |
| 7 | 3.4 ± 0.9 nM | 8 nM | 2.4 |
| 8 | 3.8 ± 0.3 nM | 22 nM | 5.8 |
| 9 | | 237 nM | |
| 10 | 1.7 ± 0.2 nM | 3 nM | 1.8 |
| 11 | 15.7 ± 2.2 nM | 61 nM | 3.9 |

Compounds 1-11 were tested for antiproliferative effects against the MDA-MB-435 cancer cells in culture using sulforhodamine B assay (SRB assay). Microtubule disrupting effects of 1-11 were evaluated in a cell-based phenotypic assay. The data suggest that, isosteric replament of the pyrrole nitrogen with sulfur affords 2 that is 14-fold more potent than 1, but importantly 44-fold more potent at causing cellular microtubule loss. Compound 10, which has a methoxy substitution on the aminonaphthyl ring has the best activity in this series, both for inhibition of proliferation and for causing microtubule depolymerization. In this compound, the naphthyl ring orients the methoxy group in a position, which is highly conducive to bind at the colchicine site of tubulin. Thiomethyl substitution retains activity in the series. The $N4-CH_3$ moiety is crucial for microtubule targeting and antiproliferative activity. Further, the $2-CH_3$ group shows improved activity compared to the 2-desmethyl analogs in the series (5,6,8,11). In general the thieno[3,2-d]pyrimidine scaffold affords excellent inhibitory activity against cancer cells in culture as well as the loss of cellular microtubules. Compounds 3, 7 and 8 match the cancer cell inhibition of CA4 and 10 supersedes CA4.

Section VII References:
1. Jordan, M. A.; Wilson, L. Microtubules as a Target for Anticancer Drugs. *Nat. Rev. Cancer* 2004, 4, 253-265.
2. Dumontet, C; Jordan, M. A. Microtubule-binding agents: A Dynamic Field of Cancer Therapeutics *Nat. Rev. Drug Discov.* 2010, 9, 790-803.
3. Jordan, M. A.; Kamath, K. How do Microtubule-Targeted Drugs Work? An Overview. *Curr. Cancer Drug Targets* 2007, 7, 730-742.
4. Prota, A. E.; Bargsten, K.; Northcote P. T.; Marsh M.; Altmann K. H.; Miller J. H.; Diaz J. F.; Steinmetz M. O. Structural Basis of Microtubule Stabilization by Laulimalide and Peloruside A. *Angew. Chem. Int. Ed.* 2014, 53, 1621-1625
5. Prota, A. E.; Bargsten, K.; Diaz J. F.; Marsh M.; Cuevas C.; Liniger, M.; Neuhaus, C.; Andreu, J. M.; Altmann K. H.; Miller J. H.; Steinmetz M. O. A new tubulin binding site and pharmacophore for microtubule-destabilizing anticancer drugs. *Proc. Natl. Acad. Sci. U.* 2014, 111, 13817-13821
6. Carlson, R. O. New Tubulin Targeting Agents Currently in Clinical Development. *Expert Opin. Investig. Drugs* 2008, 17, 707-722.
7. Kavallaris, M. Microtubules and resistance to tubulin-binding agents. *Nat. Rev. Cancer,* 2010, 3, 194-204.
8. Ling, V. Multidrug Resistance: Molecular Mechanisms and Clinical Relevance. *Cancer Chemother.* 1997, 40, S3-8.
9. Chiou, J. F.; Liang, J. A.; Hsu, W. H.; Wang, J. J.; Ho, S. T.; Kao, A. Comparing the Relationship of Taxol-based Chemotherpay Response with P-glycoprotein and Lung Resistance-related Protein Expression in Non-Small Cell Lung Cancer. *Lung* 2003, 181, 267-273.
10. Seve, P.; Isaac, S.; Tredan, O.; Souquet, P.-J.; Pacheco, Y.; Perol, M.; Lafanechere, L.; Penet, A.; Peiller, E.-L.; Dumontet, C. Expression of Class III β-Tubulin Is Predictive of Patient Outcome in Patients with Non-Small Cell Lung Cancer Receiving Vinorelbine-Based Chemotherapy. *Clin. Cancer Res.* 2005, 11, 5481-5486.
11. Tommasi, S.; Mangia, A.; Lacalamita, R.; Bellizzi, A.; Fedele, V.; Chiriatti, A.; Thomssen, C.; Kendzierski, N.; Latorre, A.; Lorusso, V.; Schittulli, F.; Zito, F.; Kavallaris, M.; Paradiso, A. Cytoskeleton and Paclitaxel Sensitivity In Breast Cancer: The Role Of Beta-Tubulins. *Int. J. Cancer* 2007, 120, 2078-2085.
12. Ferrandina, G.; Zannoni, G. F.; Martinelli, E.; Paglia, A.; Gallotta, V.; Mozzetti, S.; Scambia, G.; Ferlini, C. Class III β-Tubulin Overexpression Is A Marker Of Poor Clinical Outcome In Advanced Ovarian Cancer Patients. *Clin. Cancer Res.* 2006, 12, 2774-2779.
13. Stengel, C; Newman, S. P.; Lesse, M. P.; Potter, B. V. L.; Reed, M. J.; Purohit, A. Class III Beta-Tubulin Expression and in vitro Resistance To Microtubule Targeting Agents. *Br. J. Cancer* 2010, 102, 316-324.
14. Gangjee, A.; Pavana, R. K.; Li, W.; Hamel, E.; Westbrook, C.; Mooberry S. L. Novel Water-Soluble Substituted Pyrrolo[3,2-d]pyrimidines: Design, Synthesis and Biological Evaluation as Antitubulin Antitumor Agents. *Pharm. Res.* 2012, 29, 3033-3039.
15. Prota, A. E.; Danel, F.; Bachmann, F.; Bargsten, K.; Buey, R. M.; Pohlmann, J.; Reinelt, S.; Lane, H.; Steinmetz, M. O. The novel microtubule-destabilizing drug BAL27862 binds to the colchicine site of tubulin with distinct effects on microtubule organization. *J. Mol. Biol.* 2014, 426, 1848-1860.

Section VIII: Substituted thieno[2,3-d]pyrimidines and Use as Tubulin Targeting Antitumor Agents Targeting microtubule dynamics is an effective approach for cancer chemotherapeutics. Paclitaxel, podophyllotoxin, *vinca* alkaloids, and the epothilones are some examples of natural products which interfere with microtubule dynamics. Multiple agents that bind to the colchicine site on tubulin including the combretastains CA-1P and CA-4P have been evaluated in clinical trials, but thus far no colchicine site agent has been approved for use against cancer. The success of tubulin binding agents is overshadowed by the emergence of multi-drug resistance mechanisms including the expression of P-glycoprotein and/or βIII-tubulin. We previously reported N-(4-methoxyphenyl)-N,2-dimethyl-7H-pyrrolo[2,3-d]pyrimidin-4-amine (1) as a nanomolar inhibitor of the proliferation of human cancer cells (MDA-MB-435). Compound 1 inhibited tubulin polymerization and binding of [$^3$H]colchicine to tubulin. It also circumvented P-glycoprotein and βIII-tubulin mediated resistance. On the basis of the anti-tubulin activity of 1, we designed isosteric thieno[2,3-d]pyrimidine analogs with substitutions at 5 and 6 positions. The design, synthesis and structure activity relationship of these agents with respect to their antitubulin activity is set forth herein.

Section VIII—Table 2:

TABLE 2 sets forth the structures of the compounds of this invention:

| AG no. | Compound No. | Structure |
|---|---|---|
| AG20 | 1 | 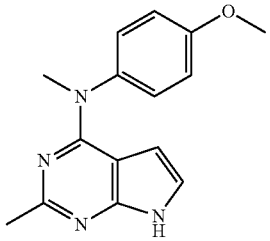 |
| AG329 | 2 | 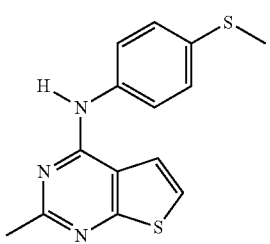 |

TABLE 2-continued sets forth the structures of the compounds of this invention:

| AG no. | Compound No. | Structure |
|---|---|---|
| AG370 | 3 | 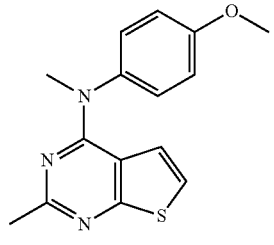 |
| AG328 | 4 | 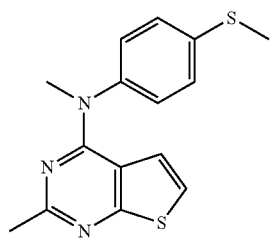 |
| AG372 | 5 | 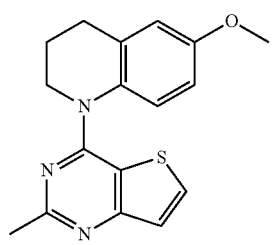 |
| AG371 | 6 | 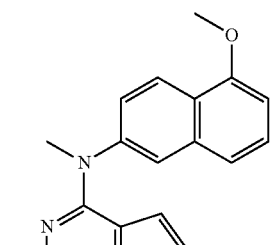 |
| AG330 | 7 | 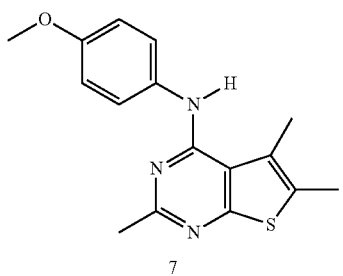 |

TABLE 2-continued sets forth the structures of the compounds of this invention:

| AG no. | Compound No. | Structure |
|---|---|---|
| AG342 | 8 | 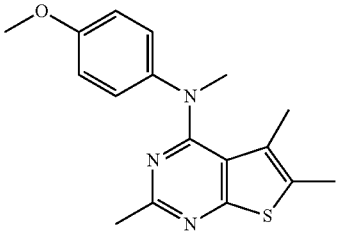 8 |
| AG341 | 9 | 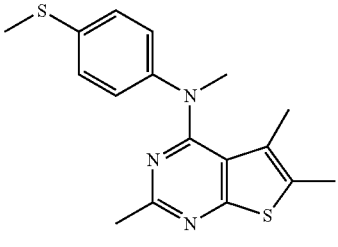 9 |
| AG345 | 10 | 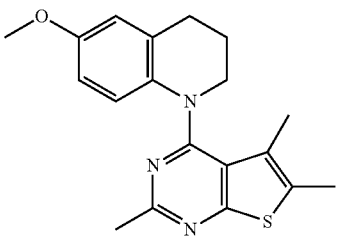 10 |
| AG366 | 11 | 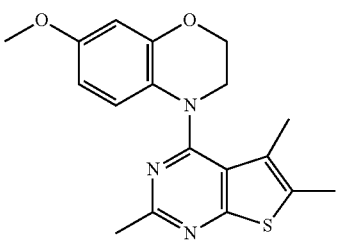 11 |

Microtubules are necessary for several key cellular functions, where continuous equilibrium of microtubule assembly (growth) and disassembly (shortening) make the microtubule dynamic structures important in maintaining cell shape, polarity, and motility and provides a scaffold for cellular trafficking of proteins and organelles. These structures play an integral role in mitosis.[1] Microtubule targeting agents (MTAs) are classified as either stabilizers or destabilizers.[1] The stabilizers promote tubulin assembly by increasing lateral and in some cases longitudinal protofilament interactions,[2] and destabilizers inhibit microtubule (MT) polymerization.[3] There are currently five structurally distinct regions on microtubules where MTAs are bound: First, the taxoid site on the luminal face of the β-subunit;[2,4] Second, the laulimalide/peloruside site on the external face of the β-subunit;[5] Third, the colchicine site at the β-tubulin subunit intradimer interface;[3] Fourth, the vinca site at the α,β-heterodimer interface;[6] and Fifth, the maytansine site.[7] The majority of MT-binding drugs have been derived from natural products and they tend to be easily recognized by P-glycoprotein and pumped out of cancer cells, which cause clinical drug resistance.[8] Section VIII—FIG. 1 shows the chemical structures of known agents.

The vinca alkaloids and taxoids (Section VIII—FIG. 1) have long been used in chemotherapy, with considerable success in cancer management. 2-Methoxyestradiol, combretastatin A-4 (CA-4) Section VIII—(FIG. 1) phosphorylated prodrug combretastatin A-4 phosphate (CA-4P) (fosbretabulin), the combretastain CA-1P prodrug (OXi4503), BNC105P, ABT-751 and plinabulin (NPT-2358) are agents that bind at the colchicine site that have been evaluated in clinical trials.[9] While CA-4P, CA-1P and others continue in clinical trials,[10] to date no colchicine site agent has received FDA approval for anticancer indications, demonstrating the need of developing additional colchicine site agents for potential clinical evaluations.[6] Section VIII—FIG. 2 sets forth the chemical structures 2-11 of the compounds of this invention.

Compounds 2-11 below are the compounds of this invention:

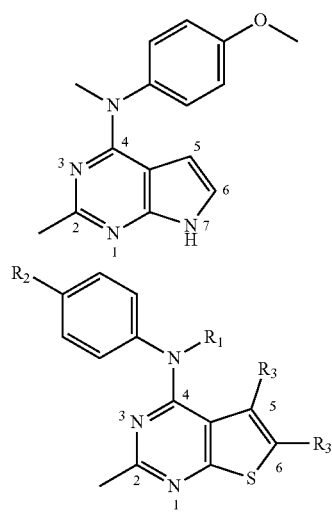

2. $R_1 = H, R_2 = SCH_3, R_3 = H$
3. $R_1 = CH_3, R_2 = OCH_3, R_3 = H$
4. $R_1 = CH_3, R_2 = SCH_3, R_3 = H$
7. $R_1 = H, R_2 = SCH_3, R_3 = CH_3$
8. $R_1 = CH_3, R_2 = OCH_3, R_3 = CH_3$
9. $R_1 = CH_3, R_2 = SCH_3, R_3 = CH_3$

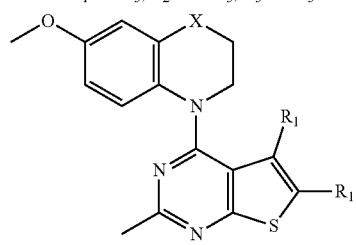

5. $R_1 = H, X = CH_2$
10. $R_1 = CH_3, X = CH_2$
11. $R_1 = CH_3, X = O$

-continued

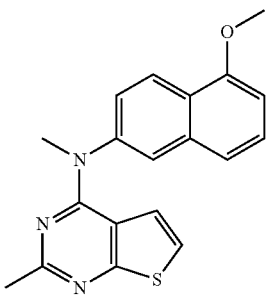
6

In 2010, Gangjee et al.[11] reported the pyrrolo[2,3-d] pyrimidine 1 (Section VIII—FIG. 2) as an inhibitor of human MDA-MB-435 cancer cell proliferation. Compound 1 inhibits the growth of tumor cells with $GI_{50}$ values in the nanomolar range and also circumvents Pgp and βIII-tubulin mediated resistance mechanisms that limit the activity of several MTAs.[11] To evaluate the effect of isosteric replacement of the pyrrole NH of lead 1, compounds 2-11 of the present invention (Section VIII—FIG. 2) were designed with thieno[2,3-d]pyrimidines.

Furthermore, a docking study (not shown) using MOE.2014[3] indicated potential hydrophobic interaction of the S of the thiophene ring with hydrophobic regions of the colchicine site of tubulin was performed. Superimposition of the docked poses of 1, 3, and colchicine in the colchicine site of tubulin was performed. PDB: 4O2B[3]. Superimposition of the docked poses of 4, 9, and colchicine in the colchicine site of tubulin was performed. PDB: 4O2B[3]. Analogs 2-6 were designed on this premise and were expected to improve tubulin inhibitory activity. Additionally 5,6-dimethyl compounds 7-11 were designed as conformationally restricted analogs of the desmethyl analogs 2-6 to restrict the conformation of the phenyl ring relative to the bicyclic thieno[2,3-d]pyrimidine scaffold. From the docked pose of 9 it was apparent that the introduction of the 5,6-dimethyl groups, the N-methyl aniline is oriented such that it reduces its interaction with Cys241 in the active site, and that conformational restriction was further demonstrated by $^1$H NMR study (not shown).

Scheme 1:

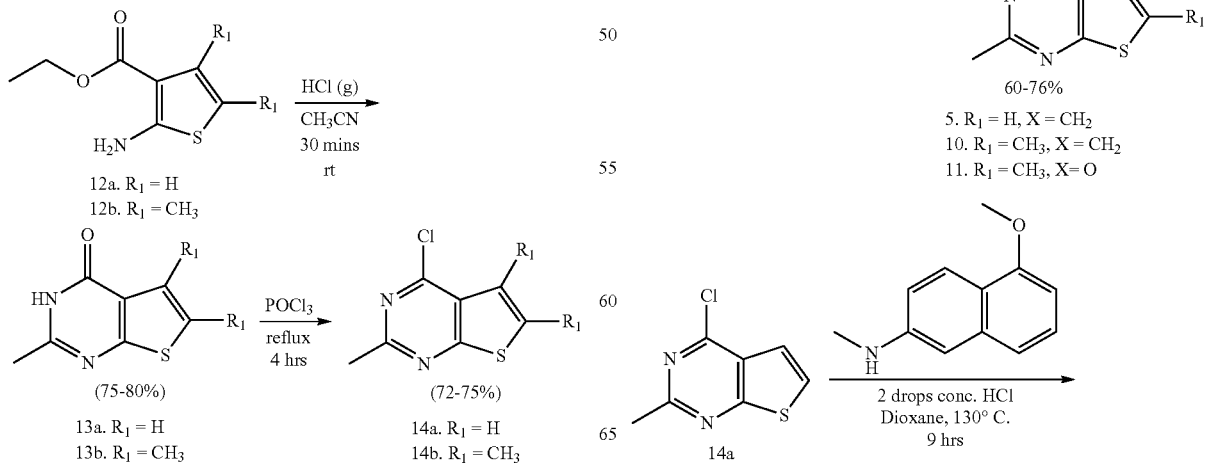

-continued

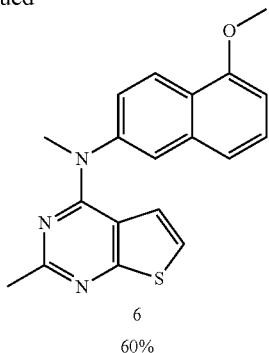

6
60%

The synthesis of target compound 2-11 (Scheme 1), commenced from commercially available ethyl-2-amino-3-thiophenecarboxylate (12a, $R_1$=H) and ethyl-2-amino-4,5-dimethyl-3-thiophenecarboxylate (12b, $R_1$=$CH_3$) obtained using a reported method.[12] Cyclization of 12a and 12b with HCl (g) and acetonitrile gave 13a and 13b followed by chlorination with $POCl_3$ afforded 14a and 14b respectively. Treatment with various substituted anilines in dioxane with 2 drops of conc HCl provided 2-11. (60-76% yields).
Biological Activity:
Section VIII—Table 1:

TABLE 1

$IC_{50}$ values for inhibition of proliferation of MDA-MB-435 cancer cells and $EC_{50}$ values, the concentration that causes 50% loss of cellular microtubules

| Compound No. | $IC_{50}$ ± SD (MDA-MB-435) nM cancer cells | $EC_{50}$ (nM) in A-10 cells (Loss of cellular microtubules) | $EC_{50}/IC_{50}$ Ratio |
| --- | --- | --- | --- |
| 1 | 183 ± 3.4 | 5800 | 31.7 |
| 2 | ND | >10000 | — |
| 3 | 7.6 | 15.4 | 2 |
| 4 | 4.0 ± 0.5 | 10 | 2.5 |
| 5 | 4.3 | 3.6 | 0.83 |
| 6 | 3.8 | 2.5 | 0.65 |
| 7 | ND | >10000 | — |
| 8 | 10.7 ± 1.0 | 18 | 1.7 |
| 9 | 34.8 ± 3.7 | 128 | 3.7 |
| 10 | ND | >10000 | — |
| 11 | ND | 1200 | — |
| CA4 | 3.4 ± 0.6 | 13 | 3.8 |

Compounds 1-11 were evaluated for antiproliferative effects against the MDA-MB-435 cancer cells in culture using the sulforhodamine B assay (SRB assay). Microtubule disrupting effects of 1-11 were also evaluated in a cell-based phenotypic assay. Replacement of the pyrrole ring with thiophene was highly conducive to biological activity. Compound 3 with the thieno[2,3-d]pyrimidine was 24-fold more potent in MDA-MB-435 cancer cell growth inhibition and a remarkable 376-fold more potent at disrupting cellular microtubules as compared to 1. These results clearly demonstrate the in vitro superiority of 3 over 1. In case of 2, which is the NH-hydrogen on N-4 position of 3 was not active in cellular microtubule assay and was not tested further. Compound 4, where the 4'-methoxy aniline of 3 was substituted with 4'-S-methylaniline was one of the more potent compounds in the series where the depolymerization of microtubules was 1.5-fold more potent than 3. The antiproliferative activity ($IC_{50}$) of compound 4 in cancer cells was about 2-fold better than 3. Restriction of the N-4 methyl of 3 as a 6-methoxy tetrahydroquinoline ring as 5 further increases activity for microtubule depolymerization. Finally replacement of the 4'-methoxy-N-methyl aniline with a 5'-methoxy-2'-N-methyl naphthyl moiety increases the activity over 3 and is a remarkable 48-fold and 2300-fold more potent than the parent 1.

For the 5,6-dimethyl thieno[2,3-d]pyrimidine scaffold compound 8 has a slight decrease in activity compared to 3 indicating that the 5,6-dimethyl substitutions are well tolerated. Compound 9 was 8.5 fold less active ($IC_{50}$ value) than 4. Compound 11 had no effects at a concentration of 10 μM in cellular microtubule depolymerization assay and was not tested further. Additionally, 7 and 10 also did not show depolymerization of microtubules at 10 μM indicating that 7 and 10 were inactive against microtubule depolymerization and they were not tested further.

We designed, synthesized and evaluated the isosteric thieno[2,3-d]pyrimidine analogs of 1[11] with methyl substitutions at the 5- and 6-positions. The results suggest that compound 4, where the pyrrole ring of 1 was replaced with thiophene is 45-fold more active than lead compound 1 (comparing $IC_{50}$ values) which indicates that sulfur is probably increasing hydrophobic interactions with the colchicine site where the pyrrole NH does not. The sulfur allows an interaction with the hydrophobic pocket (Val181, Ala180). Moreover, the docked structure of 4 indicates that the SMe aniline moiety is oriented towards Cys241 of colchicine site, which can make S—H bond with cysteine residue.

A proton NMR study was carried out, to explore the conformations of 2, 4, 7 and 9. In compounds 2 and 7 the sigma bonds ($C_1$—N and N—$C_4$) connecting the phenyl ring and thieno[2,3-d]pyrimidine ring are both freely rotatable, while these bonds are somewhat restricted in 4 and 9 where an additional methyl group was introduced on the N-4 position.

The $^1$H NMR spectrum (not shown) shows the 5-H proton in 4 (δ 5.58 ppm) is more shielded than in 2 (δ 7.61 ppm). Similarly, the 5-Me protons in 9 (δ 1.62 ppm) are more shielded than in 7 (δ 2.42 ppm) which suggests a nearby shielding diamagnetic anisotropic cone present in 4 and 9. Due to the bulk of the 4-N-methyl group, the conformations of 4 and 9 are also restricted such that the phenyl ring is conformationally positioned on top of the 5-H (4) and 5-Me (9) which leads to the observed shielding effect in 4 and 9. This $^1$HNMR study defines the aniline ring orientation, in the N4-$CH_3$ analogs 4 and 9, to be oriented on the side of the thieno ring of the thieno[2,3-d]pyrimidine scaffold (not shown).

On the other hand, from proton NMR study of 4 and 9, in compound 9 the sigma bond ($C_1$—N and N—$C_4$) connecting the phenyl ring and thieno[2,3-d]pyrimidine ring are more restricted than 4, because of additional methyl groups at the 5- and 6-positions. According to $^1$H NMR spectrum (not shown), the 2',6' protons in 9 are at δ 6.86 which are more shielded than 4 (δ 7.34 ppm). These values suggest that 2', 6' protons are shielded by the thiophene ring. The bulk of the 4-N-methyl group and the 5- and 6-methyls together create a restricted conformation where 2',6' protons of the phenyl are positioned on top of the thiophene ring. The data suggests that the 8.5 fold less activity of 9 compared to 4 is, in part, due to its orientation of the scaffold, making it further away from Cys241 in colchicine site.

Compounds 10 and 11 are also inactive probably because the side chain 4'-methyl aniline is severely restricted in the presence of the 5,6-dimethyl substitutions and is not conducive to activity.

Compound 3, in which the pyrrole ring is isosterically replaced with a thiophene, shows remarkably better microtubule depolymerization and cancer cell inhibitory activity than 1. The role of the sulfur moiety to increase activity may be additional hydrophobic interactions with the active site Val181 that is lacking in 1 and is responsible for the potent activity of 3. For compounds 4 and 9, a conformational orientation of the 4'-methoxy aniline produced from docked conformations was corroborated from solution NMR studies (not shown). Compound 2 and 7 are inactive probably due to their aniline alignment on the opposite side compared with that of 4 and 9. Inactivity of compound 10 and 11 suggests that the 5, 6-dimethyl groups conformationally restrict the 4'-OMe aniline orienting it in a conformation that is not the bioactive conformation.

Section VIII References:
1) Jordan, M. A. and Wilson, L. Microtubules as a target for anticancer drugs. *Nat. Rev. Cancer* 2004, 4, 253
2) Prota, A. E.; Bargsten, K.; Zurwerra, D.; Field, J. J.; Díaz, J. F.; Altmann, K. H.; Steinmetz, M. O. Molecular mechanism of action of microtubule-stabilizing anticancer agents. *Science* 2013, 339, 587-590.
3) Prota, A. E.; Danel, F.; Bachmann, F.; Bargsten, K.; Buey, R. M.; Pohlmann, J.; Reinelt, S.; Lane, H. and Steinmetz, M. O. The Novel Microtubule-Destabilizing Drug BAL27862 Binds to the Colchicine Site of Tubulin with Distinct Effects on Microtubule Organization. *J. Mol. Biol.* 2014, 426, 1848-1860
4) Nogales, E.; Wolf, S. G.; Downing, K. H. Structure of the α β tubulin dimer by electron crystallography. *Nature* 1998, 391, 199-203
5) Prota, A. E.; Bargsten, K.; Northcote P. T.; Marsh M.; Altmann K. H.; Miller J. H.; Diaz J. F.; Steinmetz M. O. Structural Basis of Microtubule Stabilization by Laulimalide and Peloruside A. *Angew. Chem. Int. Ed.* 2014, 53, 1621-1625
6) Gigant, B.; Wang, C.; Ravelli, R. B.; Roussi, F.; Steinmetz, M. O.; Curmi, P. A., Sobel, A.; Knossow, M. Structural basis for the regulation of tubulin by vinblastine. *Nature* 2005, 435, 519-522
7) Prota, A. E.; Bargsten, K.; Diaz J. F.; Marsh M.; Cuevas C.; Liniger, M.; Neuhaus, C.; Andreu, J. M.; Altmann K. H.; Miller J. H.; Steinmetz M. O. A new tubulin binding site and pharmacophore for microtubule-destabilizing anticancer drugs. *Proc. Natl. Acad. Sci. USA.* 2014, 111, 13817-13821
8) Perez, E. A. Microtubule inhibitors: differentiating tubulininhibiting agents based on mechanisms of action, clinical activity, and resistance. *Mol. Cancer Ther.* 2009, 8, 2086-2095.
9) Ma, T.; Fuld, A. D.; Rigas, J. R.; Hagey, A. E.; Gordon, G. B.; Dmitrovsky, E.; Dragnev, K. H. A phase I trial and in vitro studies combining ABT-751 with carboplatin in previously treated non-small cell lung cancer patients. *Chemotherapy* 2012, 58, 321-9
10) http://www.clinical.trials.gov (Aug. 1, 2015)
11) Gangjee, A.; Zhao, Y; Lin, L.; Raghavan, S.; Roberts, E. G.; Risinger, A. L.; Hamel, E.; Mooberry S. L. Synthesis and Discovery of Water-Soluble Microtubule Targeting Agents that Bind to the Colchicine Site on Tubulin and Circumvent Pgp Mediated Resistance. *J. Med. Chem.* 2010, 53, 8116-8128.
12) Gangjee, A.; Pavana, R. K.; Ihnat, M. A.; Thorpe, J. E.; Disch, B. C.; Bastian, A.; Bailey-Downs, L. C.; Hamel, E. and Bai, R. Discovery of Antitubulin Agents with Antiangiogenic Activity as Single Entities with Multitarget Chemotherapy Potential. *ACS Med. Chem. Lett.* 2014, 5, 480-484

It will be appreciated by those persons skilled in the art that changes could be made to embodiments of the present invention described above without departing from the broad inventive concept thereof. It is understood, therefore, that this invention is not limited by any particular embodiments disclosed, but is intended to cover the modifications that are within the spirit and scope of the invention, as defined by the appended claims.

What is claimed is:
1. A compound of Formula XXVIII:

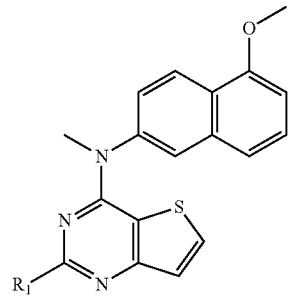

wherein $R_1$ is H or $CH_3$; and optionally including a salt or a hydrate of said compound.

* * * * *